(12) United States Patent
Sakai et al.

(10) Patent No.: US 8,841,105 B2
(45) Date of Patent: Sep. 23, 2014

(54) ORGANIC-INORGANIC COMPOSITE MATERIAL AND PROCESS FOR PRODUCING SAME

(75) Inventors: Takashi Sakai, Okayama (JP); Tadashi Ema, Okayama (JP); Jun Takada, Okayama (JP); Tatsuo Fujii, Okayama (JP); Makoto Nakanishi, Okayama (JP); Hideki Hashimoto, Okayama (JP)

(73) Assignee: National University Corporation Okayama University, Okayama (JP)

( * ) Notice: Subject to any disclaimer, the term of this patent is extended or adjusted under 35 U.S.C. 154(b) by 0 days.

(21) Appl. No.: 13/260,613

(22) PCT Filed: Mar. 26, 2010

(86) PCT No.: PCT/JP2010/055402
§ 371 (c)(1),
(2), (4) Date: Sep. 27, 2011

(87) PCT Pub. No.: WO2010/110435
PCT Pub. Date: Sep. 30, 2010

(65) Prior Publication Data
US 2012/0034670 A1 Feb. 9, 2012

(30) Foreign Application Priority Data

Mar. 27, 2009 (JP) ................................. 2009-078871
Dec. 15, 2009 (JP) ................................. 2009-284465
Jan. 8, 2010 (JP) ................................. 2010-003276

(51) Int. Cl.
*C12N 11/02* (2006.01)

(52) U.S. Cl.
USPC ...................................................... 435/177

(58) Field of Classification Search
USPC ...................................................... 435/177
See application file for complete search history.

(56) References Cited

U.S. PATENT DOCUMENTS

| 6,004,786 | A | 12/1999 | Yamashita et al. | |
|---|---|---|---|---|
| 7,405,042 | B2 | 7/2008 | Matsunaga et al. | |
| 2005/0260600 | A1 | 11/2005 | Matsunaga et al. | |
| 2012/0248368 | A1* | 10/2012 | Takada et al. ............... | 252/62.59 |
| 2012/0315437 | A1* | 12/2012 | Takada et al. ................. | 428/141 |

FOREIGN PATENT DOCUMENTS

| JP | 05-209884 | * | 8/1993 |
|---|---|---|---|
| JP | 09-316554 | * | 9/1997 |
| JP | 9-313179 | | 12/1997 |
| JP | 9-316554 | | 12/1997 |
| JP | 63-247646 | | 10/1998 |
| JP | 2004-150797 | | 5/2004 |
| JP | 2006-280277 | * | 10/2006 |

OTHER PUBLICATIONS

Ema T. et al. Highly Active Lipase Immobilized on Biogenous Iron Oxide . . . Green Chemistry 13(11)3187-3195 2011.*
Sawayama M. et al. Isolation of a Leptothrix Strain . . . Current Microbiology 63(2)173-180, Aug. 2011.*
Reetz M. et al. Efficient Immobilization of Lipases by Entrapment in Hydrophobic Sol-Gel Materials. Biotech & Bioeng 49(5)527-534, 1996.*
International Search Report issued Jun. 22, 2010 in International (PCT) Application No. PCT/JP2010/055402.
H. Hashimoto et al., "Characteristics of Hollow Microtubes Consisting of Amorphous Iron Oxide Nanoparticles Produced by Iron Oxidizing Bacteria, *Leptothrix ochracea*", Journal of Magnetism and Magnetic Materials, vol. 310, pp. 2405-2407, 2007.
M. Kamori et al., "Immobilization of Lipase on a New Inorganic Ceramics Support, Toyonite, and the Reactivity and Enantioselectivity of the Immobilized Lipase", Journal of Molecular Catalysis B: Enzymatic, vol. 9, pp. 269-274, 2000.
H. M. R. Gardimalla et al., "Superparamagnetic Nanoparticle-Supported Enzymatic Resolution of Racemic Carboxylates", Chem. Commun., pp. 4432-4434, 2005.
U. Drechsler et al., "Highly Efficient Biocatalysts via Covalent Immobilization of *Candida rugose* Lipase on Ethylene Glycol-Modified Gold-Silica Nanocomposites", Adv. Mater., vol. 16, No. 3, pp. 271-274, 2004.

* cited by examiner

*Primary Examiner* — Ralph Gitomer
(74) *Attorney, Agent, or Firm* — Wenderoth, Lind & Ponack, L.L.P.

(57) ABSTRACT

Disclosed is an organic-inorganic composite material obtained by chemically modifying a microorganism-derived ceramic material with an organic group, and a process for producing the organic-inorganic composite material. The process is characterized by reacting a microorganism-derived ceramic material with at least one compound selected from the group consisting of silane coupling agents represented by formula (1), silane coupling agents represented by formula (2), and titanate coupling agents represented by formula (3). The organic-inorganic complex can be used in applications for immobilized catalysts and immobilized enzyme catalysts.

16 Claims, 11 Drawing Sheets

Fig. 3-A

Go to top
>X97070|X97070.1 L.cholodnii 16S rRNA gene.
         Length = 1521

Score = 2795 bits (1410), Expect = 0.0
Identities = 1416/1418 (99%)
Strand = Plus / Plus

```
Query: 1    catgccttacacatgcaagtcgaacggtagaggagcaatcctgagagtggcgaacgggt 60
            ||||||||||||||||||||||||||||||||||||||||||||||||||||||||||||
Sbjct: 37   catgccttacacatgcaagtcgaacggtagaggagcaatcctgagagtggcgaacgggt 96

Query: 61   gagtaatgtatcggaacgtgcccagtagtgggggatagcccggcgaaagccggattaata 120
            ||||||||||||||||||||||||||||||||||||||||||||||||||||||||||||
Sbjct: 97   gagtaatgtatcggaacgtgcccagtagtgggggatagcccggcgaaagccggattaata 156

Query: 121  ccgcatgagacctgaggttgaaagcggggggactcgcaagagcctcgcgctactggagcgg 180
            |||||||||||||||||||||||||||||||||||| |||||||||||||||||||||||
Sbjct: 157  ccgcatgagacctgaggttgaaagcggggggactcgcaagagcctcgcgctactggagcgg 216

Query: 181  ccgatatcagattaggtagttggtggggtaaaagcctaccaagcctgcgatctgtagctg 240
            ||||||||||||||||||||||||||||||||||||||||||||||||||||||||||||
Sbjct: 217  ccgatatcagattaggtagttggtggggtaaaagcctaccaagcctgcgatctgtagctg 276

Query: 241  gtctgagaggacgaccagccacactgggactgagacacggcccagactcctacgggaggc 300
            ||||||||||||||||||||||||||||||||||||||||||||||||||||||||||||
Sbjct: 277  gtctgagaggacgaccagccacactgggactgagacacggcccagactcctacgggaggc 336

Query: 301  agcagtggggaattttggacaatgggcgaaagcctgatccagccatgccgcgtgcgggaa 360
            ||||||||||||||||||||||||||||||||||||||||||||||||||||||||||||
Sbjct: 337  agcagtggggaattttggacaatgggcgaaagcctgatccagccatgccgcgtgcgggaa 396

Query: 361  gaaggccttcgggttgtaaaccgcttttgtcaggaagaaatcctttgagttaataccte 420
            ||||||||||||||||||||||||||||||||||||||||||||||||||||||||||||
Sbjct: 397  gaaggccttcgggttgtaaaccgcttttgtcaggaagaaatcctttgagttaataccte 456

Query: 421  ggaggggatgacggtacctgaagaataagcaccggctaactacgtgccagcagccgcggta 480
            ||||||||||||||||||||||||||||||||||||||||||||||||||||||||||||
Sbjct: 457  ggaggggatgacggtacctgaagaataagcaccggctaactacgtgccagcagccgcggta 516

Query: 481  atacgtagggtgcaagcgttaatcggaattactgggcgtaaagcgtgcgcagccggttgt 540
            ||||||||||||||||||||||||||||||||||||||||||||||||||||||||||||
Sbjct: 517  atacgtagggtgcaagcgttaatcggaattactgggcgtaaagcgtgcgcagccggttgt 576

Query: 541  gtaagacagatgtgaaatccccgggctcaacctgggaactgcattgtgactgcacagct 600
            ||||||||||||||||||||||||||||||||||||||||||||||||||||||||||||
Sbjct: 577  gtaagacagatgtgaaatccccgggctcaacctgggaactgcattgtgactgcacagct 636

Query: 601  agagtacggtagaggggggatggaattccgcgtgtagcagtgaaatgcgtagatatgcgga 660
            ||||||||||||||||||||||||||||||||||||||||||||||||||||||||||||
Sbjct: 637  agagtacggtagaggggggatggaattccgcgtgtagcagtgaaatgcgtagatatgcgga 696
```

Fig. 3-B

```
Query: 661  ggaacaccgatggcgaaggcaatcccctggacctgtactgacgctcatgcacgaaagcgt 720
            ||||||||||||||||||||||||||||||||||||||||||||||||||||||||||||
Sbjct: 697  ggaacaccgatggcgaaggcaatcccctggacctgtactgacgctcatgcacgaaagcgt 756

Query: 721  ggggagcaaacaggattagataccctggtagtccacgccctaaacgatgtcaactggttg 780
            ||||||||||||||||||||||||||||||||||||||||||||||||||||||||||||
Sbjct: 757  ggggagcaaacaggattagataccctggtagtccacgccctaaacgatgtcaactggttg 816

Query: 781  ttgggagggtttcttctcagtaacgaagctaacgcgtgaagttgaccgcctggggagtac 840
            ||||||||||||||||||||||||||||||||||||||||||||||||||||||||||||
Sbjct: 817  ttgggagggtttcttctcagtaacgaagctaacgcgtgaagttgaccgcctggggagtac 876

Query: 841  ggccgcaaggttgaaactcaaaggaattgacgggggacccgcacaagcggtggatgatgtg 900
            ||||||||||||||||||||||||||||||||||||||||||||||||||||||||||||
Sbjct: 877  ggccgcaaggttgaaactcaaaggaattgacgggggacccgcacaagcggtggatgatgtg 936

Query: 901  gtttaattcgatgcaacgcgaaaaaccttacctacccttgacatgtcaagaatcttgcag 960
            ||||||||||||||||||||||||||||||||||||||||||||||||||||||||||||
Sbjct: 937  gtttaattcgatgcaacgcgaaaaaccttacctacccttgacatgtcaagaatcttgcag 996

Query: 961  agatgtgggagtgctcgaaagagaacttgaacacaggtgctgcatggccgtcgtcagctc 1020
            ||||||||||||||||||||||||||||||||||||||||||||||||||||||||||||
Sbjct: 997  agatgtgggagtgctcgaaagagaacttgaacacaggtgctgcatggccgtcgtcagctc 1056

Query: 1021 gtgtcgtgagatgttgggttaagtcccgcaacgagcgcaacccttgtcattagttgctac 1080
            ||||||||||||||||||||||||||||||||||||||||||||||||||||||||||||
Sbjct: 1057 gtgtcgtgagatgttgggttaagtcccgcaacgagcgcaacccttgtcattagttgctac 1116

Query: 1081 gaaagggcactctaatgagactgccggtgacaaaccggaggaaggtggggatgacgtcag 1140
            ||||||||||||||||||||||||||||||||||||||||||||||||||||||||||||
Sbjct: 1117 gaaagggcactctaatgagactgccggtgacaaaccggaggaaggtggggatgacgtcag 1176

Query: 1141 gtcctcatggcccttatgggtagggctacacacgtcatacaatggccggtacagagggca 1200
            ||||||||||||||||||||||||||||||||||||||||||||||||||||||||||||
Sbjct: 1177 gtcctcatggcccttatgggtagggctacacacgtcatacaatggccggtacagagggct 1236

Query: 1201 gccaacccgcgagggggagccaatcccagaaaaccggtcgtagtccggatcgcagtctgc 1260
            ||||||||||||||||||||||||||||||||||||||||||||||||||||||||||||
Sbjct: 1237 gccaacccgcgagggggagccaatcccagaaaaccggtcgtagtccggatcgcagtctgc 1296

Query: 1261 aactcgactgcgtgaagtcggaatcgctagtaatcgcggatcagcttgccgcggtgaata 1320
            ||||||||||||||||||||||||||||||||||||||||||||||||||||||||||||
Sbjct: 1297 aactcgactgcgtgaagtcggaatcgctagtaatcgcggatcagcttgccgcggtgaata 1356

Query: 1321 cgttcccgggtcttgtacacaccgcccgtcacaccatgggagcggttctgccagaagta 1380
            ||||||||||||||||||||||||||||||||||||||||||||||||||||||||||||
Sbjct: 1357 cgttcccgggtcttgtacacaccgcccgtcacaccatgggagcggttctgccagaagta 1416

Query: 1381 gttagcctaaccgcaaggagggcgattaccacggcagg 1418
            ||||||||||||||||||||||||||||||||||||||
Sbjct: 1417 gttagcctaaccgcaaggagggcgattaccacggcagg 1454
```

Fig. 4
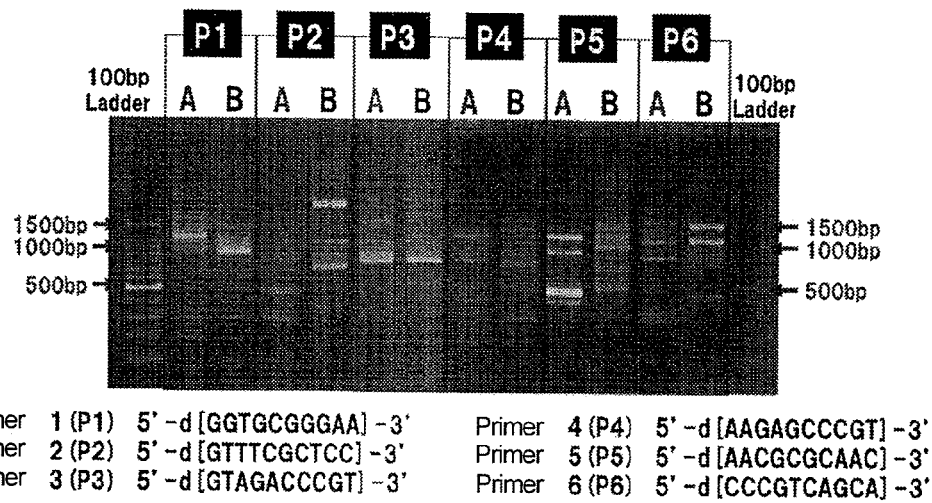
Primer 1 (P1)  5'-d[GGTGCGGGAA]-3'
Primer 2 (P2)  5'-d[GTTTCGCTCC]-3'
Primer 3 (P3)  5'-d[GTAGACCCGT]-3'
Primer 4 (P4)  5'-d[AAGAGCCCGT]-3'
Primer 5 (P5)  5'-d[AACGCGCAAC]-3'
Primer 6 (P6)  5'-d[CCCGTCAGCA]-3'
Fig. 5-A
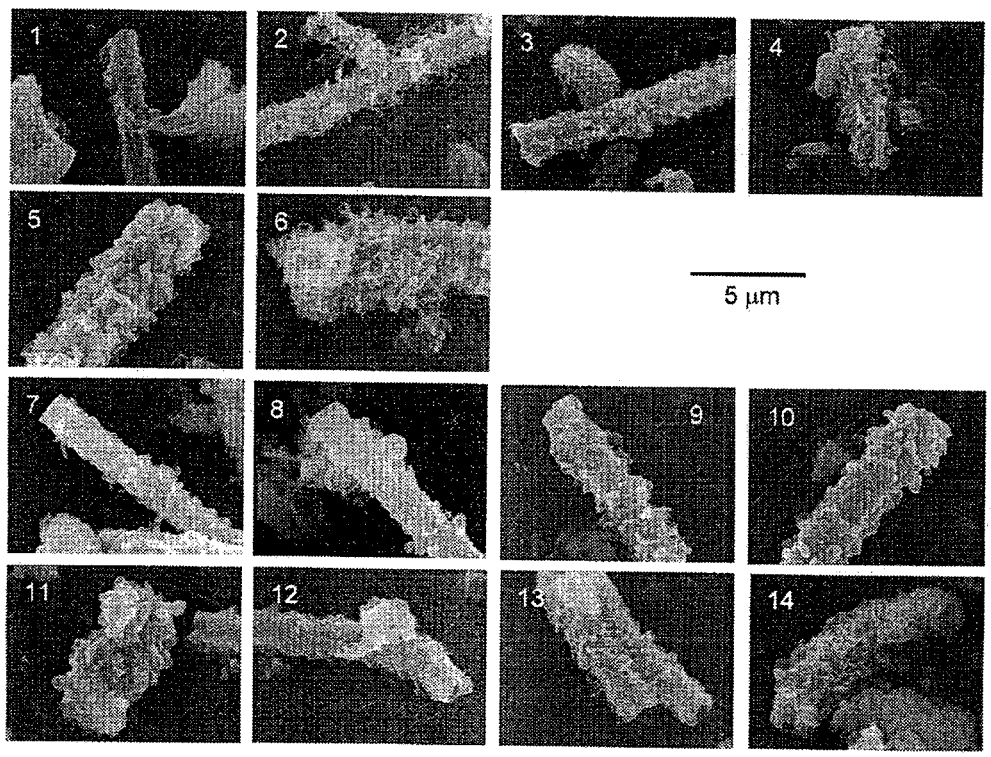

Fig. 5-B
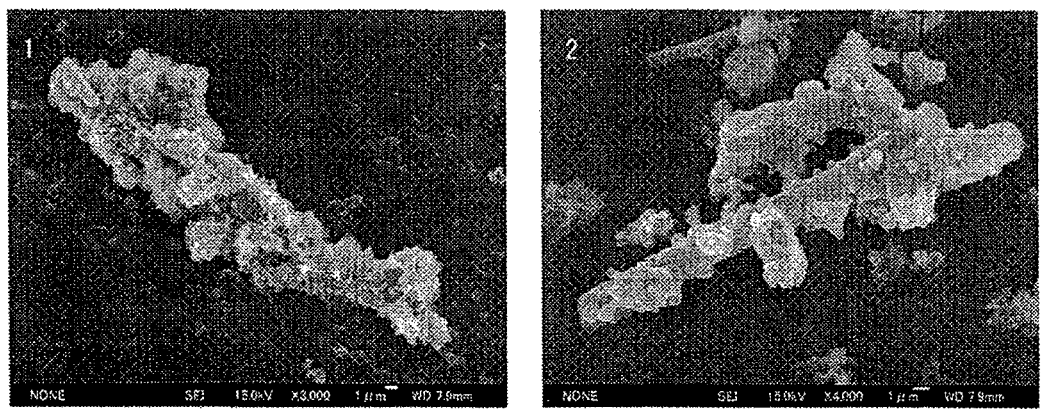
Fig. 6
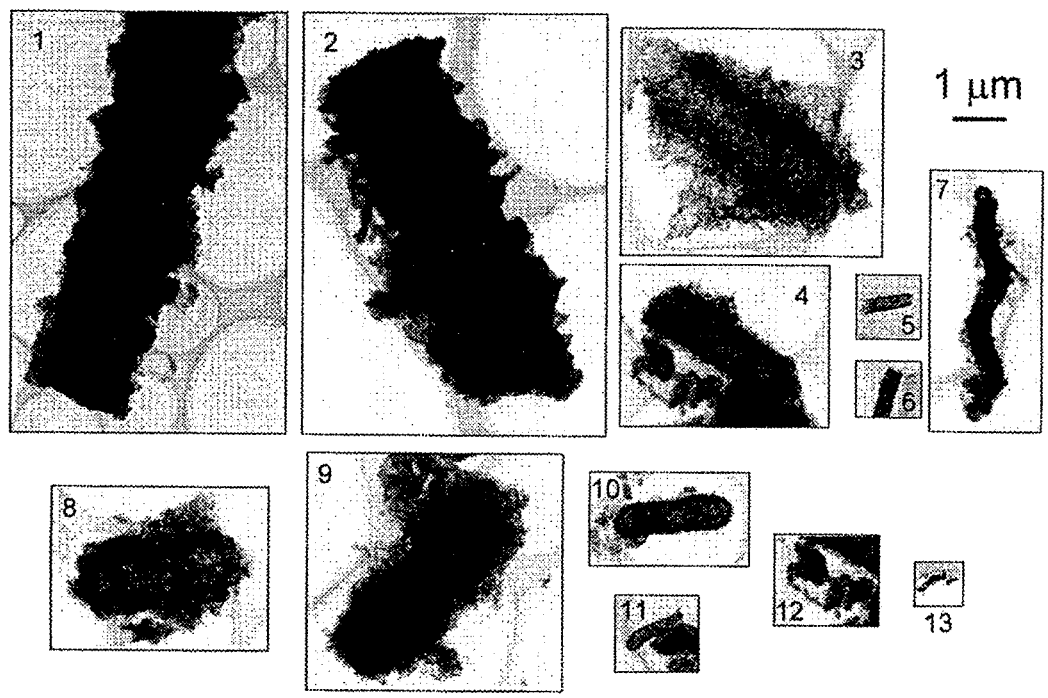

ORGANIC-INORGANIC COMPOSITE MATERIAL AND PROCESS FOR PRODUCING SAME

This application is a U.S. national stage of International Application No. PCT/JP2010/055402 filed Mar. 26, 2010. This application claims foreign priority to JP 2009-078871 filed Mar. 27, 2009, JP 2009-284465 filed Dec. 15, 2009, and JP 2010-003276 filed Jan. 8, 2010.

TECHNICAL FIELD

The present invention relates to an organic-inorganic composite material and a process for producing the organic-inorganic composite material.

BACKGROUND ART

Materials that have a unique shape, size, and composition may have innovative functions and are therefore important. In particular, materials of a unique shape, size, and composition that cannot be made artificially have enormous potential for applications. For example, a ceramic material produced by a representative iron bacterium, *Leptothrix ochracea*, is a sheath-shaped substance with a diameter of about 1 µm and a length of about 200 µm, and the composition of the components other than oxygen is known to have a Fe:Si:P ratio of about 80:15:5. It is also known that the hollow structure of the ceramic material is composed of amorphous nanoparticles with a diameter of 100 nm or less (about 10 to 40 nm) (Non-Patent Document 1).

Ceramic materials produced by iron bacteria, which clog pipes and cause red water, have been only disposed of as waste. However, ceramic materials are worthy of greater attention because they are derived from organisms and thus environmentally friendly, and they mainly consist of the ubiquitous elements iron and silicon and are thus a continuously available unutilized resource. Moreover, any attempt to artificially produce such a unique structure would require a huge amount of time and effort as well as immense technology and energy. Accordingly, the development of a novel material by utilizing a ceramic material derived from nature is highly significant in terms of both of science and technology.

As carriers for enzymes, inorganic materials, such as diatomaceous earth, celite, silica, and glass beads, have been used as is. However, the use of such an inorganic material as is may have problems such as low enzyme loading and enzyme activity impairment. Accordingly, as a material suitable for immobilizing enzymes, the development of an organic-inorganic composite material having a surface modified with an organic group has been progressing. For example, modified kaolinite spherical carriers, modified magnetic nanoparticles, modified gold-silica composite nanoparticles, etc., are known as such materials.

Toyonite-200M, a modified kaolinite spherical carrier, is a material produced by modifying a spherical porous ceramic carrier, Toyonite, obtained by processing kaolinite, with a silane coupling agent. Toyonite-200M can be used for immobilizing an enzyme (Patent Literature (PTL) 1 and Non-patent Literature (NPL) 2).

Modified magnetic nanoparticles are prepared by applying a silane coupling agent to maghemite nanoparticles. Immobilization of the modified magnetic nanoparticles and lipase by a covalent bond is disclosed (Non-Patent Literature (NPL) 3).

Modified gold-silica composite nanoparticles are prepared by self-assembly of silica and gold mediated by a polymeric compound, subsequent sintering treatment, and coordination of the terminal thiol of an organic group on the gold surface. Further, an enzyme is immobilized thereon by a covalent bond with a functional group of the organic group (Non-Patent Document 4).

However, the bond density of the organic group of such known materials is not so high. Accordingly, only about 1 mass %, i.e., a very small amount, of an enzyme can be immobilized thereon. In addition, such known materials have other problems such as an insufficient level of durability of enzyme activity.

Further, for example, lipase, which is an oil and fat hydrolase, can catalyze hydrolysis of an ester bond as well as transesterification and esterification reactions in organic solvents. Further, lipase, which exhibits excellent properties in kinetic optical resolution of racemic compounds, can find a wide variety of application in the fields of organic synthesis and pharmaceuticals. Immobilized lipase comprising diatomaceous earth, celite, Toyonite, or the like as a carrier has already been widely used. However, such an immobilized lipase poses problems such as low enzyme loading, and enzyme activity reduction and enzyme detachment after repeated use. Overcoming these problems would enable repeated use for a longer period using a smaller reactor, resulting in an industrially advantage.

CITATION LIST

Patent Literature

PTL 1: Japanese Unexamined Patent Publication No. 9-313179

Non-Patent Literature

NPL 1: H. Hashimoto, S. Yokoyama, H. Asaoka, Y. Kusano, Y. Ikeda, M. Seno, J. Takada, T. Fujii, M. Nakanishi, R. Murakami Characteristics of hollow microtubes consisting of amorphous ironoxide nanoparticles produced by iron-oxidizing bacteria, *Leptothrix ochracea*. J. Magn. Magn. Mater., 310, 2405-2407 (2007)

NPL 2: M. Kamori, T. Hori, Y. Yamashita, Y. Hirose, Y. Naoshima, Immobilization of lipase on a new inorganic ceramic material support, toyonite, and the reactivity and enantioselectivity of the immobilized lipase. J. Mol. Catal. B: Enzymatic, 9, 269-274 (2000)

NPL 3: H. M. R. Gardimalla, D. Mandal, P. D. Stevens, M. Yen, Y. Gao, SupeLparamagnetic nanoparticle-supported enzymatic resolution of racemic carboxylates. Chem. Commun., 4432-4434 (2005)

NPL 4: U. Drechsler, N. O. Fischer, B. L. Frankamp, V. M. Rotello, Highly efficient biocatalysts via covalent immobilization of *Candida rugosa* lipase on ethylene glycol-modified gold-silica nanocomposites. Adv. Mater., 16, 271-274 (2004)

SUMMARY OF INVENTION

Technical Problem

A main object of the present invention is to provide a novel organic-inorganic composite material produced by performing an artificial treatment while maintaining various shape features of a ceramic material, and a process for producing the organic-inorganic composite material.

Solution to Problem

In view of the above problem of the prior art, the present inventors carried out extensive research and found that when a ceramic material obtained from nature, which has various unique shape features, is chemically treated, an organic-inorganic composite material produced by chemical modification with an organic group can be obtained. The inventors further found that a catalyst, etc., can be immobilized on the thus obtained organic-inorganic composite material by utilizing an organic group introduced into the organic-inorganic composite material. The present invention has been accomplished by conducting further extensive research based on these findings.

Thus, the present invention provides the organic-inorganic composite material, process for producing the organic-inorganic composite material, and composite material produced using the organic-inorganic composite material shown in Items 1 to 30 below.

Item 1. An organic inorganic composite material obtained by chemically modifying a microorganism-derived ceramic material with an organic group.

Item 2. The organic inorganic composite material according to Item 1, wherein the microorganism-derived ceramic material contains a Fe atom and a Si atom.

Item 3. The organic inorganic composite material according to Item 1 or 2, wherein the microorganism-derived ceramic material is a material to which magnetism has been imparted.

Item 4. The organic inorganic composite material according to any one of Items 1 to 3, wherein the microorganism is an iron bacterium.

Item 5. The organic inorganic composite material according to any one of Items 1 to 4, wherein the microorganism belongs to the genus *Leptothrix, Gallionella, Sphaerotilus, Clonothrix, Toxothrix, Sideromonas, Siderocapsa,* or *Siderococcus*.

Item 6. The organic inorganic composite material according to any one of Items 1 to 5, wherein the microorganism is *Leptothrix cholodnii*.

Item 7. The organic inorganic composite material according to any one of Items 1 to 6, wherein the microorganism is *Leptothrix cholodnii* OUMS1 (NITE BP-860).

Item 8. The organic inorganic composite material according to any one of Items 1 to 7, wherein the ceramic material is in the shape of a sheath, a spiral, a bar, a grain, a microtube, a nanotube, a hollow string, a capsule, a thread-like and sphere-like agglomerate, a string, or a rod.

Item 9. The organic inorganic composite material according to any one of Items 1 to 5 and 8, wherein the microorganism is *Leptothrix ochracea*.

Item 10. The organic inorganic composite material according to any one of Items 1 to 9, wherein the organic group contains at least one functional group selected from the group consisting of a carboxyl group, a carboxylic acid ester group, an amide group, an imido group, a cyano group, an isocyano group, an aldehyde group, a ketone group, an imino group, an amino group, an azido group, a nitro group, a hydroxy group, an ether group, an epoxy group, an isocyanato group, an isothiocyanato group, alkyl groups, aryl groups, alkenyl groups, alkynyl groups, a thiol group, a sulfide group, a sulfonic acid group, a sulfonic acid ester group, a sulfoxide group, heterocyclic rings, halogen atoms, a silicon atom, a titanium atom, and a phosphorus atom.

Item 11. The organic inorganic composite material according to any one of Items 1 to 10, wherein an oxygen atom bound to the Fe atom and/or Si atom contained in the ceramic material is bound to silicon, titanium, aluminum, or phosphorus contained in the organic group.

Item 12. An organic inorganic composite material according to Item 11, wherein at least one atom selected from the group consisting of silicon, titanium, aluminum, and phosphorus contained in the organic group is derived from a silane coupling agent, a titanate coupling agent, an aluminate coupling agent, and a phosphorus coupling agent, respectively.

Item 13. The organic inorganic composite material according to any one of Items 1 to 12, wherein the chemical modification with the organic group is performed by reacting the microorganism-derived ceramic material with at least one member selected from the group consisting of silane coupling agents, titanate coupling agents, aluminate coupling agents, and phosphorus coupling agents.

Item 14. The organic inorganic composite material according to Item 12 or 13, wherein the silane coupling agent is at least one member selected from:
compounds represented by formula (1):

$$Y-R^1-Si(R^2)_n(R^3)_{3-n} \quad (1)$$

(wherein Y represents $R^4R^5N-$, $R^7R^8N-R^6-NR^4-$, $R^{11}R^{10}N-R^9-R^7N-R^6-NR^4-$ an alkyl group, a phenyl group, a 3,4-epoxycyclohexyl group, a halogen atom, a mercapto group, an isocyanate group, an optionally substituted glycidyl group, a glycidoxy group, an optionally substituted vinyl group, a methacryloxy group ($CH_2=C(CH_3)COO-$), an acryloxy group ($CH_2=CHCOO-$), a ureido group ($NH_2CONH-$), an optionally substituted methacryl group, an optionally substituted epoxy group, an optionally substituted phosphonium halide group, an optionally substituted ammonium halide group, or an optionally substituted acryl group; $R^4$, $R^5$, $R^7$, $R^8$, $R^{10}$ and $R^{11}$ independently represent a hydrogen atom or a $C_{1-6}$ alkyl group; $R^6$ and $R^9$ independently represent a $C_{2-6}$ alkylene group; $R^1$ is a single bond, an alkylene group, or a phenylene group; or $R^1$ and Y ($Y-R^1$) conjointly represent a vinyl group; each $R^2$ independently represents an alkyl group or a phenyl group; each $R^3$ independently represents a hydroxy group or an alkoxy group; and n is an integer of 0 to 2); and compounds represented by formula (2):

$$R^{12}{}_3Si-NH_mR^{13}{}_{2-m} \quad (2)$$

(wherein each $R^{12}$ independently represents an alkyl group, each $R^{13}$ independently represents an alkyl group or an alkylsilane group, and m is an integer of 0 to 2).

Item 15. The organic-inorganic composite material according to any one of Items 12 to 14, wherein the silane coupling agent is at least one member selected from the group consisting of 3-aminopropyltriethoxysilane, 3-methacryloxypropyltrimethoxysilane, 3-mercaptopropyltrimethoxysilane, 3-chloropropyltriethoxysilane, 3-glycidoxypropyltrimethoxysilane, phenyltrimethoxysilane, n-octadecyltriethoxysilane, 3-(triethoxysilyl)propyltriphenylphosphonium bromide, 3-(triethoxysilyl)propylammonium bromide, and hexamethyldisilazane.

Item 16. The organic-inorganic composite material according to Item 12 or 13, wherein the titanate coupling agent is a compound represented by formula (3):

$$Y-R^1-Ti(R^2)_n(R^3)_{3-n} \quad (3)$$

(wherein Y represents $R^4R^5N-$, $R^7R^8N-R^6-NR^4-$, or $R^{11}R^{10}N-R^9-R^7N-R^6-NR^4-$; or Y and $R^1$ ($Y-R^1$) conjointly represents a vinyl group, an alkyl group, a phenyl group, a 3,4-epoxycyclohexyl group, a halogen atom, a mercapto group, an isocyanate group, an optionally substituted glycidyl group, a glycidoxy group, an optionally substituted vinyl group, a methacryloxy group ($CH_2=C(CH_3)COO-$), an acryloxy group ($CH_2$=CHCOO—), a ureido group ($NH_2$CONH—), an optionally substituted methacryl group, an optionally substituted epoxy group, an optionally substituted phosphonium halide group, an optionally substituted ammonium halide group, or an optionally substituted acryl group; $R^4$, $R^5$, $R^7$, $R^8$, $R^{10}$, and $R^{11}$ independently represent a hydrogen atom or a $C_{1-6}$ alkyl group; $R^6$ and $R^9$ independently represent a $C_{2-6}$ alkylene group; $R^1$ is a single bond, an alkylene group, or a phenylene group; or $R^1$ and Y (Y—$R^1$) conjointly represent a vinyl group; each $R^2$ independently represents an alkyl group or a phenyl group; each $R^3$ independently represents a hydroxy group or an alkoxy group; and n is an integer of 0 to 2.

Item 17. The organic-inorganic composite material according to Item 12, 13, or 16, wherein the titanate coupling agent is at least one member selected from the group consisting of 3-aminopropyltriethoxytitanium, 3-methacryloxypropyltrimethoxytitanium, 3-mercaptopropyltrimethoxytitanium, 3-chloropropyltriethoxytitanium, 3-glycidoxypropyltrimethoxytitanium, phenyltrimethoxytitanium, and n-octadecyltriethoxytitanium.

Item 18: The organic-inorganic composite material according to any one of Items 1 to 17, wherein the organic group functions as a catalyst.

Item 19. A catalytic-organic-inorganic composite material comprising the organic-inorganic composite material of any one of Items 1 to 17, and a catalyst immobilized thereon.

Item 20. The catalytic-organic-inorganic composite material according to Item 19, wherein the catalyst is at least one member selected from the group consisting of enzymes, organic catalysts, and metal complex catalysts.

Item 21. An organic-inorganic composite material comprising the organic-inorganic composite material of any one of Items 1 to 17 and a dye immobilized thereon.

Item 22. The organic-inorganic composite material according to Item 21, wherein the dye is a fluorescent dye.

Item 23. The organic-inorganic composite material according to Item 21 or 22, wherein the dye is a porphyrin dye.

Item 24. A process for producing an organic-inorganic composite material, comprising reacting a microorganism-derived ceramic material with at least one member selected from the group consisting of:

silane coupling agents represented by formula (1):

(wherein Y represents $R^4R^5N$—, $R^7R^8N$—$R^6$—$NR^4$—$R^{11}R^{10}N$—$R^9$—$R^7N$—$R^6$—$NR^4$—, an alkyl group, a phenyl group, a 3,4-epoxycyclohexyl group, a halogen atom, a mercapto group, an isocyanate group, an optionally substituted glycidyl group, a glycidoxy group, an optionally substituted vinyl group, a methacryloxy group ($CH_2$=C($CH_3$)COO—), an acryloxy group ($CH_2$=CHCOO—), a ureido group ($NH_2$CONH—), an optionally substituted methacryl group, an optionally substituted epoxy group, an optionally substituted phosphonium halide group, an optionally substituted ammonium halide group, or an optionally substituted acryl group; $R^4$, $R^5$, $R^7$, $R^8$, $R^{10}$ and $R^{11}$ independently represent a hydrogen atom or a $C_{1-6}$ alkyl group; $R^6$ and $R^9$ independently represent a $C_{2-6}$ alkylene group; $R^1$ is a single bond, an alkylene group, or a phenylene group; or $R^1$ and Y (Y—$R^1$) conjointly represent a vinyl group; each $R^2$ independently represents an alkyl group or a phenyl group; each $R^3$ independently represents a hydroxy group or an alkoxy group; and n is an integer of 0 to 2);

silane coupling agents represented by formula (2):

(wherein each $R^{12}$ independently represents an alkyl group, each $R^{13}$ independently represents an alkyl group or an alkylsilane group, and m is an integer of 0 to 2); and titanate coupling agents represented by formula (3):

(wherein Y, $R^1$, $R^2$, $R^3$, and n are as defined above) to chemically modify the organism-derived ceramic material with an organic group.

Item 25. A process for producing an organic-inorganic composite material, comprising further performing a chemical modification by utilizing the organic group contained in the organic-inorganic composite material obtained by the process of Item 24.

Item 26. A process for producing a catalytic-organic-inorganic composite material, comprising immobilizing a catalyst on the organic group contained in the organic-inorganic composite material obtained by the process of Item 24 or 25.

Item 27. The process for producing a catalytic-organic-inorganic composite material according to item 26, wherein the catalyst is at least one member selected from the group consisting of enzymes, organic catalysts, and metal complex catalysts.

Item 28. A process for producing an organic-inorganic composite material, comprising binding a dye to the organic group contained in the organic-inorganic composite material obtained by the process of Item 24.

Item 29. A process for producing an organic-inorganic composite material according to item 28, wherein the dye is a porphyrin dye.

Item 30. An immobilized catalyst comprising the organic-inorganic composite material of Item 18 or the catalytic-organic-inorganic composite material of Item 19 of 20 as an active ingredient.

Advantageous Effects of Invention

According to the present invention, a nature-derived ceramic material that has various unique shape features is chemically treated to produce an organic-inorganic composite material by chemical modification with an organic group. In particular, such a ceramic material is reacted with a silane coupling agent, etc., that can bind an organic material and an inorganic material to produce a ceramic material having any of various organic groups and functional groups introduced on the surface (a chemically modified ceramic material).

Further, a catalyst, etc., can be immobilized on the ceramic material by utilizing various functional groups introduced into the ceramic material. A chemically modified ceramic material that has a catalyst, etc., immobilized thereon can exhibit excellent catalytic properties and the like based on various shape features of the original ceramic material.

Further, according to the present invention, the magnetic ceramic material produced by imparting magnetism to a microorganism-derived ceramic material can be chemically modified. Because a material having magnetism imparted thereto is attracted and attaches to magnets, the chemically modified magnetic ceramic material can be easily collected and reused. Accordingly, this material can be expected to be used in various fields where magnetic iron oxide has been used, such as in the ceramics industry, chemical industry, electronics industry, biotechnology industry, and field of medicine.

BRIEF DESCRIPTION OF DRAWINGS

FIG. 3-A shows the results of homology search showing 16S ribosomal DNA nucleotide sequence of OUMS1 strain (upper row) and that of a known iron-oxidizing bacteria *Leptothrix cholodnii* SP-6 strain (lower row).

FIG. 3-B shows the results of homology search showing 16S ribosomal DNA nucleotide sequence of OUMS1 strain (upper row) and that of a known iron-oxidizing bacteria *Leptothrix cholodnii* SP-6 strain (lower row).

FIG. 4 compares genomic DNA electrophoretic patterns of OUMS1 strain (A) and an iron-oxidizing bacteria *Leptothrix cholodnii* SP-6 strain (B).

FIG. 5-A shows SEM images of the iron oxide formed by OUMS1 strain.

FIG. 5-B shows SEM images of the iron oxide formed by OUMS1 strain.

FIG. 6 shows TEM images of the iron oxide formed by OUMS1 strain.

DESCRIPTION OF EMBODIMENTS

Figure 1:
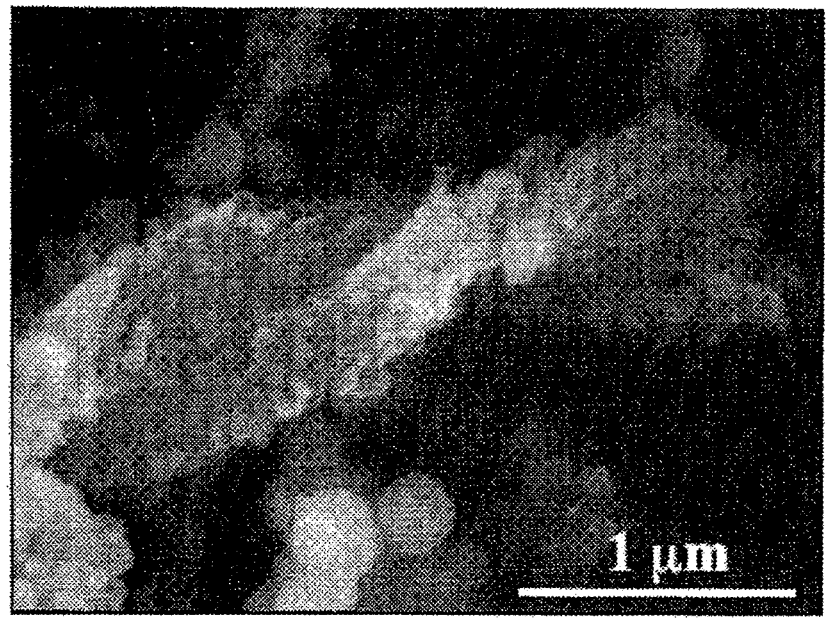
FIG. 1 shows an SEM photograph of *Gallionella ferruginea*-derived ceramic material in the shape of a spiral obtained in the isolation and purification of microorganism-derived ceramic material (2).

The organic-inorganic composite material of the present invention is obtained by chemically modifying a microorganism-derived ceramic material with an organic group. (Hereinafter, the ceramic material chemically modified with an organic group may be sometimes simply referred to as "chemically modified ceramic material".)

Microorganism-Derived Ceramic Material

Ceramic materials are inorganic substances produced by various bacteria and are known to have a variety of shapes. The ceramic material as used in the present invention preferably contains a Fe atom and a Si atom on the surface. In the present invention, the surface of the ceramic material refers to a portion of the ceramic material that may be in contact with the exterior. For example, when the ceramic material has a sheath-like structure, the surface includes the outer and inner surfaces of the sheath structure. When the surface of the sheath structure has a net-like structure, the surface further includes the inner surface of the network structure.

Examples of microorganisms that produce ceramic materials include iron bacteria. Habitats for iron bacteria are, for example, rivers, ponds, the ground, and paddy fields. Iron bacteria produce inorganic substances (ceramic materials) of various shapes, such as the shape of a sheath, spiral, bar, and grain.

Examples of iron bacteria that can be used in the present invention include microorganisms that belong to the genus *Leptothrix, Gallionella, Sphaerotilus, Clonothrix, Toxothrix, Sideromonas, Siderocapsa*, and *Siderococcus* (see, for example, edited by Sadao Kojima, Ryuichi Sudo, and Mitsuo chihara: "Pictoral Book of Environmental Microorganisms", Kodansha, Ltd., (1995)).

In the present invention, when ceramic materials of various shapes produced by various microorganisms have a Fe atom and/or a Si atom on the surface, such ceramic materials can be modified with an organic group by binding the organic group to or adsorbing the organic group on an oxygen atom bound to the Fe atom and/or Si atom.

For example, *Leptothrix ochracea*, which is a representative iron bacterium, is known to produce a sheath-shaped ceramic material. (The sheath-shaped ceramic material produced by *Leptothrix ochracea* may be hereinafter sometimes referred to as "sheath shaped ceramic material" or "biogenous iron oxide".) The ceramic material produced by *Leptothrix ochracea* is a sheath shaped substance with a diameter of about 1 μm and a length of about 200 μm, and is an oxide that contains, in addition to iron and oxygen, trace amounts of silicon and phosphorus. Moreover, the sheath-shaped structure is composed of nanoparticles with a diameter of 100 nm or less (about 10 to 40 nm). The kinds and ratio of the components, such as iron, silicon, and phosphorus, contained in ceramics produced by the same kind of microorganism and phosphorus, may vary according to the environment of the microorganism.

The sheath shaped ceramic material produced by *Leptothrix ochracea* is present, for example, in a sediment precipitated in a gravity filtration facility of a water purification plant. The *Leptothrix ochracea*-derived ceramic material can be purified by subjecting the sediment to centrifugation, drying under reduced pressure, etc.

In addition to *Leptothrix ochracea*, which produces a sheath-shaped ceramic material, *Gallionella*, for example, is known to produce a spiral ceramic material; *Sphaerotilus* and *Clonothrix* are known to produce a branched tubular or thread-shaped ceramic material; *Toxothrix* is known to produce a thread-shaped (harp-shaped, pie-wedge-shaped) ceramic material; *Sideromonas* is known to produce a short trunk-like ceramic material; *Siderocapsa* is known to produce a capsule-shaped ceramic material; and *Siderococcus* is known to produce a spherical ceramic material (see, for example, edited by Sadao Kojima, Ryuichi Sudo, and Mitsuo Chihara "Pictoral Book of Environmental Microorganisms", Kodansha, Ltd. (1995)). These ceramic materials can be isolated, purified and analyzed by the same methods as those for biogenous iron oxide produced by *Leptothrix ochracea*.

In the present invention, ceramic materials derived from microorganisms that produce iron oxide having a low-crystalline iron oxide ferrihydrite structure can be used as microorganism-derived (iron bacteria-derived) ceramic materials.

The ferrihydrite as used herein refers to a low-crystalline iron oxide. Ferrihydrite is called 2-line ferrihydrite, 6-line ferrihydrite, etc. depending on the number of peaks that appear in the X-ray diffraction pattern. The composition of 2-line ferrihydrite is considered to be $Fe_4(O, OH, H_2O)$, and the composition of 6-line ferrihydrite is considered to be $Fe_{4.6}(O, OH, H_2O)_{12}$ (R. A. Eggleton and R. W. Fitzpatrick, "New data and a revised structural model for ferrihydrite", Clays and Clay Minerals, Vol. 36, No. 2, pages 111 to 124, 1988).

Although any microorganism that can produce iron oxide having a ferrihydrite structure may be used, the microorganism is preferably *Leptothrix cholodnii*. One example of such a microorganism is a *Leptothrix cholodnii* OUMS1 strain isolated from a water purification plant. The *Leptothrix cholodnii* OUMS1 strain can produce iron oxide having a ferrihydrite structure. Mycological and genetic properties of the *Leptothrix cholodnii* OUMS1 strain are shown below.

(i) Mycological Properties

The *Leptothrix cholodnii* OUMS1 strain is a bacillus with a length of several micrometers and a width of about 1 μm. At the single-cell stage, this strain actively moves using a flagellum. As the cell grows, both ends of the cell are connected, and a fibrous material comprising a polysaccharide and a protein is formed around the cell. As a result, this cell cannot be uniformly present in a liquid medium and is in an aggregated and precipitated state. When iron and manganese are added to the medium, iron oxide and manganese oxide adhere to the fibrous material that is present outside of the cell, thus forming a sheath-shaped structure. The cell forms a white amorphous fibrous colony on an agar medium. When iron is added, the colony becomes yellowish brown. When manganese is added, the colony becomes brown.

(ii) Genetic Properties

The nucleotide sequence of 16S rDNA of the *Leptothrix cholodnii* OUMS1 strain is shown in SEQ ID NO: 1 of the Sequence Listing. A BLAST search was performed on the DDBJ database for the nucleotide sequence of 16S rDNA. The results of this search and the mycological properties described above confirmed that this cell belongs to *Leptothrix cholodnii*.

The *Leptothrix cholodnii* OUMS1 strain was deposited as Accession No. NITE P-860 in the National Institute of Technology and Evaluation, Patent Microorganisms Depositary (Kazusa Kamatari 2-5-8, Kisarazu, Chiba, 292-0818, Japan) on Dec. 25, 2009. This bacterial strain has been transferred to an international deposit under Accession No. NITE BP-860.

In addition to the *Leptothrix cholodnii* OUMS1 strain, other examples of *Leptothrix cholodnii* that can produce iron oxide having a ferrihydrite structure include *Leptothrix cholodnii* having 16S rDNA consisting of the nucleotide sequence shown in SEQ ID NO: 1. Specific examples of microorganisms that can produce iron oxide having a ferrihydrite structure include microorganisms having 16S rDNA consisting of the nucleotide sequence shown in SEQ ID NO: 1.

The ceramic material derived from *Leptothrix cholodnii* or microorganisms that can produce iron oxide may be in the shape of a microtube, a nanotube, a hollow string, a capsule, a string-like and sphere-like agglomerate, a string, a rod, or the like.

The microorganism-derived ceramic material containing an iron atom is known to have various structures as described above. The size of the microorganism-derived ceramic material containing an iron atom as used herein may vary depending on the kind of material, and is typically about 0.1 to 3000 μm.

More specifically, for example, the ceramic material in the shape of a sheath, a spiral, a branched tube, a thread, or a short trunk typically has a diameter of about 0.1 to 5 μm and a length of about 5 to 3000 μm. The capsule-shaped ceramic material typically has a length of about 1.2 to 24 μm. The spherical ceramic material has a diameter of about 0.1 to 1 μm. The microtubular ceramic material has a diameter of about 0.3 to 4 μm, and a length of about 5 to 200 μm. The nanotubular ceramic material has a diameter of about 300 to 450 nm and a length of about 5 to 200 μm. The hollow string-shaped ceramic material has a length of about 3 to 10 μm. The capsule-shaped ceramic material has a major axis of 1.5 to 7 μm and a minor axis of 0.5 to 3 μm. The thread-shaped ceramic material has a length of about 0.5 to 5 μm. The rod-shaped ceramic material has a length of about 5 to 30 μm.

The microorganism-derived ceramic material preferably contains silicon, phosphorus, etc., in addition to an iron atom. The microorganism-derived ceramic containing an iron atom typically contains an oxygen atom, a carbon atom, and a hydrogen atom.

For example, the microorganism is cultured in an environment where a transition metal element such as cobalt, nickel, or manganese, a rare earth element such as neodymium, and the like are present, whereby the resulting microorganism-derived ceramic material can contain these elements. When the ceramic material contains these elements, the magnetic ceramic material of the present invention can have magnetism derived from substances other than iron. The ceramic material may further contain light elements, such as sodium, magnesium, and aluminum.

The ceramic material derived from *Leptothrix cholodnii* or iron oxide-producing microorganisms has a ferrihydrite structure and a fibrous or scaly surface, which are features of this ceramic material.

The surface refers to an outer surface of the tube. The term "fibrous" refers to the state of a surface where thread-like materials are complicatedly tangled with each other. The term "scaly" refers to a surface that is covered with scaly substances.

The components include, for example, Fe, O, Si, and P. The iron oxide typically further includes a carbon atom and a hydrogen atom. It is usually preferable that the element ratio of iron, silicon, and phosphorus is approximately 66-87:2-27:1-32 by atomic %. The iron oxide of the present invention may be an aggregate of ferrihydrite microparticles with a primary particle diameter of about 3 to 5 nm.

The organic-inorganic composite material of the present invention can be obtained by reacting a compound having an organic group in the molecule with an oxygen atom (for example, a hydroxyl-derived oxygen) bound to a Fe atom and/or a Si atom present on the surface of a ceramic material as mentioned above. More specifically, the organic-inorganic composite material of the present invention is obtained by chemically modifying at least part of a ceramic material that can be chemically modified with an organic group (e.g., an oxygen bound to an Fe atom and/or a Si atom) with an organic group. This chemical modification results in the formation of an organic-inorganic composite material wherein an oxygen atom bound to a Fe atom and/or a Si atom contained in the ceramic material is bound to one of the silicon, titanium, aluminum, and phosphorus contained in the organic group.

Magnetic Microorganism-Derived Ceramic Material

Further, in the present invention, the microorganism-derived ceramic material to which magnetism (the property of attraction to magnets) has been imparted (hereinafter referred to as "magnetic ceramic material") may be chemically modified in the same manner as above to produce an organic-inorganic composite material. A method for imparting magnetism to a microorganism-derived ceramic material may be, for example, a method comprising heat-treating a microorganism-derived ceramic material containing an iron atom.

The heat-treatment conditions are not particularly limited, insofar as the iron atom contained in the microorganism-derived ceramic material is reduced and oxidized to a magnetic iron oxide (for example, $Fe_3O_4$ and $\gamma$-$Fe_2O_3$). The heat treatment of the present invention includes heating accompanied by oxidation, heating accompanied by reduction, and heating not accompanied by oxidation or reduction. The heat treatment may be carried out, for example, by an oxidation method comprising heating at 700 to 900° C. in the presence of an oxygen gas (for example, atmospheric air), a hydrogen reduction method comprising heating at about 400 to 650° C. in the presence of hydrogen gas, or a method of mixing a starting material ceramic material with an aqueous alkali solution containing a $Fe^{2+}$ ion prepared by replacement with $N^2$ gas and heating the resulting mixture under reflux (see, for example, "S. A. Kahani and M. Jafari, J. Magn. Magn. Mater., 321 (2009) 1951-1954", etc.).

A preferable method (heat treatment) for producing the magnetic ceramic material is, for example, a method comprising the following steps (1) and (2):
(1) heating a microorganism-derived ceramic material containing an iron atom; and
(2) reducing the ceramic material obtained in step (1) by heating in the presence of hydrogen gas.

The heat treatment comprising the above steps (1) and (2) produces a magnetic ceramic material mainly containing $Fe_3O_4$.

Another example of a preferable method (heat treatment) for producing the magnetic ceramic material of the present invention is a method comprising the following step (3) in addition to the heat treatment comprising the above steps (1) and (2):
(3) heating the magnetic ceramic material obtained in step (2) in the presence of oxygen gas (an oxidation-annealing step).

The heat treatment comprising the above steps (1) to (3) produces a magnetic ceramic material mainly containing $\gamma$-$Fe_2O_3$.

The heating temperature in step (1) is preferably about 700 to 900° C., more preferably about 750 to about 850° C., and particularly preferably about 800° C. Further, the heating treatment in step (1) can be carried out, for example, in an atmosphere in the presence of oxygen (for example, in atmospheric air). The heating time is typically about 0.1 to 12 hours, preferably about 1 to 4 hours, and more preferably about 2 hours.

The heating temperature in step (2) is preferably about 400 to 650° C., more preferably 450 to 600° C., and particularly preferably about 550° C. The heating reduction time in step (2) is typically about 1 to 5 hours, preferably 2 to 4 hours, and more preferably about 3 hours. Step (2) may be carried out in the presence of hydrogen gas, and preferably in a mixed gas of hydrogen gas with an inert gas, such as nitrogen or argon. When such a mixed gas is used, the molar ratio of the inert gas to hydrogen gas may be typically in the range of about 0:100 to 99:1, preferably about 75:25 to 97:3, and more preferably about 97:3. The pressure of the mixed gas may be about 0.1 MPa.

The heating temperature in step (3) is preferably about 100 to 300° C., more preferably 150 to 250° C., and particularly preferably about 250° C. The heating time in step (3) is typically about 0.1 to 12 hours, preferably about 1 to 4 hours, and more preferably about 2 hours. Step (3) can be carried out in an atmosphere in the presence of oxygen gas, for example, in atmospheric air.

The heating step in step (1) may be carried out by heating a starting microorganism-derived ceramic material as mentioned above by using an electric furnace or the like. Prior to step (1), the microorganism-derived ceramic material obtained from nature may be dried. The drying method is not particularly limited and may be a known method, such as vacuum drying, drying by heating (about 100° C.), and lyophilization. The heating reduction step in step (2) may be carried out by heating the ceramic material obtained in step (1) in the presence of hydrogen gas in an electric furnace. For example, an electric furnace for hydrogen reduction may be used to perform the heating step in step (2). As a commercially available electric furnace for hydrogen reduction, for example, a tubular furnace produced by Koyo Lindberg Ltd. can be used.

An electric furnace as used in step (1) or the like can be used as a heating means in step (3).

When the magnetic ceramic material of the present invention is subjected to heat treatment, at least part of the iron atoms contained in the microorganism-derived ceramic material is converted to a structure such as $Fe_3O_4$ or $\gamma$-$Fe_2O_3$, which has ferrimagnetism. In the heating (firing) step in step (1), the microorganism-derived ceramic material produces $\alpha$-$Fe_2O_3$. $\alpha$-$Fe_2O_3$ (hematite) does not have magnetism, unlike $\gamma$-$Fe_2O_3$ (magnetite) and $Fe_3O_4$ (maghemite). $\alpha$-$Fe_2O_3$ obtained in step (1) is subjected to heating reduction in step (2) to convert $\alpha$-$Fe_2O_3$ to $Fe_3O_4$. Further, $Fe_3O_4$ is subjected to oxidation treatment in step (3) to convert $Fe_3O_4$ to $\gamma$-$Fe_2O_3$.

The heating reduction in step (2) is preferably carried out in a hydrogen gas atmosphere from which oxygen has been removed. The method for removing oxygen from a mixed gas containing hydrogen gas may be, for example, passage through an oxygen removal column. The oxygen removal column may be a commercially available product. For example, a Large Oxy-Trap produced by GL Sciences Inc. can be used.

Water is generated during the heating reduction in the presence of hydrogen gas in step (2). The heating reduction step is preferably carried out in an atmosphere from which water has been removed. The method for removing water from the mixed gas containing hydrogen gas may be, for example, placing a desiccant (for example, $P_2O_5$) before and after the sample in the heating step (2) to thereby perform a hydrogen reduction step while passing a hydrogen gas-containing mixed gas from which water has been removed.

Removal of a trace amount of oxygen in the hydrogen reduction gas and water generated by the reduction reaction by using methods as mentioned above can prevent surface oxidation that would otherwise occur upon cooling the ceramic material, and can convert iron oxide contained in the magnetic ceramic material into a single phase of $Fe_3O_4$ (according to X-ray diffraction (XRD) analysis; the same applies hereinafter).

The magnetic ceramic material of the present invention can be produced by a method comprising steps (1) and (2), or a method comprising steps (1) to (3).

The magnetic ceramic material of the present invention that has been subjected to the above heat treatment contains iron oxide. The magnetic ceramic material of the present invention has magnetism because at least one kind of iron oxide contained therein has magnetism. The kind of magnetic iron oxide is not particularly limited. Examples of magnetic iron oxides that can be contained in the magnetic ceramic material of the present invention include ferrimagnetic iron oxides such as $Fe_3O_4$ and $\gamma$-$Fe_2O_3$. The magnetic ceramic material of the present invention preferably contains at least one member selected from the group consisting of $Fe_3O_4$ and $\gamma$-$Fe_2O_3$.

The shape of the magnetic ceramic material of the present invention is generally similar to the shape of the microorganism-derived ceramic material used as the starting material. More specifically, the magnetic ceramic material of the present invention may be in the shape of a sheath, a spiral, a branched tube, a thread (including a thread aggregate such as a harp or a pie wedge), a short trunk, a capsule, a sphere, a microtube, a nanotube, a hollow string, a capsule, a string-like and sphere-like agglomerate, a string, or a rod. The size of the magnetic ceramic material of the present invention is typically about 0.1 to 3000 μm.

More specifically, for example, the ceramic material in the shape of a sheath, a spiral, a branched tube, a thread, or a short trunk typically has a diameter of about 0.1 to 5 μm and a length of about 5 to 3000 μm, preferably a diameter of about 0.3 to 3 μm and a length of about 5 to 1000 μm, and more preferably a diameter of about 0.5 to 2 μm and a length of 5 to 200 μm. The ceramic material in the shape of a capsule typically has a length of about 1.2 to 24 μm. Further, the spherical ceramic material has a diameter of about 0.1 to 1 μm. The microtubular ceramic material has a diameter of about 0.3 to 4 μm and a length of about 5 to 200 μm. The nanotubular ceramic material has a diameter of about 300 to 450 nm and a length of about 5 to 200 μm. The ceramic material in the shape of a hollow string has a length of about 3 to 10 μm. The ceramic material in the shape of a capsule has a major axis of about 1.5 to 7 μm and a minor axis of about 0.5 to 3 μm. The ceramic material in the form of a string has a length of about 0.5 to 5 μm. The ceramic material in the shape of a rod has a length of about 5 to 30 μm.

Whether the magnetic ceramic material of the present invention contains $Fe_3O_4$ or $\gamma$-$Fe_2O_3$ makes little difference in surface shape.

In the magnetic ceramic material of the present invention, when the microorganism-derived ceramic material contains silicon and phosphorus in addition to an iron atom, the ratio of the components is similar to that in the microorganism-derived ceramic material used as the starting material. More specifically, when the magnetic ceramic material of the present invention contains iron, silicon, and phosphorus, the element ratio of iron, silicon, and phosphorus by atomic % (at %) is typically 66-87:2-27:1-32, and preferably 70-77:16-27:1-9.

The components of the magnetic ceramic material of the present invention vary according to the components of the microorganism-derived ceramic material used as the starting material. As described above, for example, when a microorganism that can produce a ceramic material is cultured in an environment in the presence of a transition metal element, such as cobalt, nickel, or manganese, a rare earth element, such as neodymium, and the like, the resulting microorganism-derived ceramic material can contain a transition metal element and a rare earth element. The magnetic ceramic material of the present invention containing these elements can have magnetism derived from substances other than iron. The ceramic material may further contain a light element, such as sodium, magnesium, and aluminum.

When the magnetic ceramic material of the present invention contains silicon and phosphorus in addition to iron, $Fe_3O_4$ and $\gamma$-$Fe_2O_3$ contained in the magnetic ceramic material and silicon and phosphorus in the form of solids are not typically dissolved, and iron, silicon, and phosphorus are phase-separated from each other. When the magnetic ceramic material of the present invention contains silicon and phosphorus, the X-ray diffraction (XRD) pattern of the magnetic ceramic material shows no clear peaks attributable to silicon or phosphorus. Thus, silicon and phosphorus are considered to be in the form of an oxide of an amorphous structure.

The crystallite size of the magnetic ceramic material of the present invention is, for example, about 5 to 100 nm.

Further, when iron oxide contained in the magnetic ceramic material of the present invention is a single phase of $Fe_3O_4$, about 60% of the iron contained in the magnetic ceramic material is $Fe_3O_4$, and about 40% thereof is paramagnetic $Fe^{2+}$ and $Fe^{3+}$. In contrast, when iron oxide contained in the magnetic ceramic material of the present invention is a single phase of $\gamma$-$Fe_2O_3$, about 70% of the iron contained in the magnetic ceramic material is $\gamma$-$Fe_2O_3$, and about 30% thereof is paramagnetic $Fe^{2+}$ and $Fe^{3+}$.

As described in the Examples below, the composition of the amorphous phase can be calculated from the results of Mossbauer spectroscopy and the ratio of iron, silicon, and phosphorus in the microorganism-derived ceramic material used as the starting material, assuming that paramagnetic $Fe^{2+}$ and $Fe^{3+}$ are Fe components that constitute the amorphous phase. When the ratio of iron, silicon, and phosphorus in the composition is Fe:Si:P=66-87:2-27:1-32 as mentioned above and when iron oxide contained in the magnetic ceramic material of the present invention is a single phase of $Fe_3O_4$, the composition of the amorphous phase has a Fe:Si:P ratio of approximately 36-66:5-55:2-60. When iron oxide contained in the magnetic ceramic material of the present invention is a single phase of $\gamma$-$Fe_2O_3$, the composition of the amorphous phase has a Fe:Si:P ratio of approximately 39-69:4-51:2-56.

When the magnetic ceramic material of the present invention contains at least one member selected from the group consisting of $Fe_3O_4$ and $\gamma$-$Fe_2O_3$, the total amount of these magnetic iron oxides in the magnetic ceramic material is typically about 1 to 50 mass %, preferably about 30 to 50 mass %, and more preferably about 40 to 50 mass %.

When the magnetic ceramic material of the present invention contains $Fe_3O_4$, the magnetic ceramic material has a saturation magnetization of typically about 1 to 50 emu/g, preferably about 30 to 50 emu/g, and more preferably about 40 to 50 emu/g. The magnetic ceramic material typically has a coercivity of about 0 to 2500 e. Moreover, the magnetic ceramic material has a residual magnetization of about 0 to 20 emu/g. When iron oxide contained in the magnetic ceramic material of the present invention is a single phase of $Fe_3O_4$, the magnetic ceramic material typically has a saturation magnetization of about 50 emu/g.

When iron oxide contained in the magnetic ceramic material of the present invention contains $\gamma$-$Fe_2O_3$, the magnetic ceramic material has a saturation magnetization of typically about 1 to 40 emu/g, preferably about 25 to 40 emu/g, and more preferably about 30 to 40 emu/g. The magnetic ceramic material typically has a coercivity of about 0 to 600 e. The magnetic ceramic material has a residual magnetization of about 0 to 20 emu/g. When iron oxide contained in the magnetic ceramic material of the present invention is a single phase of $\gamma$-$Fe_2O_3$, the magnetic ceramic material typically has a saturation magnetization of about 40 emu/g.

Pure $Fe_3O_4$ and $\gamma$-$Fe_2O_3$ have a saturation magnetization of 98 emu/g and 81 emu/g, respectively. Accordingly, when the magnetic ceramic material of the present invention contains $Fe_3O_4$ or $\gamma Fe_2O_3$, magnetic iron oxide fine particles of $Fe_3O_4$ or $\gamma$-$Fe_2O_3$ account for about 1 to 50% of the magnetic ceramic material of the present invention, and the amorphous phase containing oxides of phosphorus, iron, and silicon accounts for about 25 to 49% thereof.

Organic Group

In the present invention, the compound containing an organic group in the molecule is not particularly limited, insofar as the compound has an organic group, and a group that can be bound to or adsorbed on an oxygen atom (for example, a hydroxyl-derived oxygen atom) bound to a Fe atom and/or a Si present on the surface of the ceramic material.

Examples of organic groups that can be contained in the compound include those having the following functional groups: a carboxyl group, a carboxylic acid ester group, an amide group, an imido group, a cyano group, an isocyano group, an aldehyde group, a ketone group, an imino group, an amino group, an azido group, a nitro group, a hydroxy group, an ether group, an epoxy group, an isocyanato group, an isothiocyanato group, alkyl groups, aryl groups, alkenyl groups, alkynyl groups, a thiol group, a sulfide group, a sulfonic acid group, a sulfonic acid ester group, a sulfoxide group, heterocyclic rings, halogen atoms, a silicon atom, a titanium atom, and a phosphorus atom.

In the ceramic material into which an organic group containing such a functional group has been introduced, a catalyst, etc., can be immobilized on the organic group to thereby produce a catalytic-organic-inorganic composite material as described below. The catalytic-organic-inorganic composite material, which can impart a catalytic function to the ceramic material surface of various shapes, can exhibit an excellent catalytic feature according to the structure.

The ceramic material used in the present invention can be bound to the compound containing an organic group as mentioned above, for example, via an oxygen atom (such as a hydroxyl-derived oxygen) bound to a Fe atom and/or a Si atom contained in the ceramic material and via an atom contained in the organic group, such as silicon, titanium, phosphorus, or aluminum. Accordingly, the oxygen atom bound to the Fe atom and/or the Si atom contained in the ceramic material is bound to one of silicon, titanium, aluminum, and phosphorus contained in the organic group to form an organic-inorganic composite material.

The chemically modified ceramic material containing such a bond can be obtained, for example, by reacting a ceramic material with a silane coupling agent, a titanate coupling agent, an aluminate coupling agent, a phosphorus coupling agent, or the like. More specifically, the ceramic material is surface-treated with a silane coupling agent or the like to react the surface of the ceramic material with the silane coupling agent or the like, thus introducing an organic group contained in the silane coupling agent or the like into the ceramic material.

Improvement in adhesion of organic-inorganic interfaces is known as one of the functions of a silane coupling agent. This is achieved by the following mechanism. A silane coupling agent is hydrolyzed to silanol, and the silanol is partially condensed to an oligomer. The oligomer is adsorbed on the inorganic surface by hydrogen bonding and dried, whereby a hydroxyl group is subjected to a dehydration-condensation reaction to form a chemical bond, which firmly bonds an inorganic material and an organic material.

Silane coupling agents are known to have numerous kinds of organic groups and functional groups. Accordingly, such silane coupling agents are particularly excellent as reagents for introducing an organic group into the ceramic material. In the present invention, known silane coupling agents can be used. Commercial products are readily available. Examples of preferable silane coupling agents include compounds represented by the following general formula (1):

$$Y-R^1-Si(R^2)_n(R^3)_{3-n} \quad (1)$$

In formula (1), Y represents $R^4R^5N-$, $R^7R^8N-R^6-NR^4-$, $R^{11}R^{10}N-R^9-R^7N-R^6-NR^4-$, an alkyl group (preferably a $C_{1-6}$ alkyl group), a phenyl group, a 3,4-epoxycyclohexyl group, a halogen atom, a mercapto group, an isocyanate group, an optionally substituted glycidyl group, a glycidoxy group, an optionally substituted vinyl group, a methacryloxy group ($CH_2=C(CH_3)COO-$), an acryloxy group ($CH_2=CHCOO-$), a ureido group ($NH_2CONH-$), an optionally substituted methacryl group, an optionally substituted epoxy group, an optionally substituted phosphonium halide group, an optionally substituted ammonium halide group, or an optionally substituted acryl group, or Y and $R^1$ ($Y-R^1$) conjointly represent a vinyl group. Examples of the substituents include $C_{1-6}$ (preferably $C_{1-3}$) alkyl groups, halogen atoms (preferably chlorine, fluorine, and bromine, and more preferably chlorine), a phenyl group, and the like.

$R^4$, $R^5$, $R^7$, $R^8$, $R^{10}$, and $R^{11}$ each independently represent a hydrogen atom or a $O_{1-6}$ alkyl group, and $R^6$ and $R^9$ each independently represent an alkylene group having 2 to 6 carbon atoms.

In formula (1), $R^1$ represents a single bond, an alkylene group (preferably a $C_{1-6}$ alkylene group), or a phenylene group, or $R^1$ and Y ($Y-R^1$) conjointly represent a vinyl group. $R^1$ is preferably a $C_{2-4}$ alkylene group, and more preferably $C_3H_6$.

Each $R^2$ independently represents an alkyl group (preferably a $C_{1-6}$ alkyl group) or a phenyl group. $R^2$ is preferably a methyl group or a phenyl group, and more preferably a methyl group.

Each $R^3$ independently represents a hydroxy group or an alkoxy group (preferably a $C_{1-6}$ alkoxy group). $R^3$ is preferably a $C_{1-3}$ alkoxy group (including $\beta$-methoxyethoxy), and is more preferably a methoxy group or an ethoxy group.

The phosphonium moiety of the optionally substituted phosphonium halide group is preferably represented by the formula $P^+R^{14}R^{15}R^{16}-$ (wherein two of $R^{14}$ to $R^{16}$ are phenyl groups, and one of them is an alkyl group (preferably a $C_{1-8}$ alkyl group); or all of $R^{14}$ to $R^{16}$ are phenyl groups (optionally substituted in the 4-position by fluorine or methyl). The alkyl group is preferably isopropyl, n-butyl, isobutyl, cyclohexyl, or n-octyl. The optionally substituted phosphonium halide group is preferably a triphenylphosphonium bromide group.

The ammonium moiety of the optionally substituted ammonium halide group is represented by the formula $N^+R^{17}R^{18}R^{19}-$ (wherein each of $R^{17}$ to $R^{19}$ is an alkyl group or an aryl group, and preferably a $C_{1-8}$ alkyl group or a phenyl group), and the aryl group and the phenyl group may be substituted with 1 to 4 atoms or groups selected from halogen atoms, hydroxy, $C_{1-6}$ alkyl groups, $C_{1-6}$ alkoxy groups, cyano, nitro, and amino. Examples of alkyl groups preferably used include methyl, ethyl, isopropyl, n-butyl, isobutyl, cyclohexyl, n-octyl, and the like. The optionally substituted ammonium halide group is preferably an ammonium bromide group.

n is an integer of 0 to 2, preferably, 0 or 1, and more preferably 0.

Examples of silane coupling agents represented by formula (1) include the following compounds:

silane coupling agents having a vinyl functional group such as vinyltrimethoxysilane, vinyltriethoxysilane, vinyltris(β-methoxyethoxy)silane, and p-styryltrimethoxysilane;

silane coupling agents having a methacryloxy functional group such as 3-methacryloxypropyltrimethoxysilane, 3-methacryloxypropyltriethoxysilane, 3-methacryloxypropylmethyldimethoxysilane, and 3-methacryloxypropylmethyldiethoxysilane;

silane coupling agents having an acryloxy functional group such as 3-acryloxypropyltrimethoxysilane, 3-acryloxypropyltriethoxysilane, 3-acryloxypropylmethyldimethoxysilane, and 3-acryloxypropylmethyldimethoxysilane;

silane coupling agents having an amino functional group such as 3-aminopropyltrimethoxysilane, 3-aminopropyltriethoxysilane, 3-aminopropylmethyldimethoxysilane, 3-aminopropylmethyldiethoxysilane, N-phenyl-3-aminopropyltrimethoxysilane, N-phenyl-3-aminopropyltriethoxysilane, N-phenyl-3-aminopropylmethyldimethoxysilane, N-phenyl-3-aminopropyldiethoxysilane, N-methyl-3-aminopropyltrimethoxysilane, N-methyl-3-aminopropyltriethoxysilane, N-methyl-3-aminopropylmethyldimethoxysilane, N-methyl-3-aminopropylmethyldiethoxysilane, N,N'-dimethyl-3-aminopropylmethyltrimethoxysilane, N,N'-dimethyl-3-aminopropylmethyltriethoxysilane, N,N'-dimethyl-3-aminopropylmethyldimethoxysilane, N,N'-dimethyl-3-aminopropylmethyldiethoxysilane, 2-aminoethyl-3-aminopropyltrimethoxysilane, 2-aminoethyl-3-aminopropyltriethoxysilane, 2-aminoethyl-3-aminopropylmethyldimethoxysilane, 2-aminoethyl-3-aminopropylmethyldiethoxysilane, (N-methyl-2-aminoethyl)-3-aminopropyltrimethoxysilane, (N-methyl-2-aminoethyl)-3-aminopropyltriethoxysilane, (N-methyl-2-aminoethyl)-3-aminopropylmethyldiethoxysilane, (N-methyl-2-aminoethyl)-3-aminopropylmethyldimethoxysilane, (N,N'-dimethyl-2-aminoethyl)-3-aminopropyltrimethoxysilane, (N,N'-dimethyl-2-aminoethyl)-3-aminopropyltriethoxysilane, (N,N'-dimethyl-2-aminoethyl)-3-aminopropylmethyldiethoxysilane, (N,N'-dimethyl-2-aminoethyl)-3-aminopropylmethyldimethoxysilane, 2-aminoethyltrimethoxysilane, 2-aminoethyltriethoxysilane, 2-aminoethylmethyldimethoxysilane, 2-aminoethylmethyldiethoxysilane, 4-aminobutyltrimethoxysilane, 4-aminobutyltriethoxysilane, 4-aminobutylmethyldimethoxysilane, 4-aminobutylmethyldiethoxysilane, 6-aminohexyltrimethoxysilane, 6-aminohexyltriethoxysilane, 6-aminohexylmethyldimethoxysilane, 6-aminohexylmethyldiethoxysilane, 8-aminooctyltrimethoxysilane, 8-aminooctyltriethoxysilane, 8-aminooctylmethyldimethoxysilane, 8-aminooctylmethyldiethoxysilane, 4-aminophenyltrimethoxysilane, 4-aminophenyltriethoxysilane, 4-aminophenylmethyldimethoxysilane, 4-aminophenylmethyldiethoxysilane, 3-[2-(2-aminoethylamino)ethylamino]propyltrimethoxysilane, 3-[2-(2-aminoethylamino)ethylamino]propyltriethoxysilane, 3-[2-(2-aminoethylamino)ethylamino]propylmethyldimethoxysilane, 3-[2-(2-aminoethylamino)ethylamino]propylmethyldiethoxysilane, 3-ureidopropyltrimethoxysilane, 3-ureidopropyltriethoxysilane, 3-ureidopropylmethyldimethoxysilane, 3-ureidopropylmethyldiethoxysilane, 3-triethoxysilyl-N-(1,3-dimethylbutylidene)propylamine, and 3-trimethoxysilyl-N-(1,3-dimethylbutylidene)propylamine;

silane coupling agents having a silicon atom bound to a halogen-substituted alkyl group, such as 3-chloropropyltrimethoxysilane, 3-chloropropyltriethoxysilane, 3-chloropropylmethyldimethoxysilane, and 3-chloropropylmethyldiethoxysilane;

silane coupling agents having a mercapto functional group, such as 3-mercaptopropyltrimethoxysilane, 3-mercaptopropyltriethoxysilane, 3-mercaptopropylmethyldimethoxysilane, 3-mercaptopropylmethyldimethoxysilane, 3-mercaptoethyltrimethoxysilane, 3-mercaptoethyltriethoxysilane, 3-mercaptoethylmethyldimethoxysilane, and 3-mercaptoethylmethyldimethoxysilane;

sulfide silane coupling agents, such as bis(triethoxysilylpropyl)tetrasulfide and bis(trimethoxysilylpropyl)tetrasulfide;

silane coupling agents having an isocyanate functional group, such as 3-isocyanatepropyltrimethoxysilane, 3-isocyanatepropyltriethoxysilane, 3-isocyanatepropylmethyldimethoxysilane, and 3-isocyanatepropylmethyldiethoxysilane; and other silane coupling agents, such as 3-glycidoxypropyltrimethoxysilane, phenyltrimethoxysilane, n-octadecyltriethoxysilane, 3-(triethoxysilyl)propyltriphenylphosphonium bromide, and 3-(triethoxysilyl)propylammonium bromide.

Among these, silane coupling agents having an amino group, a mercapto group, a methacryloxy group, an epoxy group, or a halogen atom are preferable, when the organic-inorganic composite material of the present invention is further chemically modified as described below.

Specific examples of such preferable silane coupling agents include 3-aminopropyltrimethoxysilane, 3-aminopropyltriethoxysilane, 3-aminopropylmethyldimethoxysilane, 3-aminopropylmethyldiethoxysilane, 2-aminoethyl-3-aminopropyltrimethoxysilane, 2-aminoethyl-3-aminopropyltriethoxysilane, 2-aminoethyl-3-aminopropylmethyldimethoxysilane, 2-aminoethyl-3-aminopropylmethyldiethoxysilane, 3-[2-(2-aminoethylamino)ethylamino]propyl-trimethoxysilane, 3-[2-(2-aminoethylamino)ethylamino]propyl-triethoxysilane, 3-methacryloxypropyltrimethoxysilane, 3-mercaptopropyltrimethoxysilane, 3-chloropropyltriethoxysilane, 3-glycidoxypropyltrimethoxysilane, phenyltrimethoxysilane, n-octadecyltriethoxysilane, and the like.

Examples of silane coupling agents further include compounds represented by the formula (2):

$$R^{12}_3Si-NH_mR^{13}_{2-m} \qquad (2)$$

In formula (2), each $R^{12}$ independently represents an alkyl group (preferably a $C_{1-6}$ alkyl group). Preferably, $R^{12}$ is a $C_{1-6}$ linear alkyl group, and more preferably a $C_{1-3}$ linear alkyl group.

Each $R^{13}$ independently represents an alkyl group or an alkylsilane group (wherein the alkyl moiety in the alkyl group or alkylsilane group preferably contains 1 to 6 carbon atoms). Ru is preferably a trialkylsilane group. The alkyl group of the trialkylsilane group typically contains 1 to 6 carbon atoms, and preferably 1 to 3 carbon atoms.

In formula (2), m is an integer of 0 to 2, and preferably 1.

Specific examples of silane coupling agents represented by formula (2) include hexamethyldisilazane and the like.

Other examples of usable silane coupling agents, which, however, do not correspond to compounds represented by formula (1) or (2), include the following: bis(triethoxysilylpropyl)tetrasulfide $((C_2H_5O)_3SiC_3H_6S_4C_3H_6Si(OC_2H_5)_3)$, bis(trimethoxysilylpropyl)tetrasulfide $((CH_3O)_3SiC_3H_6S_4C_3H_6Si(OCH_3)_3)$, 3-triethoxysilyl-N-(1,3-dimethylbutylidene)propylamine $(C_2H_5O)_3SiC_3H_6N=C(CH_3)$ $C_4H_9)$, and 3-triethoxysilyl-N-(1,3-dimethylbutylidene)propylamine $(CH_3O)_3SiC_3H_6N=C(CH_3)$ $C_4H_9)$.

In the present invention, such silane coupling agents may be used singly or in a combination of two or more.

Examples of usable titanate coupling agents include known titanate coupling agents. Titanate coupling agents are known to contain numerous kinds of organic groups and thus can be suitably used as reagents for introducing an organic group into the ceramic material.

Examples of preferable titanate coupling agents include compounds represented by the formula (3):

$$Y-R^1-Ti(R^2)_n(R^3)_{3-n} \quad (3)$$

In formula (3), Y, $R^1$, $R^2$, $R^3$, and n are the same as defined in the silane coupling agents represented by formula (1).

Specific examples of titanate coupling agents include the following compounds: 3-aminopropyltriethoxytitanium, 3-methacryloxypropyltrimethoxytitanium, 3-mercaptopropyltrimethoxytitanium, 3-chloropropyltriethoxytitanium, 3-glycidoxypropyltrimethoxytitanium, phenyltrimethoxytitanium, n-octadecyltriethoxytitanium, isopropyl triisostearoyl titanate, isopropyltridodecylbenzenesulphonyl titanate, isopropyltris(dioctylpyrophosphate)titanate, tetraisopropylbis(dioctylphosphite)titanate, tetraoctylbis(ditridecylphosphite)titanate, tetra(2,2-diallyloxymethyl-1-butyl)bis(ditridecyl)phosphite titanate, bis(dioctylpyrophosphate)oxyacetate titanate, bis(dioctylpyrophosphate)ethylene titanate, isopropyl tri(dioctylphosphate) titanate, isopropyl tricumylphenyl titanate, isopropyl tri(N-amideethyl aminoethyl) titanate, and the like.

Among these, 3-aminopropyltrimethoxytitanium, 3-methacryloxypropyl trimethoxy titanium, 3-mercaptopropyl trimethoxy titanium, 3-mercaptopropyltrimethoxytitanium, 3-chloropropyltriethoxytitanium, 3-glycidoxypropyltrimethoxytitanium, and phenyltrimethoxytitanium, n-octadecyl triethoxy titanium are preferable.

In the present invention, such titanate coupling agents may be used singly or in a combination of two or more.

Examples of usable aluminate coupling agents include known aluminate coupling agents. Aluminate coupling agents are known to contain numerous kinds of organic groups and thus can be suitably used as reagents for introducing an organic group into the ceramic material. Examples of such aluminate coupling agents include acetoalkoxy aluminum diisopropylate, aluminum diisopropoxy monoethyl acetoacetate, aluminum trisethyl acetoacetate, aluminum trisacetylacetonate, and the like.

In the present invention, such aluminate coupling agents can be used singly or in a combination of two or more.

Examples of usable phosphorus coupling agents include known phosphorus coupling agents. Phosphorus coupling agents are known to contain numerous kinds of organic groups and thus can be suitably used as reagents for introducing an organic group into the ceramic material. Examples of phosphorus coupling agents include acryloyloxy ethylphthal oxyethyl diethyl phosphate, di(methacryloyloxy ethylphthal oxyethyl)diethyl pyrophosphate, di(methacryloyloxy ethylphthal oxyethyl)methyl phosphite, di(methacryloyloxy ethylphthal oxyethyl)phosphate, di(acryloyloxy ethylphthal oxyethyl)pyrophosphate, di(methacryloyloxy ethylphthal oxyethyl)phosphite, methacryloyloxyethyl maleoxyethyldiethyl phosphate, di(acryloyloxyethyl maleoxyethyl)diethyl pyrophosphate, di(methacryloyloxyethyl maleoxyethyl) ethyl phosphite, di(acryloyloxyethyl maleoxyethyl)phosphate, di(methacryloyloxyethyl maleoxyethyl)pyrophosphate, di(acryloyloxyethyl maleoxyethyl)phosphite, methacryloyloxyethyl succineoxy ethyldiethyl phosphate, di(methacryloyloxyethyl succinoxyethyl)dimethylpyrophosphate, di(methacryloyloxy ethylsuccinoxyethyl)ethyl phosphite, di(methacryloyloxyethyl succinoxyethyl)phosphate, di(methacryloyloxyethyl succinoxyethyl)pyrophosphate, di(methacryloyloxyethyl succinoxyethyl)phosphite, di(N-acrylaminomethyl)phosphite, di(N-acrylaminomethyl)pyrophosphate, di(N-acrylaminomethyl) phosphate, and the like.

In the present invention, such phosphorus coupling agents may be used singly or in a combination of two or more.

The definitions of terms used herein are set forth below.

The alkyl group or alkyl moiety may be a linear, branched or cyclic alkyl group. The alkylene group may be a linear, branched, or cyclic alkylene group.

The alkyl moiety refers to an alkyl group in the alkoxy group or alkylsilane.

The halogen atom refers to fluorine, chlorine, bromine, and iodine.

The $C_{1-8}$ alkyl group may be linear, branched, or cyclic. Examples thereof include methyl, ethyl, n-propyl, isopropyl, n-butyl, isobutyl, tert-butyl, n-pentyl, isopentyl, hexyl, heptyl, and octyl.

The $C_{1-6}$ alkyl group may be linear, branched, or cyclic. Examples thereof include methyl, ethyl, n-propyl, isopropyl, n-butyl, isobutyl, tert-butyl, n-pentyl, and isopentyl, and hexyl.

The alkyl group may be linear or branched. Examples thereof include methyl, ethyl, n-propyl, and isopropyl.

The $C_{1-6}$ alkylene group may be linear, branched, or cyclic. Examples thereof include methylene, ethylene, n-propylene, isopropylene, n-butylene, isobutylene, tert-butylene, n-pentylene, isopentylene, and hexylene.

The $C_{2-6}$ alkylene group may be linear, branched, or cyclic. Examples thereof include ethylene, n-propylene, isopropylene, n-butylene, isobutylene, tert-butylene, n-pentylene, isopentylene, and hexylene.

The $C_{2-4}$ alkylene group may be linear, branched, or cyclic. Examples thereof include ethylene, n-propylene, isopropylene, n-butylene, isobutylene, and tert-butylene.

The $C_{1-6}$ alkoxy group may be linear, branched, or cyclic. Examples thereof include methoxy, ethoxy, propoxy, isopropoxy, butoxy, isobutoxy, tert-butoxy, pentyloxy, isopentyloxy, hexyloxy, and β-methoxyethoxy.

The $C_{1-3}$ alkoxy group may be linear or branched. Examples thereof include methoxy, ethoxy, propoxy, isopropoxy, and β-methoxyethoxy.

The aryl group refers to a monocyclic or polycyclic group comprising a 5- or 6-membered aromatic hydrocarbon ring. Examples thereof include phenyl, naphthyl, fluorenyl, anthryl, biphenylyl, tetrahydronaphthyl, and chromanyl.

The organic-inorganic composite material of the present invention can be obtained by reacting a ceramic material as mentioned above with a compound containing an organic group as mentioned above. For example, when one of the various coupling agents as mentioned above is used as the compound having an organic group, an organic-inorganic composite material of the present invention can be produced by mixing the ceramic material with such a coupling agent in a suitable solvent.

Examples of usable solvents include diethyl ether, tetrahydrofuran, dioxane, and like ethers, acetonitrile, dimethylformamide, dimethyl sulfoxide, toluene, and the like. The amount of solvent is not particularly limited and can be suitably selected.

The reaction temperature may be about −30 to 200° C., and the reaction time may be suitably selected from the range of about 30 minutes to 200 hours. The chemically modified ceramic material obtained as a reaction product can be isolated by usual separation means, such as filtration and centrifugation.

The loading of the organic group in the organic-inorganic composite material of the present invention may vary according to the kinds of ceramic material and organic group-containing compound (e.g., silane coupling agent) used, reaction conditions, etc. The amount of the organic group in the organic-inorganic composite material is typically about 1 to 30 wt. %, and preferably 5 to 20 wt. %. In the present invention, the loading is determined by elemental analysis.

When the organic-inorganic composite material of the present invention has a structure such that a phosphonium halide alkylsilyl group or an ammonium halide alkylsilyl group is bound to an oxygen atom bound to a Fe atom and/or a Si atom contained in the ceramic material, the organic-inorganic composite material can be used as a catalyst for the reaction of synthesizing an alkylene carbonate, such as ethylene carbonate or propylene carbonate, from carbon dioxide and alkylene oxide, such as ethylene oxide or propylene oxide (see, for example, Japanese Unexamined Patent Publication No. 2008-296066). The organic-inorganic composite material wherein a phosphonium halide alkylsilyl group or an ammonium halide alkylsilyl group is bound to an oxygen atom bound to a Fe atom and/or Si atom contained in the ceramic material can be produced by reacting the ceramic material with phosphonium halide alkyltrialkoxysilane or ammonium halide alkyltrialkoxysilane, which are silane coupling agents represented by formula (1). The reaction temperature for this reaction is typically 0 to 200° C., and preferably 30 to 150° C. The phosphonium halide moiety and the ammonium halide moiety correspond to the optionally substituted phosphonium halide group and the optionally substituted ammonium halide group mentioned above, respectively. The content of phosphonium halide alkyltrialkoxysilane or ammonium halide alkyltrialkoxysilane in the organic-inorganic composite material is typically 1 to 20 wt. %, and preferably 5 to 20 wt. %.

In the present invention, after an organic group has been introduced into the ceramic material using a coupling agent as mentioned above, etc., the organic-inorganic composite material may be further chemically modified by utilizing a functional group contained in the organic group. Such a chemical modification can be performed, for example, by an amidation reaction by condensation of a carboxylic acid and an amine; an esterification reaction by condensation of a carboxylic acid and an alcohol; a nucleophilic addition reaction of an amine, an alcohol, etc., to epoxide; a nucleophilic substitution reaction of an amine, an alcohol, a thiol, etc., to an organic halogen compound; a Michael addition reaction of an amine, thiol, etc., to an α,β-unsaturated carbonyl group; an imine formation reaction by dehydration condensation of an amino group and an aldehyde group; a carbon-carbon bonding formation reaction using an organometallic reagent, such as Grignard reaction or Wittig reaction; and a metal complex catalyst carbon-carbon bonding formation reaction, such as Suzuki-Miyaura coupling reaction or olefin metathesis. Further chemical modification by such a reaction can also convert the functional group contained in a silane coupling agent or the like to a desired functional group.

Immobilization of the Catalyst

In the present invention, a catalyst can be immobilized on an organic-inorganic composite material by utilizing a functional group contained in an organic group of the organic-inorganic composite material of the present invention or a functional group introduced by further chemical modification as mentioned above. In the present invention, the material produced by immobilizing a catalyst on the organic-inorganic composite material may be referred to as "catalytic-organic-inorganic composite material". When a catalyst is immobilized on the organic-inorganic composite material of the present invention, the catalyst is present on at least a part of the surface of the ceramic material, whereby various catalytic properties can be imparted to the organic-inorganic composite material according to the shape of the ceramic material.

Examples of the catalyst immobilized on the organic-inorganic composite material of the present invention include enzymes, organic catalysts, metal complex catalysts, and the like. These catalysts can be immobilized singly or in a combination of two or more.

Examples of usable enzymes include known enzymes. Examples of enzymes that can be preferably used in the present invention include hydrolases, oxidoreductases, transferases, lyases, isomerases, ligases, and the like.

Examples of hydrolases include esterases that hydrolyze an ester; proteases that hydrolyze a peptide bond, such as lipase, pepsin, chymotrypsin, carboxypeptidase, thermolysin, cathepsin, peptidase, aminopeptidase, papain, chymopapain, bromelain, protease, hydroxynitrile lyase, proteinase, and dipeptidase; glucosidases that hydrolyze a glucosidic bond of a sugar, such as α-glucosidase, β-glucosidase, α-glucanase, β-glucanase, α-galactosidase, β-galactosidase, α-amylase, β-amylase, cellulase, and pullulanase; phosphatases that hydrolyze a phosphate bond, such as phosphomonoesterase, phosphodiesterase, and pyrophosphatase; amidases that hydrolyze an amide group, such as arginase, urease, and glutaminase; and other hydrolases such as nuclease, lactonase, collagenase, nitrile hydratase, and hydroxynitrile lyase; and the like.

Examples of oxidoreductases include alcohol dehydrogenase, lactate dehydrogenase, glucose oxidase, cholesterol oxidase, amine oxidase, glucose dehydrogenase, aldehyde oxidase, pyruvate dehydrogenase, pyruvate synthase, succinate dehydrogenase, glutamate dehydrogenase, cytochrome c oxidase, catalase, peroxidase, ferredoxin hydrogenase, superoxide dismutase, cytochrome P450, and the like.

Examples of transferases include transphosphorylase, transglucosidase, transpeptidase, transamidase, transglutaminase, transaldolase, transketolase, phosphorylase, creatine kinase, hexokinase, pyruvate kinase, phosphoglycerate kinase, RNA polymerase, DNA polymerase, glucosamine transacetylase, aminoacyltransferase, aspartate transaminase, alanine transaminase, 6-phosphofructokinase, and the like.

Examples of lyases include pyruvate decarboxylase, histidine decarboxylase, aldolase, citrate (si)-synthase, ATP citrate (pro-3S)-lyase, tryptophanase, fumarate hydratase, aconitate hydratase, enolase, Enoyl-CoA hydratase, aspartate ammonia-lyase, and the like.

Examples of isomerases include ribulose-phosphate 3-epimerase, UDP-glucose 4-epimerase, triosephosphate isomerase, glucose phosphate isomerase, phosphoglycerate phosphomutase, and the like.

Examples of synthases include tyrosyl-tRNA synthetase, acyl-CoA synthetase, amide synthetase, peptide synthetase, cyclo-ligase, acetyl-CoA carboxylase, and the like.

Other examples of usable enzymes include aldolase, Baeyer-Villiger monooxygenase, alcohol dehydrogenase, carbonyl reductase, and the like.

Among these enzymes, lipase, carbonyl reductase, and the like are preferable in the present invention.

The source of such enzymes may be of animal, plant, or microbial origin. Purified enzymes are preferable, but crude products may also be used.

The organic-inorganic composite material of the present invention is particularly excellent as a carrier for enzymes. The enzyme organic-inorganic composite material having an enzyme immobilized thereon has a high enzyme loading and can exhibit excellent catalytic functions. For example, lipase, which is an oil and fat hydrolase, can catalyze an esterification reaction and a transesterification reaction in organic solvents as well as hydrolysis of ester bonds. In the present invention, the enzyme organic-inorganic composite material having an enzyme lipase immobilized thereon exhibits excellent properties in kinetic optical resolution of racemic compounds, and thus can find a wide variety of applications in the organic synthesis field and the field of pharmaceuticals. When a kinetic optical resolution reaction of a racemic compound is performed using an immobilized enzyme catalyst comprising a lipase-immobilized enzyme organic-inorganic composite material, the reaction temperature is typically 0 to 100° C., and preferably 20 to 60° C.

The immobilized enzyme catalyst comprising the enzyme organic-inorganic composite material of the present invention can be maintained for a long period of time and can maintain enzymatic activity even after repeated use, thus exhibiting excellent properties. Accordingly, the expensive enzyme is not disposed of but can be repeatedly used. Furthermore, because the enzyme does not remain in the reaction product, it can be used as an industrially advantageous immobilized enzyme.

The enzyme can be loaded on the organic-inorganic composite material of the present invention by a usual immobilization method. For example, it can be easily done by mixing the organic-inorganic composite material and an enzyme in a solvent, such as a phosphate buffer.

The amount of enzyme in the immobilized enzyme catalyst comprising the enzyme-organic-inorganic composite material of the present invention may vary according to the enzyme and organic-inorganic complex material used. The amount of enzyme in the enzyme organic-inorganic composite material may be typically about 1 to 10 wt. %, and preferably about 3 to 5 wt. %. In the present invention, the amount of enzyme is determined by the Bradford method.

When the catalyst in the immobilized catalyst comprising the catalytic-organic-inorganic composite material of the present invention is an enzyme, the enzyme and a functional group present in an organic group of the organic-inorganic composite material are immobilized by a non-covalent bond (intermolecular interaction), such as a hydrogen bond, adsorption, or the like. Alternatively, the enzyme may be physically incorporated and immobilized by a sol-gel process or using calcium alginate.

The organic catalyst contains no metal elements and is a catalytic compound that comprises elements such as carbon, hydrogen, oxygen, nitrogen, sulfur, phosphorus, fluorine, chlorine, bromine, iodine, and the like. In the present invention, an organic catalyst can be introduced by utilizing a functional group present in an organic group of the organic-inorganic composite material. Alternatively, after a trialkoxysilyl group, i.e., a part of a silane coupling agent, is bound to an organic catalyst, the resulting catalyst can be reacted with the ceramic material to introduce the organic catalyst. Examples of such organic catalysts include asymmetric organic catalysts, etc.

Examples of usable metal complex catalysts include known metal complex catalysts. In the present invention, a metal complex catalyst (including various organic metal catalysts and metal oxides) can be immobilized by a non-covalent bond (intermolecular interaction), a covalent bond, adsorption, a coordinate bond, etc., to a functional group that is present in an organic group of the organic-inorganic composite material. For example, when a ceramic material is reacted with a chelate silane coupling agent, such as 3-[2-(2-aminoethylaminoethylamino)propyl]trimethoxysilane to produce a chemically modified ceramic material, a transition metal such as Pt, Pd, Co, or Hg can be coordinated thereon. Alternatively, after a functional group is introduced into a phosphorus ligand and bound to a functional group that is present in an organic group of the organic-inorganic composite material, a transition metal such as Pt, Pd, Ru, and Rh can be coordinated thereon.

Immobilization of Dye

Further, a dye, etc., can be immobilized on the organic-inorganic composite material of the present invention by utilizing a functional group contained in an organic group of the organic-inorganic composite material or a functional group introduced by further chemical modification as mentioned above. Examples of dyes that can be immobilized include known dyes. Specific example thereof include porphin (non-metal), a central metal-substituted porphyrin, tetraphenylporphyrin, 5,10,15,20-tetraphenylporphyrin copper (II), 5,10,15,20-tetraphenylporphyrin zinc (II), 5,10,15,20-tetraphenylporphyrin cobalt (III) chloride, 5,10,15,20-tetraphenylporphyrin chromium (III) chloride, 5,10,15,20-tetraphenylporphyrin aluminum (III) chloride, 5,10,15,20-tetrakis(pentafluorophenyl)-21H,23H-porphin, 5-(4-carboxyphenyl)-10,15,20-triphenylporphyrin, silicon phthalocyanineoxide, aluminum phthalocyanine chloride, phthalocyanine (non-metal), central metal-substituted phthalocyanine, porphyrin-dilithium phthalocyanine, copper tetramethyl phthalocyanine, copper phthalocyanine, chromium phthalocyanine, zinc phthalocyanine, lead phthalocyanine, titanium phthalocyanineoxide, Mg phthalocyanine, copper octamethylphthalocyanine, and like porphyrin dyes.

EXAMPLES

Hereinafter, the present invention is described in further detail with reference to the Examples, etc. However, the present invention is not limited to these Examples.

1. Isolation and Purification of Microorganism-Derived Ceramic Material (1)

A turbid liquid containing biogenous iron oxide (a ceramic material in the shape of a sheath produced by *Leptothrix ochracea*) was collected from a water purification plant in Joyo City, Kyoto, placed in a 20-L tank, and allowed to stand to precipitate the biogenous iron oxide. Then, 10 L of the supernatant was removed by decantation, and 10 L of ion exchange water was added thereto to produce turbidity. The resulting product was allowed to stand for one day to precipitate the biogenous iron oxide. This precipitation procedure was repeated 5 times. The remaining turbid liquid was placed in a centrifuge tube (size: 800 mL), and an ultrasonic wave was applied thereto for 5 minutes. Thereafter, the biogenous iron oxide was precipitated by centrifugation (9,000 rpm, 10 minutes), and the supernatant was removed. This procedure was repeated, and when no more turbid liquid was left in the tank, the biogenous iron oxide was placed together in one centrifuge tube while being washed with ion exchange water. It should be kept in mind not to mix the sand accumulated at the bottom of the centrifuge tube at this time. After centrifugation, the supernatant was discarded. Subsequently, ethanol (about 2 L) was added to the biogenous iron oxide in the centrifuge tube, and the mixture was transferred to a pear-shaped flask and stirred for 1 hour. The ethanol was distilled off with an evaporator. When the residue was vacuum-dried, 75 g of the biogenous iron oxide (a reddish brown powder) was obtained. Elemental analysis resulted in C: 1.87% and N: 0.00%. According to the determination of EDX, the elemental ratio of Fe:Si:P in the biogenous iron oxide was 73:22:5. Non-Patent Literature 1 discloses other methods for characterizing biogenous iron oxide.

2. Isolation and Purification of Microorganism-Derived Ceramic Material (2)

In a manner similar to above, ceramic materials were isolated from sludge collected from a gutter at the main building of the Faculty of Engineering of Okayama University. It was confirmed that the sludge mainly contained a *Gallionella ferruginea*-derived ceramic material in the shape of a spiral. FIG. 1 shows an SEM photograph thereof.

According to the determination of EDX, the elemental ratio of Fe:Si:P in the obtained ceramic material was 77:18:5.

3. Isolation and Purification of Microorganism-Derived Ceramic Material (3)

(1) Isolation of OUMS1 Strain from Water Purification Plant in Joyo City, Kyoto

Water was collected from groundwater sediment contained in an iron bacteria tank in the Joyo City Cultural Center in Joyo City, Kyoto, and placed in a container. A small amount thereof (e.g., 0.5 to 1 g) was introduced into a JOP liquid medium (0.076 g of disodium hydrogenphosphate dodecahydrate, 0.02 g of potassium dihydrogenphosphate dihydrate, 2.383 g of HEPES, and 0.01 mM of iron sulfate, per liter of sterile groundwater, the pH being adjusted to 7.0 with an aqueous sodium hydroxide solution) containing iron chips (purity: 99.9%, about 5 mm square), and sufficiently suspended. Thereafter, the resulting product was cultured at 20° C. for 10 days in a shaking incubator (70 rpm). A portion of the sediment that increased during the culture was collected, transferred to a flask containing a fresh JOP liquid medium containing iron chips, and subjected to shaking culture for another 10 days under the same conditions. This process was repeated once again. A small amount of the liquid in the flask was collected and diluted with a JOP liquid medium to $10^{-2}$ to $10^{-6}$. Each diluted solution was separately added dropwise to a respective JOP agar plate medium in a sterile Petri dish and spread-plated onto each of the media with a sterile glass rod. When the media were cultured at 20° C. for 7 to 10 days in an incubator, the proliferation of the target bacteria and the formation of an oxide having a sheath shape were observed.

After the completion of the culture, the obtained single colony (strain) was individually picked up with a sterilized toothpick, inoculated into newly prepared JOP agar plate media, and cultured at 20° C. for 10 days. Colonies then appeared on the media. Among these colonies, an irregularly shaped colony of a light yellowish brown color was identified. Observation with a low-power optical microscope confirmed that the majority of the moiety of a light yellowish brown color was in the sheath structure. The isolated strain having such properties was designated as an OUMS1 strain.

Figure 2:
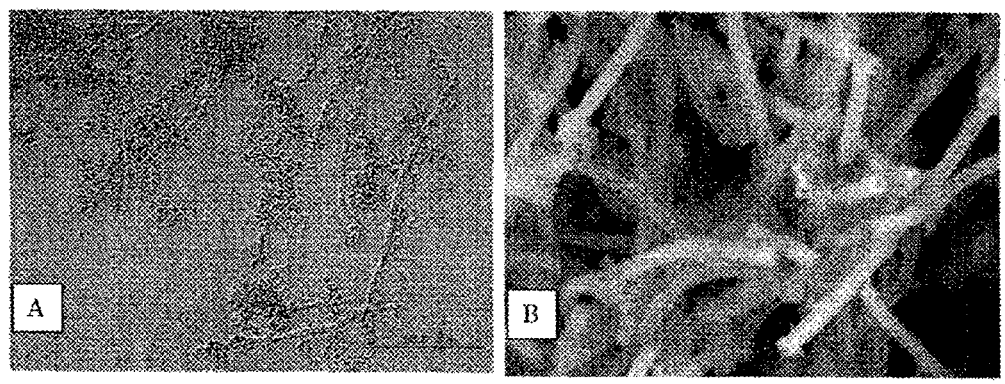
FIG. 2 shows an optical microscope image (A) and a scanning electron microscope (SEM) image (B) of the oxide in the shape of a sheath obtained after culture of OUMS1 strain in a JOP liquid medium.

A portion of the identified OUMS1 strain colony was scraped, transferred to a flask containing a newly prepared JOP liquid medium, and cultured at 20° C. for 10 days in a shaking incubator (70 rpm). Thereafter, the increased suspended material was placed on a slide glass and observed with an optical microscope and a scanning electron microscope. The formation of an oxide having a sheath shape was confirmed (FIGS. 2-A and 2-B).

(2) Identification of OUMS1 Strain Isolated from Water Purification Plant in Joyo City, Kyoto The OUMS1 strain was cultured on a JOP agar plate at 23° C. for 10 days. 1 mL of a TE buffer (10 mM Tris/1 mM EDTA) was added to the plate, and the cells were scraped with a cell scraper (produced by TRP) and collected into an Eppendorf tube. Thereafter, the cells were collected by centrifugation at 5,000 g for 10 min. The genomic DNA was extracted by the CTAB method, and the 16S rDNA region was amplified by PCR with the following primers.

```
5'-AGA GTT TGA TCM TGG CTC AG-3'

5'-GGY TAC CTT GTT ACG ACT T-3'
```

The amplified fragments were TA-cloned using a TA PCR cloning kit (BioDynamics Laboratory Inc.), and DNA sequencing was performed by the dideoxy method (Sanger method). The obtained DNA sequence was equal to the nucleotide sequence of SEQ ID NO: 1. A homology search was performed for the nucleotide sequence of 16S ribosomal DNA using BLAST from the DDBJ.

FIGS. 3-A and 3-B show the results of the homology search. The results showed 99% homology with the 16S ribosomal DNA nucleotide sequence (Reference 2) of a known iron-oxidizing bacteria *Leptothrix cholodnii* SP-6 strain (Reference 1).

Reference 1: Emerson, D. and Ghiorse, W. C. Isolation, Cultural Maintenance, and Taxonomy of a Sheath-Forming Strain of *Leptothrix discophora* and Characterization of Manganese-Oxidizing Activity Associated with the Sheath. Appl. Environ. Microbiol. 58, 4001-4010 (1992)

Reference 2: Spring, S., Kaempfer, P., Ludwig, W. and Schleifer, K. H. Polyphasic characterization of the genus *Leptothrix*: new descriptions of *Leptothrix mobilis* sp. nov. and *Leptothrix discophora* sp. nov. nom. rev. and amended description of *Leptothrix cholodnii* emend Syst. Appl. Microbiol. 19, 634-643 (1996)

The OUMS1 strain was cultured at 20° C. for 4 days in an MSVP (see, for example, Mulder, E. G., and W. L. van Veen Investigations on the *Sphaerotilus-Leptothrix* group. Ant, v. Leeuwhoek 29, 121-153 (1963)) liquid medium, and the proliferated bacterial cells were collected. Then, the genomic DNA was extracted by the CTAB method, and genomic DNA analysis was performed in accordance with the random amplified polymorphic DNA (RAPD) method, so as to make a comparison with the genomic DNA of a known iron-oxidizing bacteria *Leptothrix cholodnii* SP-6 strain. FIG. 4 shows the genomic DNA electrophoretic patterns of the OUMS1 strain and a known iron-oxidizing bacteria *Leptothrix cholodnii* SP-6 strain.

As shown in FIG. 4, in all six types of primers used, the OUMS1 genomic DNA electrophoretic patterns were different from those of known SP-6 in terms of the length and the number of the amplified fragments. This clarifies that the OUMS1 strain differs from SP-6.

A portion of the OUMS1 strain colonies was scraped, transferred to a flask containing an MSVP liquid medium (Reference 1) containing manganese sulfate in place of iron sulfate, and cultured at 20° C. for 10 days in a shaking incubator (70 rpm). Thereafter, the increased suspended material was placed on a slide glass and observed with an optical microscope. The formation of an oxide having a sheath shape was confirmed.

The OUMS1 strain is the same as a known iron-oxidizing bacteria *Leptothrix cholodnii* SP-6 strain in terms of the shape of the culture colonies, capability of forming a sheath-shaped oxide, and manganese oxidation capability. Further, because the results of the homology search for the 16S ribosomal DNA nucleotide sequence confirmed that the OUMS1 strain showed 99% homology with a known iron-oxidizing bacteria *Leptothrix cholodnii* SP-6 strain, the OUMS1 strain was identified as known iron-oxidizing bacteria *Leptothrix cholodnii*. In addition, because a comparison of the genomic DNA electrophoretic patterns by the RAPD method confirmed that the OUMS1 strain differs from a known iron-oxidizing bacteria *Leptothrix cholodnii* SP-6 strain, the OUMS1 strain was designated as *Leptothrix cholodnii* OUMS1 strain (NITE BP-860).

3. Properties of Iron Oxide Formed by OUMS1

The crystal structure of the iron oxide formed by the OUMS1 strain was measured using X-ray diffraction (XRD), its composition was analyzed by energy-dispersive X-ray (EDX) analysis, and the microstructural observation was evaluated with a scanning electron microscope (SEM) and a transmission electron microscope (TEM).

FIGS. 5-A-1 to 5-A-14 as well as 5-B-1 and 5-B-2 show SEM images of the iron oxide formed by the OUMS1 strain. It was clear that almost all the structures in sight had a tubular (microtubular) shape on the order of microns. The outer diameter of the structure was about 1.6 to 3.7 µm, and the internal diameter was about 0.5 to 0.8 µm. The surface shape of the iron oxide formed by the OUMS1 strain can roughly be classified into three shapes. Specifically, a surface shape such that fibrous particles (width of the fiber: about 100 to 200 nm) are sparsely aggregated as shown in FIGS. 5-A-1 to 5-A-6, a surface shape such that fibrous particles (the width of the fiber: about 100 to 300 nm) are densely aggregated as shown in FIGS. 5-A-7 to 5-A-11, and a surface shape comprising scaly particles as shown in FIGS. 5-A-12 to 5-A-14. In addition to these, an agglomerate as shown in FIG. 5-B-1, and a rod-shaped iron oxide having a thickness of about 1 µm shown in FIG. 5-B-2 were also observed.

Figure 7:
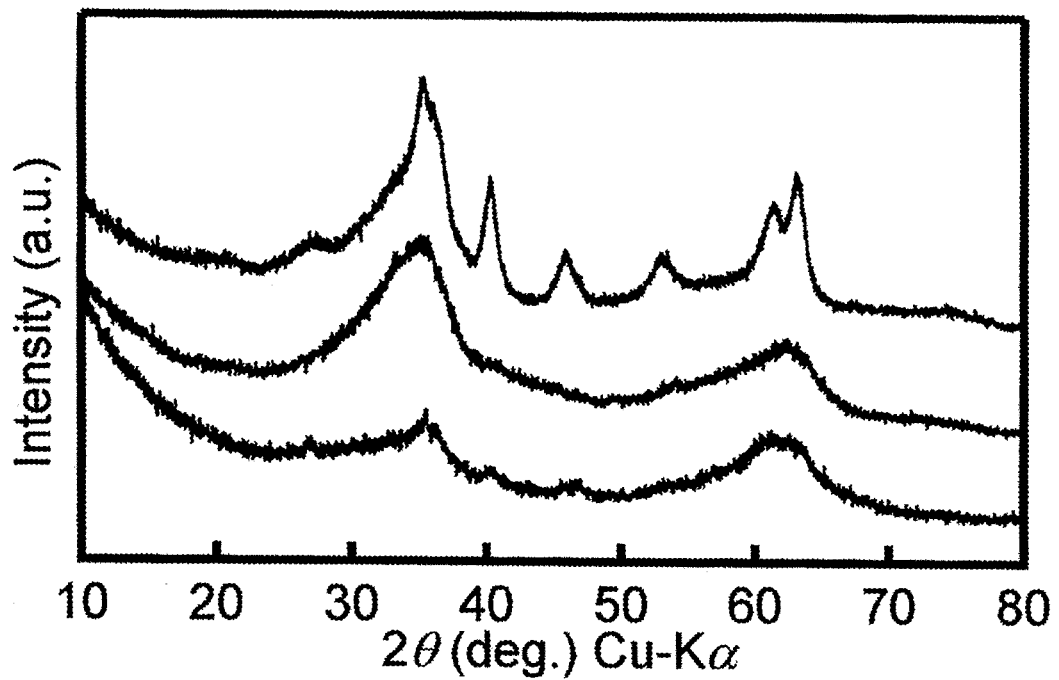
FIG. 7 shows an X-ray diffraction (XRD) pattern of the iron oxide formed by OUMS1 strain.

FIGS. 6-1 to 6-13 show TEM images of the iron oxide formed by the OUMS1. In addition to the shapes shown in FIGS. 6-1 to 6-4, which are similar to the microtubular shapes observed in the SEM images above, the following shapes were confirmed: a nanotubular shape having an outer diameter of about 350 to 400 nm as shown in FIGS. 6-5 and 6-6, a hollow string shape having an outer diameter of about 500 nm and an internal diameter of about 180 nm as shown in FIG. 6-7, a capsule shape having a major axis of about 1.5 to 5 µm and a minor axis of about 0.78 to 2.0 µm as shown in FIGS. 6-8 to 6-10, a tubular shape whose one end is closed, having an outer diameter of about 350 nm and an internal diameter of about 230 nm as shown in FIGS. 6-11, a shape of a string-like and sphere-like agglomerate as shown in FIG. 6-12, and a string-like iron oxide as shown in FIG. 6-13. These results clarified that the OUMS1 formed an iron oxide having various shapes, such as a nanotubular shape, a hollow string shape, a capsule shape, a shape of a string-like and sphere-like agglomerate, and a string-like shape, in addition to an iron oxide in the shape of a microtube.

As a result of the composition analysis by EDX, it was clear that the constituent components of the iron oxide formed by the OUMS1 were Fe, O, Si, and P. Table 1 shows the average values and the standard deviations of the results of the analysis performed for 24 points. The composition excluding oxygen was Fe:Si:P=79.3:8.8:11.9. This iron oxide also contains a carbon atom and a hydrogen atom.

TABLE 1

| | Analytical Points: 24 | | | |
|---|---|---|---|---|
| | Average | | Standard deviation | |
| Element | Wt % | at % | Wt % | at % |
| SiK | 4.9 | 8.8 | 1.5 | 2.8 |
| PK | 7.4 | 11.9 | 5.6 | 8.6 |
| FeK | 87.7 | 79.3 | 4.4 | 6.2 |

FIG. 7 shows an XRD pattern of the iron oxide formed by the OUMS1 strain (lowest), and, as comparison samples, XRD patterns of 2-line ferrihydrite (2nd from the lowest) and 6-line ferrihydrite (3rd from the lowest). The iron oxide formed by the OUMS1 strain shows peaks that appear to be a combination of the peaks of 2-line ferrihydrite and 6-line ferrihydrite. These results clarified that the iron oxide formed by the OUMS1 was ferrihydrite.

Figure 8:
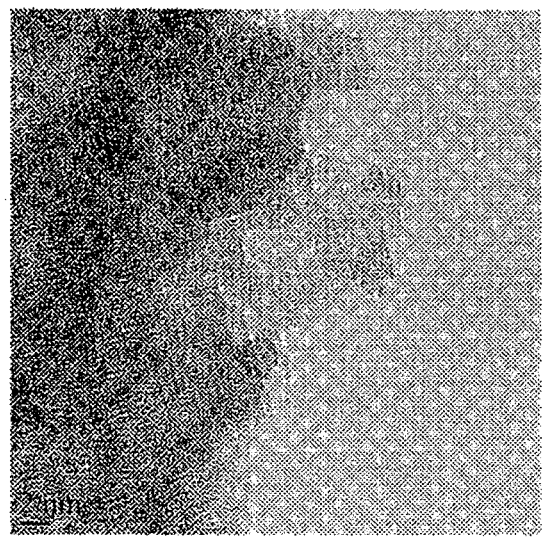
FIG. 8 shows a high-resolution TEM image of the iron oxide formed by OUMS1 strain.

FIG. 8 shows a high-resolution transmission electron microscope (HRTEM) image of a typical microtubular iron oxide formed by the OUMS1. This clarified that the iron oxide formed by the OUMS1 had a primary particle diameter of about 3 to 5 nm. Further, clear cross stripes were observed in the primary particles. This clarified that the iron oxide formed by the OUMS1 was a microcrystal aggregate.

The results of XRD measurement and HRTEM observation clarified that the iron oxide formed by the OUMS1 was an aggregate (a ceramic material) of ferrihydrite nanoparticles, the primary particle diameter thereof being about 3 to 5 nm.

Devices Used for Analysis

Optical microscope: Olympus, BX-51 (FIGS. 2-A and 4-A)
X-ray diffraction (XRD) measurement: Rigaku Corporation, RINT-2000 (FIG. 7)
Scanning electron microscope (SEM): Hitachi High-Technologies Corporation, Miniscope TM-1000 (FIGS. 2-B and 4-B)
Scanning electron microscope (SEM): JEOL Ltd., JSM-6700F (FIGS. 5-A and 5-B)
Energy Dispersive X-Ray (EDX) analysis: JEOL Ltd., JED-2200F (Table 1)
Transmission electron microscope (TEM): JEOL Ltd., JEM-2100F (FIGS. 6 and 8)

4. Chemical Modification of the Biogenous Iron Oxide Using Silane Coupling Agent (General Procedure)

The biogenous iron oxide (ceramic material) obtained in the isolation and purification of ceramic material (1) was dried at 150° C. for 4 hours under reduced pressure using a vacuum pump. The dried biogenous iron oxide (300 mg) was placed in a reactor, and the reactor was purged with nitrogen. The silane coupling agent (1.0 mmol) described in each Example and dry toluene (3 mL) were added thereto, followed by heating at 100° C. for 24 hours. Then, toluene was distilled off with an evaporator. Using ethyl acetate, the modified biogenous iron oxide was transferred to a centrifuge tube, and centrifugation was performed at 9,000 rpm for 10 minutes. Thereafter, the supernatant was removed. After this purification procedure was repeated 5 times, the precipitate of the modified biogenous iron oxide was vacuum-dried. The organic group loading was calculated by elemental analysis. It is notable that when solid-state NMR, such as $^{13}$C CP/MAS NMR or $^{29}$Si CP/MAS NMR, is measured, no NMR signals are observed, because the presence of paramagnetic iron makes the relaxation time very short. For this reason, the chemical modification can only be confirmed by elemental analysis and an infrared absorption spectrum, as well as, in particular cases, by an ultraviolet-visible absorption spectrum, a microscope observation, and an evaluation of catalyst activity expressed by a supporting catalyst.

Example 1

Chemical Modification of the Biogenous Iron Oxide Using 3-aminopropyltriethoxysilane In accordance with the above-described general procedure, the biogenous iron oxide was chemically modified using 3-aminopropyltriethoxysilane, as shown in the following formula.

[Chem. 1]

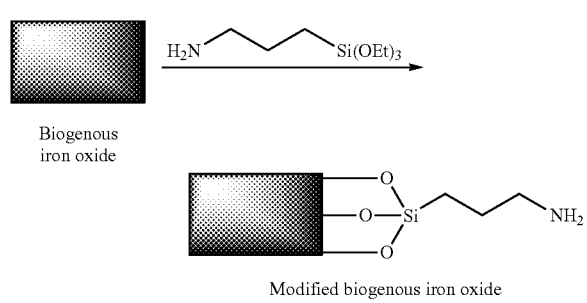

The formula above is schematically illustrated. In the formula, the oxygen binding to the biogenous iron oxide and the silicon of the silane coupling agent may be linked by a triple, double, or single bond, or a combination thereof. In addition, one or more groups that are introduced by the chemical modification are present. The same applies to the following formulae.

Elemental analysis of the obtained organic-inorganic composite material resulted in C: 7.85% and N: 1.93%. The organic group loading calculated from the carbon content was 15.0% (w/w) (1.74 mmol/g).

Example 2

Chemical Modification of the Biogenous Iron Oxide Using 3-methacryloxypropyltrimethoxysilane In accordance with the above-described general procedure, the biogenous iron oxide was chemically modified using 3-methacryloxypropyltrimethoxysilane, as shown in the following formula.

[Chem. 2]

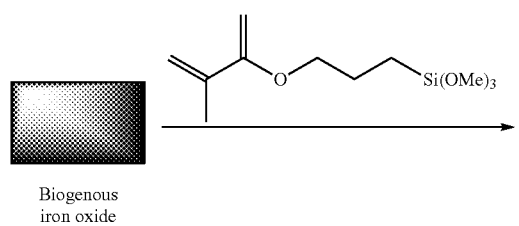

-continued

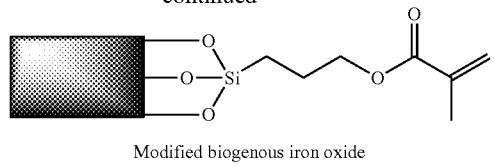

Modified biogenous iron oxide

Elemental analysis of the obtained chemically modified biogenous iron oxide resulted in C: 9.54% and N: 0.10%. The organic group loading calculated from the carbon content was 14.7% (w/w) (0.94 mmol/g). In addition, according to the results of FT-IR, C=O stretching vibration was observed at 1717 $cm^{-1}$.

Figure 9:
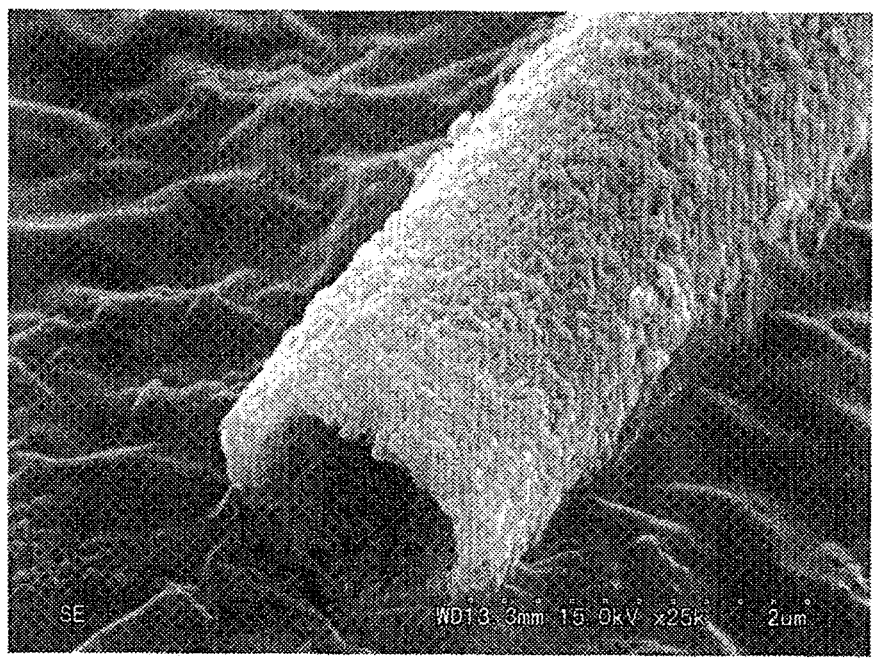
FIG. 9 shows an SEM photograph of the modified ceramic material obtained in Example 2.
Figure 10:
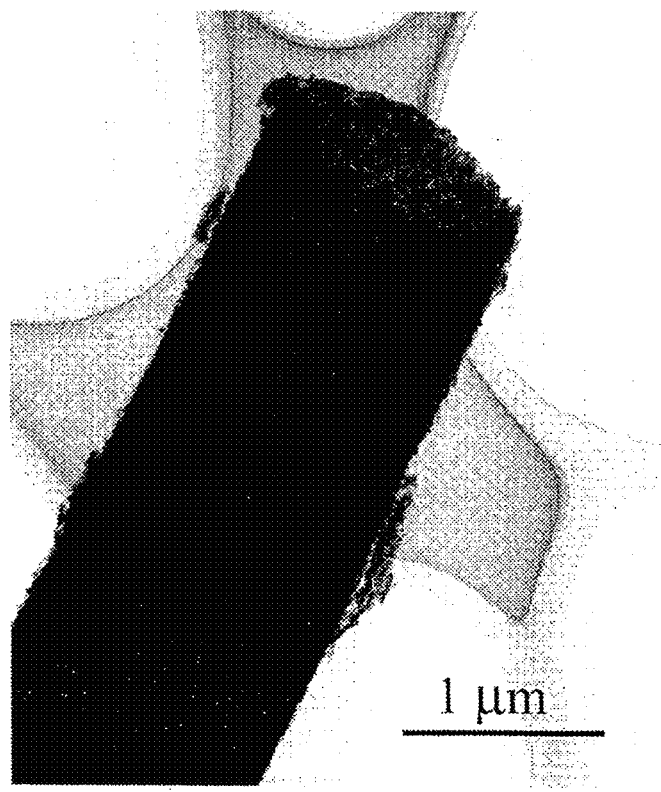
FIG. 10 shows a TEM photograph of the modified ceramic material obtained in Example 2.

In the process of a series of experimental procedures involving, for example, attaching an organic group to the biogenous iron oxide and separating the modified biogenous iron oxide, the characteristic shape originated from the biogenous iron oxide is not significantly impaired, apart from the length that is shortened. FIG. 9 shows an SEM photograph of the obtained modified biogenous iron oxide, and FIG. 10 shows a TEM photograph thereof. These photographs reveal that the sheath shape of the biogenous iron oxide and the nanoparticles constituting the sheath-shaped oxide are maintained even after the process of the chemical modification.

Example 3

Chemical Modification of the Biogenous Iron Oxide Using 3-mercaptopropyltrimethoxysilane In accordance with the above-described general procedure, the biogenous iron oxide was chemically modified using 3-mercaptopropyltrimethoxysilane, as shown in the following formula.

[Chem. 3]

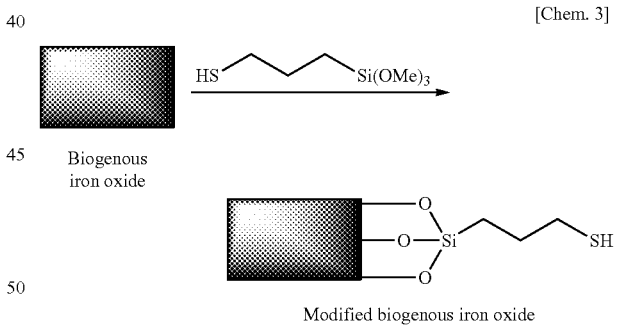

Elemental analysis of the obtained chemically modified biogenous iron oxide resulted in C: 6.04% and N: 0.00%. The organic group loading calculated from the carbon content was 12.6% (w/w) (1.22 mmol/g).

Example 4

Chemical Modification of the Biogenous Iron Oxide Using 3-chloropropyltriethoxysilane In accordance with the above-described general procedure, the biogenous iron oxide was chemically modified using 3-chloropropyltriethoxysilane, as shown in the following formula.

[Chem. 4]

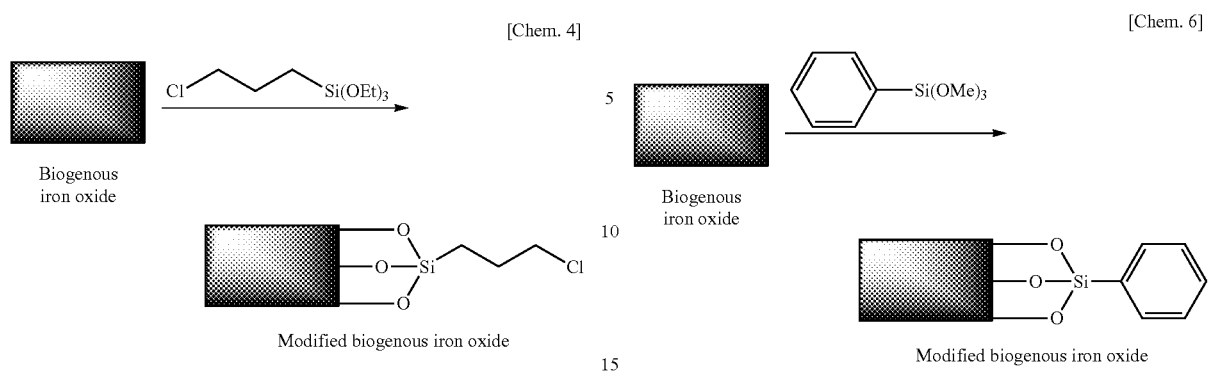

Elemental analysis of the obtained chemically modified biogenous iron oxide resulted in C: 4.83% and N: 0.47%. The organic group loading calculated from the carbon content was 9.2% (w/w) (0.87 mmol/g).

Example 5

Chemical Modification of the Biogenous Iron Oxide Using 3-glycidoxypropyltrimethoxysilane In accordance with the above-described general procedure, the biogenous iron oxide was chemically modified using 3-glycidoxypropyltrimethoxysilane, as shown in the following formula.

[Chem. 5]

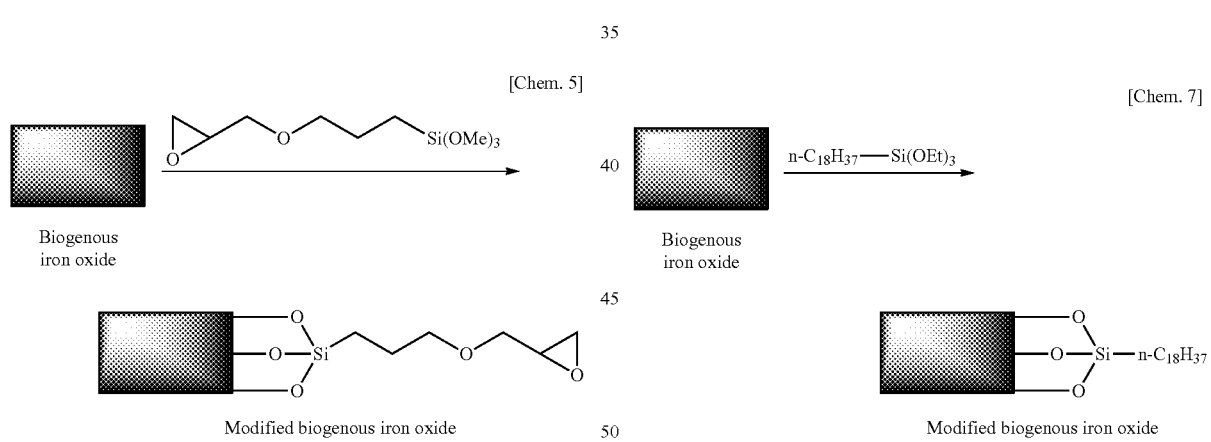

Elemental analysis of the obtained chemically modified biogenous iron oxide resulted in C: 6.41% and N: 0.04%. The organic group loading calculated from the carbon content was 9.4% (w/w) (0.66 mmol/g).

Example 6

Chemical Modification of Biogenous Iron Oxide Using Phenyltrimethoxysilane

In accordance with the above-described general procedure, the biogenous iron oxide was chemically modified using phenyltrimethoxysilane, as shown in the following formula.

[Chem. 6]

Elemental analysis of the obtained chemically modified biogenous iron oxide resulted in C: 6.06% and N: 0.44%. The organic group loading calculated from the carbon content was 6.3% (w/w) (0.60 mmol/g).

Example 7

Chemical Modification of the Biogenous Iron Oxide Using N-octadecyltriethoxysilane In accordance with the above-described general procedure, the biogenous iron oxide was chemically modified using n-octadecyltriethoxysilane, as shown in the following formula.

[Chem. 7]

Elemental analysis of the obtained chemically modified biogenous iron oxide resulted in C: 8.83% and N: 0.00%. The organic group loading calculated from the carbon content was 9.3% (w/w) (0.33 mmol/g).

Example 8

Chemical Modification of the Biogenous Iron Oxide Using Hexamethyldisilazane

In accordance with the above-described general procedure, the biogenous iron oxide was chemically modified using hexamethyldisilazane, as shown in the following formula.

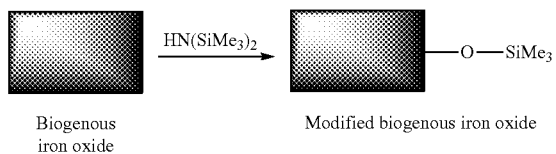

Elemental analysis of the obtained chemically modified biogenous iron oxide resulted in C: 4.59% and N: 0.00%. The organic group loading calculated from the carbon content was 6.2% (w/w) (0.84 mmol/g).

Example 9

Further Chemical Modification of the Chemically Modified Biogenous Iron Oxide Using Organic Group In accordance with the following formula, tetraphenylporphyrin was attached to the amino group present at the surface of the chemically modified biogenous iron oxide obtained in Example 1.

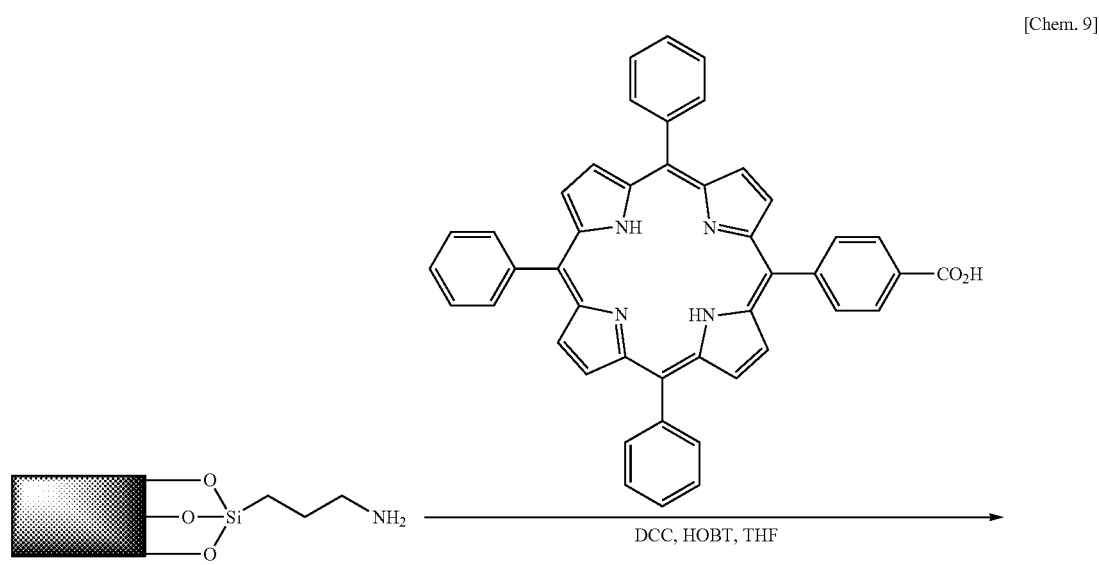

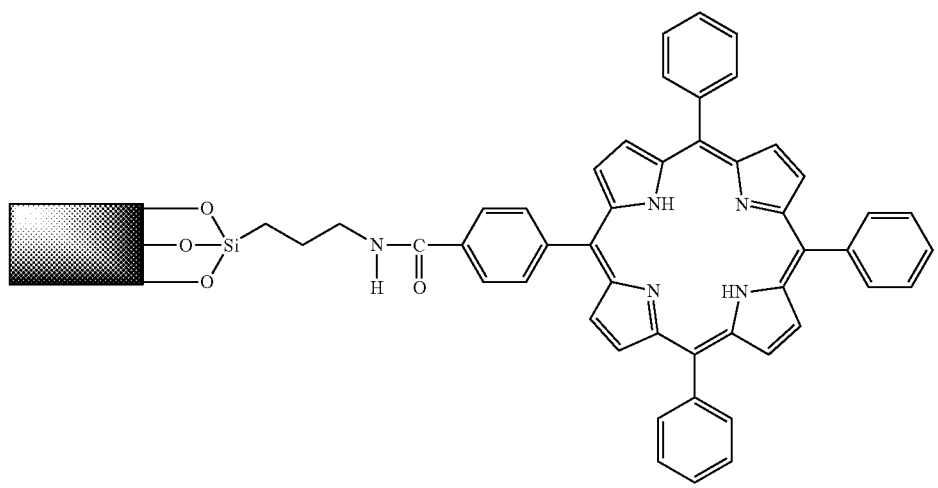

Porphyrin-modified biogenous iron oxide

The biogenous iron oxide to which aminopropyl had been introduced (300 mg), N,N'-dicyclohexylcarbodiimide (DCC) (78.5 mg, 0.380 mmol), and 1-hydroxybenzotriazole (HOBT) (51 mg, 0.377 mmol) were placed in a reactor, and the reactor was purged with nitrogen. Then, a solution in which 5-(4-carboxyphenyl)-10,15,20-triphenylporphyrin (100 mg, 0.152 mmol) was dissolved in dry tetrahydrofuran (4 mL) was added thereto and stirred at room temperature for 72 hours. The mixture was subjected to suction filtration, and washed with tetrahydrofuran, ethanol, heated ethanol, and hexane in this order, followed by vacuum-drying.

Elemental analysis of the obtained chemically modified biogenous iron oxide resulted in C: 10.41% and N: 2.10%. The porphyrin loading calculated from the nitrogen content was 11.1% (w/w) (0.17 mmol/g).

Figure 11:
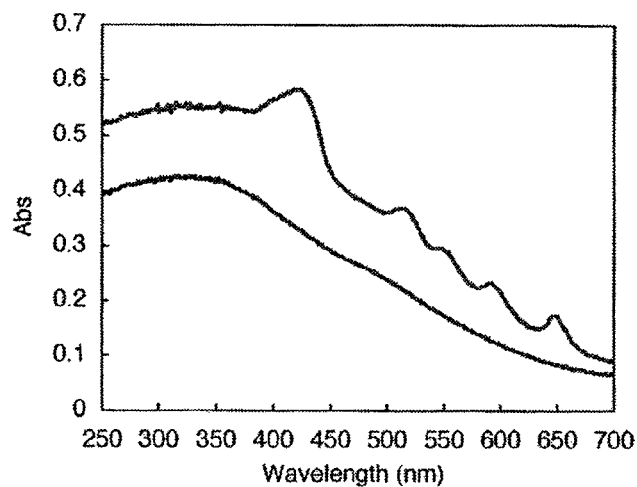
FIG. 11 shows an ultraviolet-visible absorption spectrum of the porphyrin-modified ceramic material obtained in Example 9.

The ultraviolet-visible absorption spectra confirmed the introduction of porphyrin to the biogenous iron oxide. FIG. 11 shows ultraviolet-visible absorption spectra (matrix: barium sulfate) of powder samples of the porphyrin-modified biogenous iron oxide (red line (upper line)) and the unmodified biogenous iron oxide (blue line (lower line)). The Soret absorption band of the porphyrin is clearly observed at 400 to 450 nm, and four Q absorption bands of the porphyrin are clearly observed at 500 to 650 nm.

Figure 12:
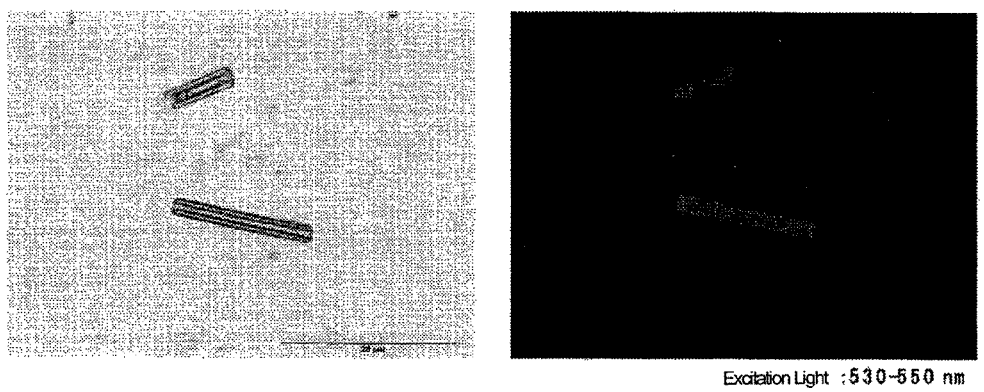
FIG. 12 shows optical microscope observation images (a bright-field observation image (left) and a fluorescence observation image (right)) of the porphyrin-modified ceramic material obtained in Example 9.

The introduction of porphyrin to the biogenous iron oxide was also confirmed by observation using an optical microscope. When the biogenous iron oxide was irradiated with excitation light (530 to 550 nm), a red fluorescence was emitted by porphyrin (FIG. 12). FIG. 12 is a bright-field observation image (left) and a fluorescence observation image (right). The images reveal that porphyrin molecules are attached to the biogenous iron oxide while being uniformly distributed over the entire biogenous iron oxide.

Example 10

Immobilization of *Burkholderia cepacia*-Derived Lipase (BCL) on the Modified Biogenous Iron Oxide *Burkholderia cepacia* lipase (BCL) (Wako Pure Chemical Ind., Ltd., Lipase PS IM Amano, Immobilized on Diatomaceous Earth, 31.3 g), a phosphate buffer (10 mM, pH 7.0, 125 mL), and a stirring bar were placed in a pear-shaped flask and stirred at room temperature for 3 hours. The mixture was subjected to suction filtration using a Büchner funnel, thereby obtaining an aqueous enzyme solution. The aqueous enzyme solution was placed in a dialysis membrane (molecular weight cut-off 10,000) and dialyzed against a phosphate buffer (10 mM, pH 7.0, 500 mL, twice for 30 minutes, twice for 1 hour, and once for 12 hours). The dialyzed aqueous enzyme solution (106 mL) and the biogenous iron oxide (obtained in Example 2) (500 mg), which had been preliminarily treated with 3-methacryloxypropyltrimethoxysilane, were placed in a centrifuge tube, and the tube was subjected to shaking (125 rpm) at 25° C. for 24 hours. The precipitate obtained by centrifugation (10,000 rpm, 10 minutes) was vacuum-dried, thereby obtaining 500 mg of chemically modified biogenous iron oxide-immobilized enzyme BCL.

The protein content in the supernatant collected after the centrifugation and in the aqueous enzyme solution used for immobilization was quantified by the Bradford method, and the lipase loading was calculated. The amount of the enzyme carried in the powder (500 mg) was 22.9 mg (4.6% (w/w)).

Example 11

Immobilization of *Candida antarctica*-Derived Lipase (CAL) on Modified Biogenous Iron Oxide An aqueous *Candida antarctica* lipase (CAL) solution (Novozymes Japan, Ltd., Lipozyme CALB L, 50 mL) was placed in a dialysis membrane (molecular weight cut-off 10,000) and dialyzed against a phosphate buffer (10 mM, pH 7.0, 300 mL, twice for 20 minutes, three times for 1 hour). The dialyzed aqueous enzyme solution (87 mL) and the modified biogenous iron oxide (obtained in Example 2) (501 mg), which had been preliminarily treated with 3-methacryloxypropyltrimethoxysilane, were placed in a centrifuge tube and subjected to shaking (125 rpm) at 25° C. for 24 hours. The precipitate obtained by centrifugation (10,000 rpm, 10 minutes) was vacuum-dried, thereby obtaining 489 mg of chemically modified biogenous iron oxide-immobilized enzyme CAL.

The protein content in the supernatant collected after the centrifugation and in the aqueous enzyme solution used for immobilization was quantified by the Bradford method, and the lipase loading was calculated. The amount of the enzyme carried in the powder (501 mg) was 15.3 mg (3.1% (w/w)).

Example 12

Kinetic Optical Resolution of Racemic Alcohol Using the Modified Biogenous Iron Oxide-Immobilized Lipase
Kinetic Optical Resolution of Chiral Alcohol Using the Chemically Modified Biogenous Iron Oxide-Immobilized Enzyme (1)

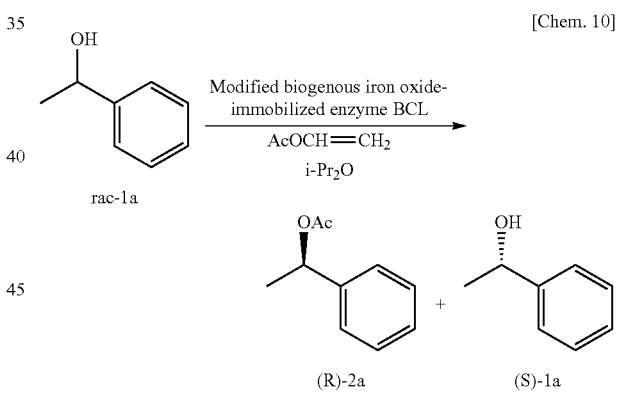

[Chem. 10]

1-Phenylethanol 1a (122 µL, 1.00 mmol), the chemically modified biogenous iron oxide-immobilized enzyme BCL (10 mg) obtained in Example 10, Molecular sieve 3A (3 particles), and dry diisopropyl ether (5 mL) were placed in a test tube and stirred at 30° C. for 30 minutes. Then, vinyl acetate (185 µL, 2.00 mmol) was added thereto to initiate a reaction. After stirring at 30° C. for 1 hour, the reaction solution was filtered through Celite and the solvent was distilled off, thereby obtaining a crude reaction product. Then, the ester and the alcohol were isolated by silica gel column chromatography (hexane/ethyl acetate (5:1)). Their optical purities were determined by gas chromatography using a chiral column. The spectrum data is shown below.
(S)-1a:
Isolated yield 31%; Optical purity 83% ee
$^1$H NMR (CDCl$_3$, 300 MHz) 1.51 (d, J=6.3 Hz, 3H), 1.77 (d, J=3.0 Hz, 1H), 4.87-4.95 (m, 1H), 7.28-7.41 (m, 5H)

GC: CP-cyclodextrin-β-2,3,6-M-19, Inj. 250° C., Col. 95° C., Det. 220° C., (R)-1a 30.0 min., (S)-1a 32.6 min.

(R)-2a:

Isolated yield 23%; Optical purity 98% ee $^1$H NMR (CDCl$_3$, 300 MHz) 1.54 (d, J=6.8 Hz, 3H), 2.07 (s, 3H), 5.88 (q, J=6.8 Hz, 1H), 7.27-7.36 (m, 5H)

GC: CP-cyclodextrin-β-2,3,6-M-19, Inj. 250° C., Col. 95° C., Det. 220° C., (S)-2a 24.6 min., (R)-2a 27.5 min.

Kinetic Optical Resolution of Chiral Alcohol Using the Chemically Modified Biogenous Iron Oxide-Immobilized Enzyme (2)

[Chem. 11]

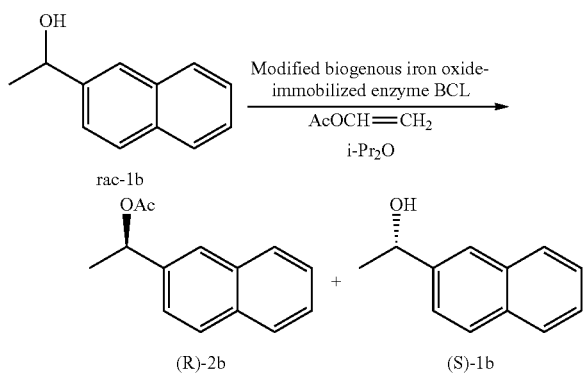

1-(2-Naphthyl)ethanol 1b (173 mg, 1.00 mmol), the chemically modified biogenous iron oxide-immobilized enzyme BCL (10 mg) obtained in Example 10, dry diisopropyl ether (5 mL), and Molecular sieve 3A (3 particles) were placed in a test tube and stirred at 30° C. for 30 minutes. Then, vinyl acetate (185 μL, 2.00 mmol) was added thereto to initiate a reaction. After stirring at 30° C. for 1 hour, the reaction solution was filtered through Celite and the solvent was distilled off, thereby obtaining a crude reaction product. Then, the ester and the alcohol were isolated by silica gel column chromatography (hexane/ethyl acetate (5:1)). Their optical purities were determined by HPLC using a chiral column. The spectrum data is shown below.

(S)-1b:

Isolated yield 56%; Optical purity 69% ee $[α]^{19}_D$=−32.6 (c 0.96, CHCl$_3$)

$^1$H NMR (CDCl$_3$, 500 MHz) 1.59 (d, J=6.0 Hz, 3H), 1.88 (s, 1H), 5.08 (q, J=6.0 Hz, 1H), 7.45-7.53 (m, 3H), 7.82-7.85 (m, 4H)

HPLC: Chiralcel OJ-H, hexane/i-PrOH (9:1), Flow rate 0.5 mL/min., Detected wavelength 254 nm, (S)-1b 30.2 min., (R)-1b 39.8 min.

(R)-2b:

Isolated yield 40%; Optical purity >99% ee $[α]^{20}_D$=+117 (c 1.04, CHCl$_3$)

$^1$H NMR (CDCl$_3$, 500 MHz) 1.63 (d, J=8.3 Hz, 3H), 2.10 (s, 3H), 6.05 (q, J=8.3 Hz, 1H), 7.48-7.49 (m, 3H), 7.81-7.85 (m, 4H)

HPLC: Chiralcel OJ-H, hexane/i-PrOH (9:1), Flow rate 0.5 mL/min., Detected wavelength 254 nm, (R)-2b 25.1 min., (S)-2b 28.9 min.

Kinetic Optical Resolution of Chiral Alcohol Using the Chemically Modified Biogenous Iron Oxide-Immobilized Enzyme (3)

[Chem. 12]

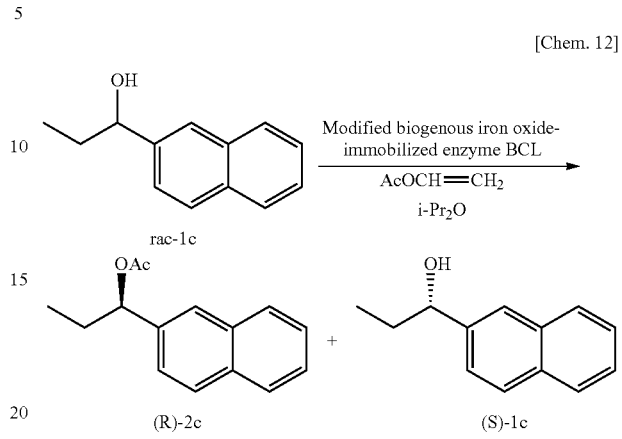

1-(2-Naphthyl)propanol 1c (186 mg, 1.00 mmol), the chemically modified biogenous iron oxide-immobilized enzyme BCL (10 mg) obtained in Example 10, dry diisopropyl ether (5 mL), and Molecular sieve 3A (3 particles) were placed in a test tube and stirred at 30° C. for 30 minutes. Then, vinyl acetate (185 μL, 2.00 mmol) was added thereto to initiate a reaction. After stirring at 30° C. for 12 hours, the reaction solution was filtered through Celite and the solvent was distilled off, thereby obtaining a crude reaction product. Then, the ester and the alcohol were isolated by silica gel column chromatography (hexane/ethyl acetate (5:1)). Their optical purities were determined by HPLC using a chiral column. The spectrum data is shown below.

(S)-1c:

Isolated yield 59%; Optical purity 77% ee $[α]^{22}_D$=−28.8 (c 1.03, CHCl$_3$)

$^1$H NMR (CDCl$_3$, 500 MHz) 0.95 (t, J=7.0 Hz, 3H), 1.83-1.95 (m, 3H), 4.78 (t, J=5.3 Hz, 1H), 7.45-7.49 (m, 3H), 7.79-7.85 (m, 4H)

HPLC: Chiralcel OJ-H, hexane/i-PrOH (9:1), Flow rate 0.5 mL/min., Detected wavelength 254 nm, (S)-1c 24.4 min., (R)-1c 33.5 min.

(R)-2c:

Isolated yield 40%; Optical purity 97% ee $[α]^{22}_D$=+96.8 (c 1.11, CHCl$_3$)

$^1$H NMR (CDCl$_3$, 500 MHz) 0.91 (t, J=7.5 Hz, 3H), 1.91-2.03 (m, 2H), 2.10 (s, 3H), 5.83 (t, J=7.0 Hz, 1H), 7.45-7.48 (m, 3H), 7.78-7.84 (m, 4H)

HPLC: Chiralcel OJ-H, hexane/i-PrOH (9:1), Flow rate 0.5 mL/min., Detected wavelength 254 nm, (R)-2c 18.7 min., (S)-2c 25.7 min.

Kinetic Optical Resolution of Chiral Alcohol Using the Chemically Modified Biogenous Iron Oxide-Immobilized Enzyme (4)

[Chem. 13]

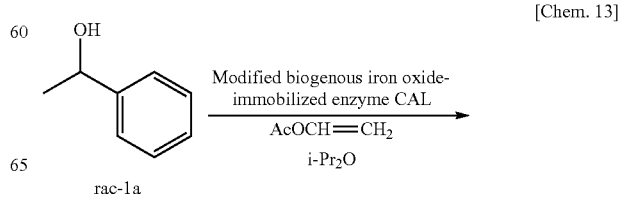

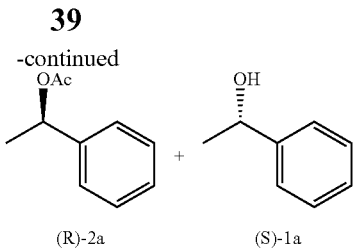

1-Phenylethanol 1a (122 μL, 1.00 mmol), the chemically modified biogenous iron oxide-immobilized enzyme CAL (10 mg) obtained in Example 11, Molecular sieve 3A (3 particles), and dry diisopropyl ether (5 ml) were placed in a test tube and stirred at 30° C. for 30 minutes. Then, vinyl acetate (185 μL, 2.00 mmol) was added thereto to initiate a reaction. After stirring at 30° C. for 3 hours, the reaction solution was filtered through Celite and the solvent was distilled off, thereby obtaining a crude reaction product. Then, the ester and the alcohol were isolated by silica gel column chromatography (hexane/ethyl (50:1) to (10:1)). Their optical purities were determined by gas chromatography using a chiral column. The spectrum data is shown below.

(S)-1a:
Isolated yield 45%; Optical purity 91% ee
$^1$H NMR (CDCl$_3$, 300 MHz) 1.51 (d, J=6.3 Hz, 3H), 1.77 (d, J=3.0 Hz, 1H), 4.87-4.95 (m, 1H), 7.28-7.41 (m, 5H)
GC: CP-cyclodextrin-β-2,3,6-M-19, Inj. 250° C., Col. 95° C., Det. 220° C., (R)-1a 30.0 min., (S)-1a 32.6 min.

(R)-2a:
Isolated yield 43%; Optical purity >99% ee
$^1$H NMR (CDCl$_3$, 300 MHz) 1.54 (d, J=6.8 Hz, 3H), 2.07 (s, 3H), 5.88 (q, J=6.8 Hz, 1H), 7.27-7.36 (m, 5H)
GC: CP-cyclodextrin-β-2,3,6-M-19, Inj. 250° C., Col. 95° C., Det. 220° C., (S)-2a 24.6 min., (R)-2a 27.5 min.

Kinetic Optical Resolution of Chiral Alcohol Using the Chemically Modified Biogenous Iron Oxide-Immobilized Enzyme (5)

[Chem. 14]

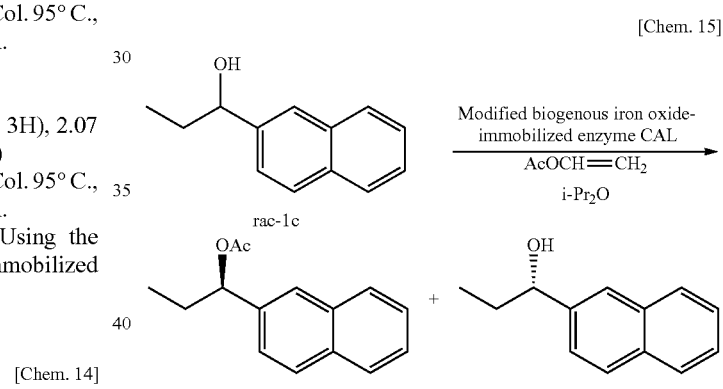

1-(2-Naphthyl)ethanol 1b (173 mg, 1.00 mmol), the chemically modified biogenous iron oxide-immobilized enzyme CAL (10 mg) obtained in Example 11, dry diisopropyl ether (5 mL), and Molecular sieve 3A (3 particles) were placed into a test tube and stirred at 30° C. for 30 minutes. Then, vinyl acetate (185 μL, 2.00 mmol) was added thereto to initiate a reaction. After stirring at 30° C. for 4.5 hours, the reaction solution was filtered through Celite and the solvent was distilled off, thereby obtaining a crude reaction product. Then, the ester and the alcohol were isolated by silica gel column chromatography (hexane/ethyl acetate (5:1)). Their optical purities were determined by HPLC using a chiral column. The spectrum data is shown below.

(S)-1b:
Isolated yield 45%; Optical purity 96% ee
$[\alpha]^{22}_D$=−46.2 (c 0.99, CHCl$_3$)
$^1$H NMR (CDCl$_3$, 500 MHz) 1.59 (d, J=6.0 Hz, 3H), 1.88 (s, 1H), 5.08 (q, J=6.0 Hz, 1H), 7.45-7.53 (m, 3H), 7.82-7.85 (m, 4H)
HPLC: Chiralcel OJ-H, hexane/i-PrOH (9:1), Flow rate 0.5 mL/min., Detected wavelength 254 nm, (S)-1b 30.2 min., (R)-1b 39.8 min.

(R)-2b:
Isolated yield 48%; Optical purity >99% ee
$[\alpha]^{22}_D$=+117 (c 0.99, CHCl$_3$)
$^1$H NMR (CDCl$_3$, 500 MHz) 1.63 (d, J=8.3 Hz, 3H), 2.10 (s, 3H), 6.05 (q, J=8.3 Hz, 1H), 7.48-7.49 (m, 3H), 7.81-7.85 (m, 4H)
HPLC: Chiralcel OJ-H, hexane/i-PrOH (9:1), Flow rate 0.5 mL/min., Detected wavelength 254 nm, (R)-2b 25.1 min., (S)-2b 28.9 min.

Kinetic Optical Resolution of Chiral Alcohol Using the Chemically Modified Biogenous Iron Oxide-Immobilized Enzyme (6)

[Chem. 15]

1-(2-Naphthyl)propanol 1c (186 mg, 1.00 mmol), the chemically modified biogenous iron oxide-immobilized enzyme CAL (10 mg) obtained in Example 11, dry diisopropyl ether (5 mL), and Molecular sieve 3A (3 particles) were placed in a test tube and stirred at 30° C. for 30 minutes. Then, vinyl acetate (185 μL, 2.00 mmol) was added thereto to initiate a reaction. After stirring at 30° C. for 70 hours, the reaction solution was filtered through Celite and the solvent was distilled off, thereby obtaining a crude reaction product. Then, the ester and the alcohol were isolated by silica gel column chromatography (hexane/ethyl acetate (5:1)). Their optical purities were determined by HPLC using a chiral column. The spectrum data is shown below.

(S)-1c:
Isolated yield 42%; Optical purity 88% ee
$[\alpha]^{20}_D$=−34.0 (c 1.03, CHCl$_3$)
$^1$H NMR (CDCl$_3$, 500 MHz) 0.95 (t, J=7.0 Hz, 3H), 1.83-1.95 (m, 3H), 4.78 (t, J=5.3 Hz, 1H), 7.45-7.49 (m, 3H), 7.79-7.85 (m, 4H)
HPLC: Chiralcel OJ-H, hexane/i-PrOH (9:1), Flow rate 0.5 mL/min., Detected wavelength 254 nm, (S)-1c 24.4 min., (R)-1c 33.5 min.

(R)-2c:
Isolated yield 41%; Optical purity >99% ee
$[\alpha]^{21}_D$=+93.1 (c 1.03, CHCl$_3$)
$^1$H NMR (CDCl$_3$, 500 MHz) 0.91 (t, J=7.5 Hz, 3H), 1.91-2.03 (m, 2H), 2.10 (s, 3H), 5.83 (t, J=7.0 Hz, 1H), 7.45-7.48 (m, 3H), 7.78-7.84 (m, 4H)
HPLC: Chiralcel OJ-H, hexane/i-PrOH (9:1), Flow rate 0.5 mL/min., Detected wavelength 254 nm, (R)-2c 18.7 min., (S)-2c 25.7 min.

Example 13

Comparison was made of the organic group loadings of the untreated biogenous iron oxide (ceramic material) obtained in the isolation and purification (1), the chemically modified biogenous iron oxide (ceramic material) obtained in Example 1, and chemically treated Toyonite 200 (produced by Toyo Denka Kogyo Co., Ltd.) in which a silane coupling agent was applied as in Example 1. In addition, comparison was made of the lipase loadings of the chemically modified biogenous iron oxide-immobilized enzyme obtained in Examples 10 and 11, untreated biogenous iron oxide and Toyonite 200-immobilized enzyme on which lipase (BCL or CAL) was immobilized as in Example 10 or 11. Table 2 shows the results.

TABLE 2

| Inorganic Carrier | 3-Methacryloxypropyltrimethoxysilane (Organic group) | | Lipase Loading | |
|---|---|---|---|---|
| | Treatment | Loading | BCL | CAL |
| Biogenous iron oxide | Yes | 15% | 4.6% | 3.1% |
| Biogenous iron oxide | No | — | 1.2% | 0.3% |
| Toyonite 200 | Yes | 1.4% | 2.9% | 2.5% |

It can be seen from the results that the biogenous iron oxide has a high loading of both a silane coupling agent and lipase, and that the biogenous iron oxide can thus be used as an excellent enzyme immobilization carrier. It can also be seen that when an untreated biogenous iron oxide is subjected to surface treatment with 3-methacryloxypropyltrimethoxysilane, the lipase loading increases.

Toyonite 200 is a porous spherical ceramic carrier obtained by adding a strong acid to a kaolin mineral, subjecting it to hydrothermal treatment with water, granulating the washed slurry or powder, and firing the resulting product at 350 to 1,000° C. Toyonite 200 is known as an excellent inorganic carrier used for lipase immobilization. The biogenous iron oxide served as a starting material of the organic-inorganic composite material of the present invention can be directly obtained from nature. Further, the biogenous iron oxide after chemical treatment has a higher lipase loading than Toyonite and is thus very advantageous both economically and environmentally.

Example 14

Chemical Modification of Biogenous Iron Oxide Using 3-(triethoxysilyl)propyltriphenylphosphonium bromide In accordance with the following procedure, the biogenous iron oxide was chemically modified using 3-(triethoxysilyl) propyltriphenylphosphonium bromide. The biogenous iron oxide (2.60 g) vacuum-dried at 150° C. for 4 hours was placed in a reactor, and the reactor was purged with nitrogen. Then, dry toluene (95 mL) was added to the reactor, and 3-(triethoxysilyl)propyltriphenylphosphonium bromide (2.60 g, 4.75 mmol) dissolved in dimethylformamide (4 mL) was added thereto. The mixture was stirred at 80° C. for 24 hours. The reaction solution was transferred to a centrifuge tube while being washed with ethanol. Then, centrifugation was performed (9,000 rpm, 10 minutes), and the supernatant was removed. A washing procedure for performing centrifugation with the addition of ethanol was repeated 4 times. The obtained precipitate was vacuum-dried.

[Chem. 16]

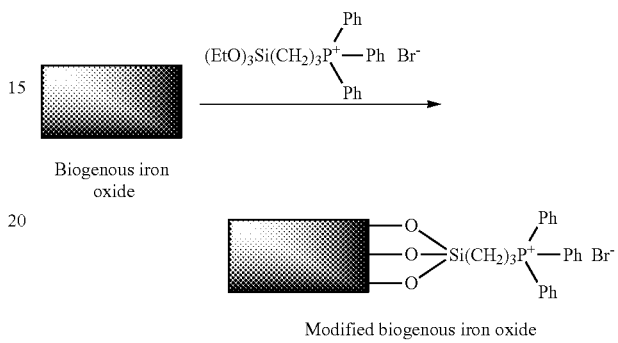

Elemental analysis of the obtained organic-inorganic composite material resulted in C: 9.40% and N: 0.50%. The organic group loading calculated from the carbon content was 12.7% (w/w) (0.31 mmol/g).

Example 15

Cycloaddition Reaction of Carbon Dioxide with Epoxide Using the Biogenous Iron Oxide-Immobilized Organic Catalyst

[Chem. 17]

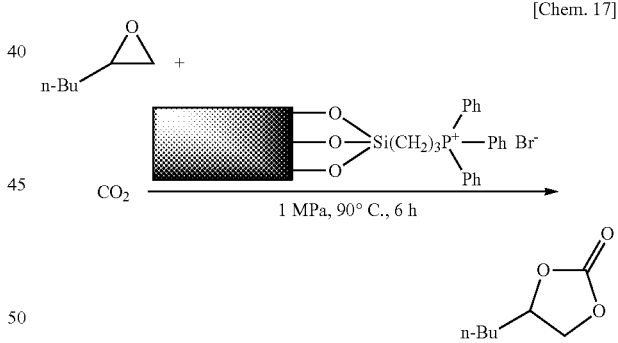

The biogenous iron oxide-immobilized organic catalyst obtained in Example 14 (650 mg, 2 mol %) and 1,2-epoxy hexane (1.20 mL, 10.0 mmol) were placed in a stainless-steel autoclave. Then, carbon dioxide (1 MPa) was introduced thereto, and the autoclave was heated at 90° C. for 6 hours. The autoclave was ice-cooled for 30 minutes. The reaction solution was filtered through Celite to remove the catalyst, and the resulting product was washed with ether. The obtained solution was concentrated and vacuum-dried. The crude reaction product was purified by silica gel-column chromatography, thereby obtaining the target compound at a 94% yield.
$^1$H NMR (CDCl$_3$, 500 MHz) 0.93 (t, J=7.2 Hz, 3H), 1.33-1.49 (m, 4H), 1.65-1.72 (m, 1H), 1.78-1.85 (m, 1H), 4.07 (dd, J=7.5, 8.5 Hz, 1H), 4.52 (t, J=8.5 Hz, 1H), 4.67-4.72 (m, 1H)

Example 16

Chemical Modification of the Biogenous Iron Oxide (OUMS1 Origin) Using 3-methacryloxypropyltrimethoxysilane In accordance with the above-described general procedure, the biogenous iron oxide (OUMS1 origin) was chemically modified using 3-methacryloxypropyltrimethoxysilane, as shown in the following formula.

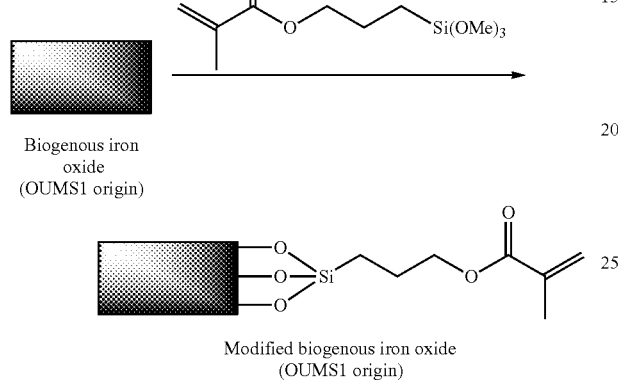

Elemental analysis of the obtained chemically modified biogenous iron oxide resulted in C: 12.60% and N: 1.76%. The organic group loading calculated from the carbon content was 9.13% (w/w) (0.59 mmol/g).

Example 17

Immobilization of *Burkholderia cepacia*-Derived Lipase (BCL) on the Modified Biogenous Iron Oxide (OUMS1 Origin)

*Burkholderia cepacia* lipase (BCL) (Wako Pure Chemical Ind. Ltd., Lipase PS IM Amano, Immobilized on Diatomaceous Earth, 1.87 g), a phosphate buffer (10 mM, pH 7.0, 14 mL), and a stirring bar were placed in a centrifuge tube and stirred at room temperature for 4 hours. After the powder was precipitated by centrifugation (9,000 rpm, 10 minutes), the supernatant was subjected to suction filtration using a Kiriyama funnel, thereby obtaining an aqueous enzyme solution. The aqueous enzyme solution was placed in a dialysis membrane (molecular weight cut-off 10,000) and dialyzed against a phosphate buffer (10 mM, pH 7.0, 500 mL, twice for 20 minutes, twice for 30 minutes, once for 1 hour, and once for 13 hours). The dialyzed aqueous enzyme solution (11.6 mL) and the biogenous iron oxide (OUMS1 origin, obtained in Example 16) (55.6 mg), which had been preliminarily treated with 3-methacryloxypropyltrimethoxysilane, were placed in a centrifuge tube and subjected to shaking (125 rpm) at 25° C. for 24 hours. After the supernatant was removed, ion exchange water (12 mL) was added thereto and the mixture was suspended. Then, centrifugation (9,000 rpm, 10 minutes) was performed. The above-described procedure was repeated 3 times. Subsequently, the obtained precipitate was vacuum-dried, thereby obtaining 55.3 mg of chemically modified biogenous iron oxide (OUMS1 origin)-immobilized enzyme BCL.

The protein content in the supernatant collected after the centrifugation and in the aqueous enzyme solution used for immobilization was quantified by the Bradford method, and the lipase loading was calculated. The amount of the enzyme carried in the powder (55.6 mg) was 1.5 mg (2.7% (w/w)).

Kinetic Optical Resolution of Chiral Alcohol Using Chemically Modified Biogenous Iron Oxide (OUMS1 Origin)-Immobilized Enzyme

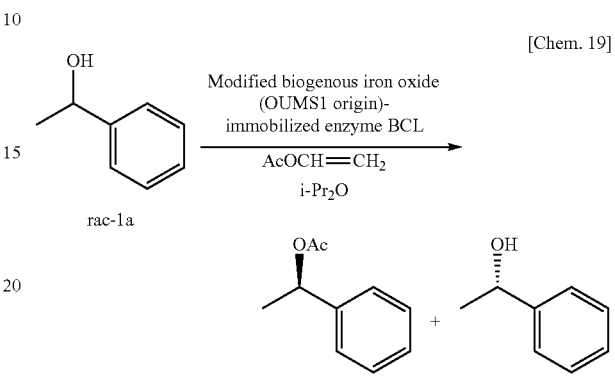

1-Phenylethanol 1a (121 μL, 1.00 mmol), the chemically modified biogenous iron oxide (OUMS1 origin)-immobilized enzyme BCL (16.5 mg) obtained in Example 17, Molecular sieve 3A (3 particles), and dry diisopropyl ether (5 mL) were placed in a test tube and stirred at 30° C. for 30 minutes. Then, vinyl acetate (185 μL, 2.00 mmol) was added thereto to initiate a reaction. After stirring at 30° C. for 13 hours, the reaction solution was filtered through Celite and the solvent was distilled off, thereby obtaining a crude reaction product. Their optical purities were determined by gas chromatography using a chiral column.

(S)-1a:
Optical purity 58% ee
(R)-2a:
Optical purity 99% ee

Example 18

Imparting Magnetism

In accordance with the following procedures (I), (II), and (III), the ceramic material obtained in isolation and purification (1) was subjected to heat treatment.

Procedure (I): A ceramic starting-material dry powder was fired using an electric muffle furnace OPM-28D produced by Advantech Co., Ltd., in atmospheric air at 800° C. for 2 hours. This operation was performed by rapid heating and quenching.

Figure 13:
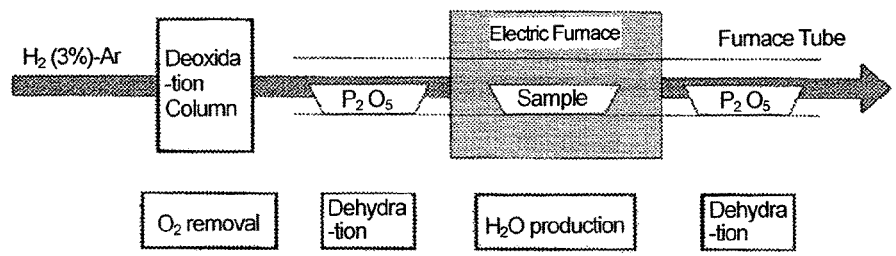
FIG. 13 schematically illustrates an electric furnace used in the hydrogen reduction step in procedure (II) of Example 18.

Procedure (II): The fired ceramic material obtained by procedure (I) was subjected to hydrogen reduction at 550° C. for 2 hours in an electric furnace (a tube furnace produced by Koyo Lindberg Ltd.) in the presence of $H_2$ (3%)-Ar gas mixture (1 atmospheric pressure). FIG. 13 schematically illustrates the hydrogen reduction step in procedure (II). A deoxidation column (a large oxygen trap produced by GL Sciences Inc.) was disposed immediately in front of $H_2$ (3%)-Ar gas mixture (0.1 MPa) inlet of the electric furnace, and $P_2O_5$ was placed at the front and back sides of the electric furnace containing the ceramic starting material to thereby perform the reduction treatment while removing traces of oxygen in the gas as well as the moisture generated during the reaction. Before the reduction treatment, the inside of the furnace was evacuated and then filled with $H_2$ (3%)-Ar gas mixture. The gas flow rate during the reaction was adjusted to 100 ccm. The temperature increase rate was 10° C./min, and the cooling was achieved by quenching.

Procedure (III): The sample obtained by procedure (II) of Example 18 was heated using an electric muffle furnace OPM-28D produced by Advantech Co., Ltd., in atmospheric air at 250° C. for 2 hours. This operation was performed by rapid heating and quenching.

The sample obtained by procedure (I) of Example 18, the sample obtained by procedures (I) to (II) of Example 18, and the sample obtained by procedures (I) to (III) of Example 18 were evaluated by X-ray diffraction (XRD) measurement, scanning electron microscope (SEM), elemental analysis, elemental mapping, Mossbauer spectroscopy, and vibrating sample magnetometer (VSM). Analysis Examples 1 to 4 below show the evaluation results.

Analysis Example 1

XRD Measurement

Figure 14:
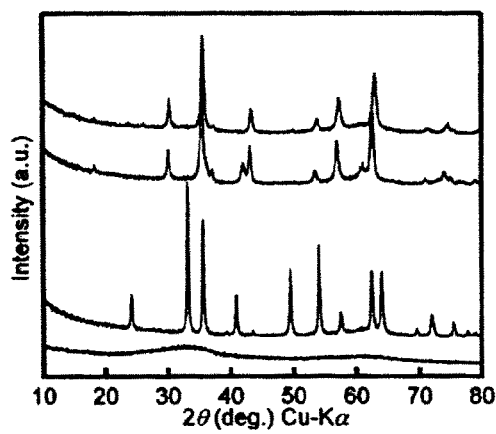
FIG. 14 shows XRD patterns of the sample obtained by procedure (I) of Example 18 (2nd from lowest), the sample obtained by procedures (I) to (II) of Example 18 (3rd from lowest), the sample obtained by procedures (I) to (III) of Example 18 (top), and the ceramic starting material (lowest).

The XRD patterns of the sample obtained by procedure (I) of Example 18, the sample obtained by procedures (I) to (II) of Example 18, the sample obtained by procedures (I) to (III) of Example 18, and the ceramic starting material were measured. FIG. 14 shows the results. For the XRD measuring device, a RINT-2000 produced by Rigaku Corporation was used. In the XRD patterns in FIG. 14, the lowest pattern corresponds to the ceramic starting material, the pattern at the second from the lowest corresponds to the sample obtained by procedure (I), the pattern at the third from the lowest corresponds to the sample obtained by procedures (I) to (II), and the top pattern corresponds to the sample obtained by procedures (I) to (III).

FIG. 14 confirmed the following: $\alpha$-$Fe_2O_3$ was formed almost in a single phase in the sample obtained by procedure (I), $Fe_3O_4$ was formed almost in a single phase in the sample obtained by procedures (I) to (II), and $\gamma$-$Fe_2O_3$ was formed almost in a single phase in the sample obtained by procedures (I) to (III).

Additionally, the lattice constants of the sample obtained by procedures (I) to (II) and the sample obtained by procedures (I) to (III) were calculated based on the XRD results. The calculated lattice constants were 8.397 Å and 8.344 Å, respectively. These lattice constants are in close agreement with the values of pure $Fe_3O_4$ and $\gamma$-$Fe_2O_3$ (8.396 Å and 8.347 Å). This confirmed that neither Si nor P in the form of solids was dissolved in the deposited magnetic iron oxide and that Fe, Si, and P were phase-separated.

The XRD patterns revealed no clear peaks originating from Si or P. This suggested that Si and P were forming an oxide having an amorphous structure. The crystallite size estimated based on the XRD patterns was confirmed as about 20 nm.

Figure 15:
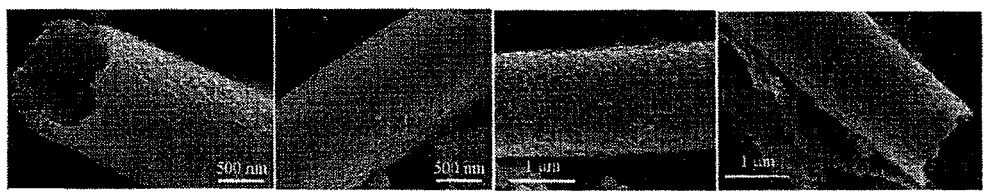
FIG. 15 shows SEM images of the sample obtained by procedure (I) of Example 18 (2nd from left), the sample obtained by procedures (I) to (II) of Example 18 (3rd from left), the sample obtained by procedures (I) to (III) of Example 18 (far right), and the ceramic starting material (far left).

FIG. 15 shows SEM images of the sample obtained by procedure (I) of Example 18, the sample obtained by procedures (I) to (II) of Example 18, the sample obtained by procedures (I) to (III) of Example 18, and the ceramic starting material. SEM was performed using a Hitachi S-4300 produced by Hitachi, Ltd. FIG. 15 confirmed that the tubular shape of the ceramic starting material was mostly maintained in the sample obtained by procedure (I), the sample obtained by procedures (I) to (II), and the sample obtained by procedures (I) to (III). It was also continued that almost no difference was found in the surface shape between the sample obtained by procedures (I) to (II) and the sample obtained by procedures (I) to (III).

Analysis Example 2

Elemental Analysis

Figure 16:
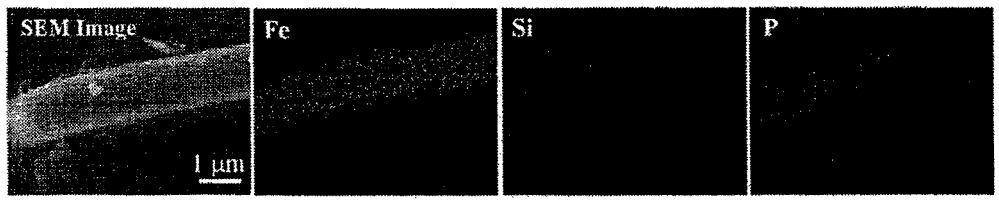
FIG. 16 shows the elemental mapping of the sample obtained by procedure (I) to (II) of Example 18.

According to the results of the elemental analysis of the sample obtained by procedures (I) to (II) of Example 18, the sample had the same composition ratio as that of the ceramic starting material. Specifically, for the sample obtained by procedure (II), Fe:Si:P was 73:23:4, and for the ceramic starting material, Fe:Si:P was 73:22:5. FIG. 16 shows the elemental mapping results. EDAX Genesis 2000 produced by Ametek, Inc., was used for the elemental analysis performed by EDX. Although Fe, Si, and P were phase-separated, all the elements were uniformly distributed on the order of submicrons. These results suggest that the phase separation of Fe, Si, and P occurs on the nano order.

Analysis Example 3

Chemical State Analysis of Iron Based on Mossbauer Spectroscopy

Figure 17:
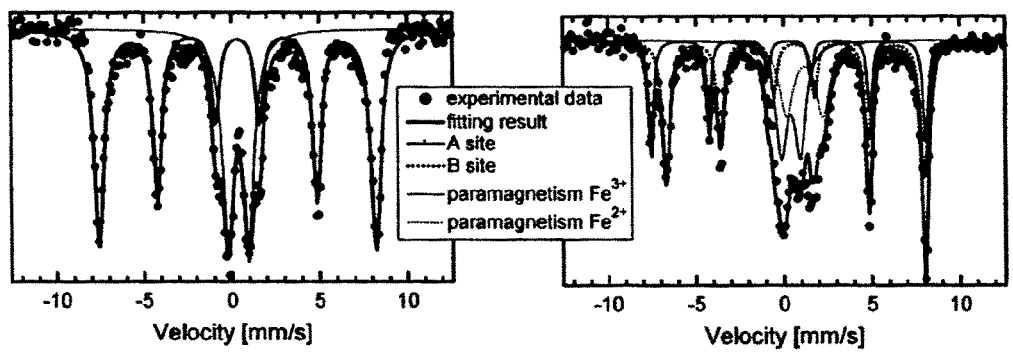
FIG. 17 shows Mössbauer spectra of the sample obtained by procedures (I) to (II) of Example 18 (left) and the sample obtained by procedures (I) to (III) of Example 18 (right).

FIG. 17 shows Mössbauer spectra of the sample obtained by procedures (I) to (II) of Example 18 and the sample obtained by procedures (I) to (III) of Example 18. MDF-200 produced by Toyo Researches (currently Topologic Systems, Inc.) was used for the Mossbauer spectroscopy measurement. The Mossbauer spectra confirmed that about 60 percent of Fe contained in the sample obtained by procedures (I) to (II) was $Fe_3O_4$, and about 40 percent was paramagnetic $Fe^{2+}$ and $Fe^{3+}$. It was also confirmed that about 70 percent of Fe contained in the sample obtained by procedures (I) to (III) was $\gamma$-$Fe_2O_3$, and about 30 percent was paramagnetic $Fe^{2+}$ and $Fe^{3+}$.

Here, assuming that the paramagnetic $Fe^{2+}$ and $Fe^{3+}$ components were the Fe components constituting the amorphous phase, the composition of the amorphous phase was calculated based on the results of Mossbauer spectroscopy and composition ratio of the ceramic starting material, i.e., Fe:Si:P=73:22:5. As a result, the composition of the amorphous phase of the sample obtained by procedures (I) to (II) of Example 18 was Fe:Si:P 52:39:9, and the composition of the amorphous phase of the sample obtained by procedures (I) to (III) was Fe:Si:P=45:45:10. Table 3 shows the composition of the amorphous phase.

TABLE 3

|  | Fe | Si | P |
| --- | --- | --- | --- |
| Starting ceramic material | 73 | 22 | 5 |
| Sample obtained by procedures (I) to (II) of Example 18 | 45 | 45 | 10 |
| Sample obtained by procedures (I) to (III) of Example 18 | 52 | 39 | 9 |

Analysis Example 4

Evaluation of Magnetic Properties Using VSM

Figure 18:
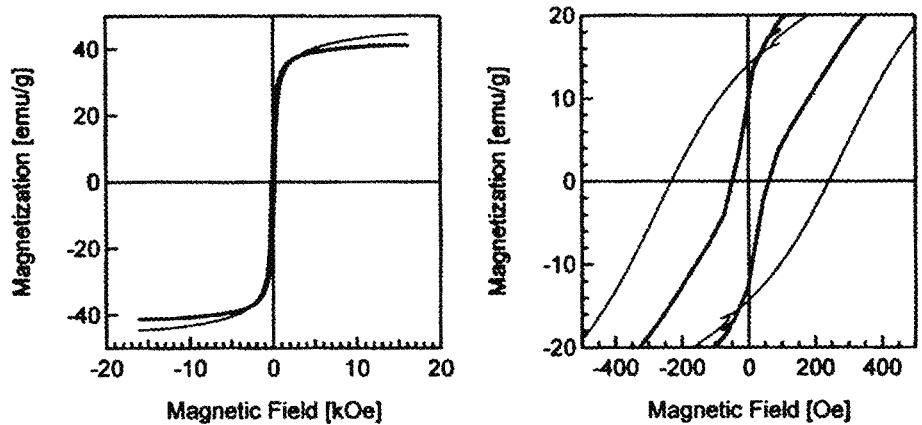
FIG. 18 shows VSM measurement results of the sample obtained by procedures (I) to (II) of Example 18 (thinner line) and the sample obtained by procedures (I) to (III) of Example 18 (thicker line).

Using a vibrating sample magnetometer (VSM-5-15, produced by Toei Industry Co., Ltd.), magnetic properties of the sample obtained by procedures (I) to (II) of Example 18 and the sample obtained by procedures (I) to (III) of Example 18 were measured. FIG. 18 and Table 4 show the results.

TABLE 4

|  | Saturation magnetization (emu/g) | Coercivity (Oe) | Residual magnetization (emu/g) |
| --- | --- | --- | --- |
| Sample obtained by procedures (I) to (II) of Example 18 | 45 | 235 | 14 |
| Sample obtained by procedures (I) to (III) of Example 18 | 41 | 55 | 11 |

The sample obtained by procedures (I) to (II) of Example 18 had a saturation magnetization of 45 emu/g, a coercivity of 235 Oe, and a residual magnetization of 14 emu/g, and the sample obtained by procedures (I) to (III) had a saturation magnetization of 41 emu/g, a coercivity of 55 Oe, and a residual magnetization of 11 emu/g. It was thereby confirmed that these samples exhibited ferrimagnetism. The saturation magnetizations of pure $Fe_3O_4$ and $\gamma$-$Fe_2O_3$ are 98 emu/g and 81 emu/g, respectively. In view of this, it was confirmed that the sample obtained by procedures (I) to (II) of Example 18 and the sample obtained by procedures (I) to (III) of Example 18 comprise about 50% of magnetic iron oxide particles, and the other about 50% of an amorphous phase comprising an oxide of Fe, Si, and P.

Example 19

Chemical Modification of Magnetic Ceramic Material ($\gamma$-$Fe_2O_3$) Using 3-methacryloxypropyltrimethoxysilane In accordance with the above-described general procedure, the magnetic ceramic material ($\gamma$-$Fe_2O_3$) obtained in Example 18 was chemically modified using 3-methacryloxypropyltrimethoxysilane, as shown in the following formula.

[Chem. 20]

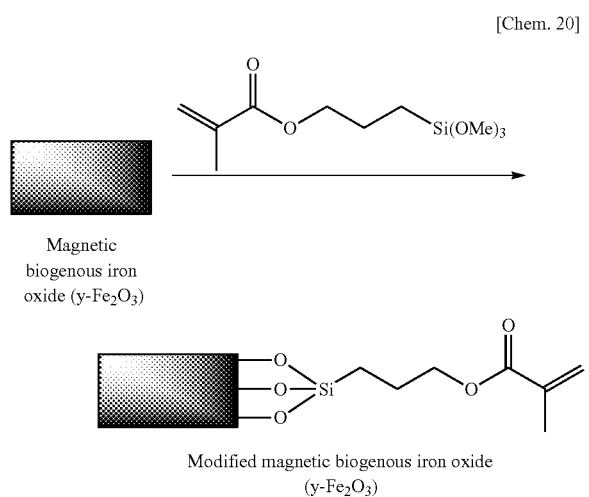

Figure 19:
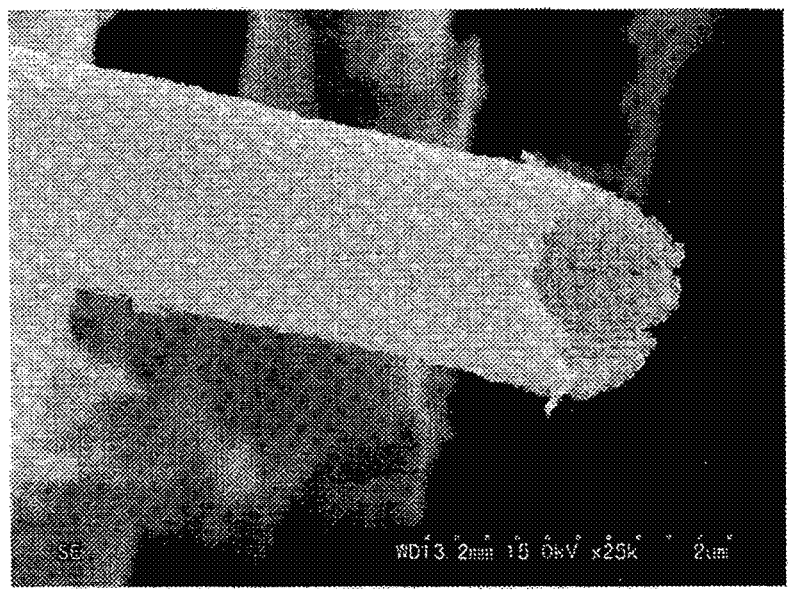
FIG. 19 shows an SEM photograph of the chemically modified magnetic ceramic material ($\gamma$-$Fe_2O_3$) obtained in Example 19.
Figure 20:
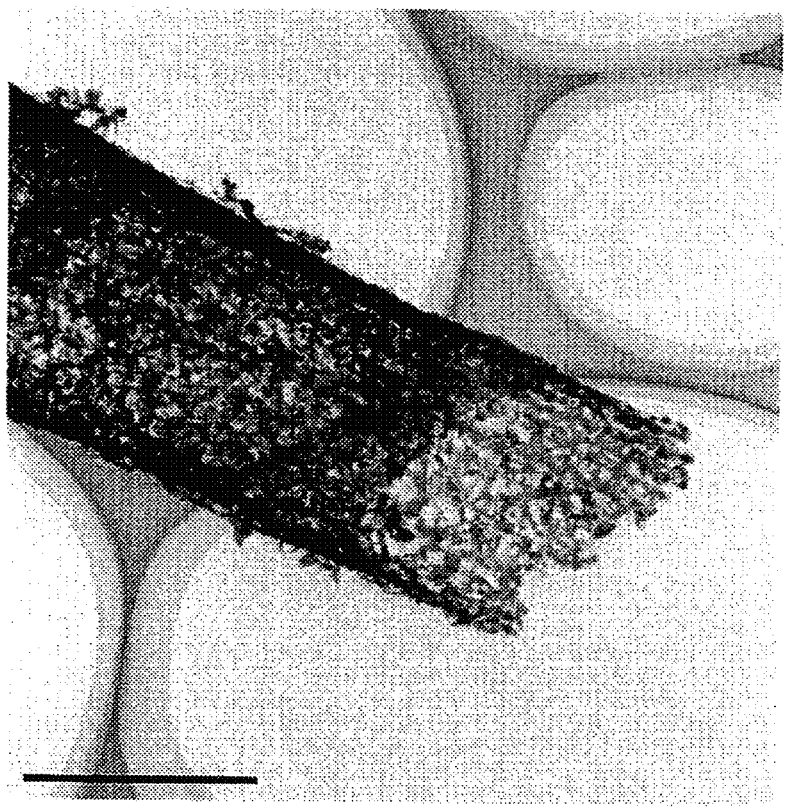
FIG. 20 shows a TEM photograph of the chemically modified magnetic ceramic material ($\gamma$-$Fe_2O_3$) obtained in Example 19.

Elemental analysis of the obtained chemically modified magnetic ceramic material ($\gamma$-$Fe_2O_3$) resulted in C: 3.73% and N: 0.00%. The organic group loading calculated from this carbon content was 6.3% (w/w) (0.41 mmol/g). In addition, according to the results of FT-IR, C=O stretching vibration was observed at 1717 $cm^{-1}$. FIG. 19 shows an SEM photograph of the obtained chemically modified magnetic ceramic material ($\gamma$-$Fe_2O_3$), and FIG. 20 shows a TEM photograph thereof. These photographs reveal that the shape of the magnetic ceramic material is maintained even after the process of the chemical modification.

Example 20

Immobilization of *Burkholderia cepacia*-Derived Lipase (BCL) on the Modified Magnetic Ceramic Material ($\gamma$-$Fe_2O_3$)

*Burkholderia cepacia* lipase (BCL) (Wako Pure Chemical Ind. Ltd., Lipase PS IM Amano, Immobilized on Diatomaceous Earth, 6.3 g), a phosphate buffer (10 mM, pH 7.0, 25 mL), and a stirring bar were placed in a pear-shaped flask and stirred at room temperature for 3 hours. The mixture was subjected to suction filtration using a Büchner funnel, thereby obtaining an aqueous enzyme solution. The aqueous enzyme solution was placed in a dialysis membrane (molecular weight cut-off 10,000) and dialyzed against a phosphate buffer (10 mM, pH 7.0, 500 mL, twice for 30 minutes, twice for 1 hour, and once for 12 hours). The dialyzed aqueous enzyme solution (53 mL) and the modified magnetic ceramic material ($\gamma$-$Fe_2O_3$) (obtained in Example 19) (100 mg), which had been preliminarily treated with 3-methacryloxypropyltrimethoxysilane, were placed in a pear-shaped flask and subjected to shaking (125 rpm) at 27° C. for 24 hours. The resulting product was transferred to a centrifuge tube, and the precipitate obtained by centrifugation (10,000 rpm, 10 minutes) was vacuum-dried, thereby obtaining 109 mg of chemically modified magnetic ceramic material-immobilized enzyme BCL.

The protein content in the supernatant collected after the centrifugation and in the aqueous enzyme solution used for immobilization was quantified by the Bradford method, and the lipase loading was calculated. The amount of the enzyme carried in the powder (100 mg) was 3.08 mg (3.8% (w/w)).

Example 21

Immobilization of *Candida antarctica*-Derived Lipase (CAL) on the Modified Magnetic Ceramic Material ($\gamma$-$Fe_2O_3$)

An aqueous *Candida antarctica* lipase (CAL) solution (Novozymes Japan, Ltd., Lipozyme CALB L, 15 mL) was placed in a dialysis membrane (molecular weight cut-off 10,000) and dialyzed against a phosphate buffer (10 mM, pH 7.0, 300 mL, twice for 20 minutes, 3 times for 1 hour). The dialyzed aqueous enzyme solution (32 mL) and the modified magnetic ceramic material ($\gamma$-$Fe_2O_3$) (obtained in Example 19) (115 mg), which had been preliminarily treated with 3-methacryloxypropyltrimethoxysilane, were placed in a pear-shaped flask and subjected to shaking (125 rpm) at 27° C. for 24 hours. The resulting product was transferred to a centrifuge tube, and the precipitate obtained by centrifugation (10,000 rpm, 10 minutes) was vacuum-dried, thereby obtaining 134 mg of chemically modified magnetic ceramic material-immobilized enzyme CAL.

The protein content in the supernatant collected after the centrifugation and in the aqueous enzyme solution used for immobilization was quantified by the Bradford method, and the lipase loading was calculated. The amount of the enzyme carried in the powder (115 mg) was 8.1 mg (7.1% (w/w)).

Kinetic Optical Resolution of Chiral Alcohol Using the Chemically Modified Magnetic Ceramic Material-Immobilized Enzyme (1)

[Chem. 21]

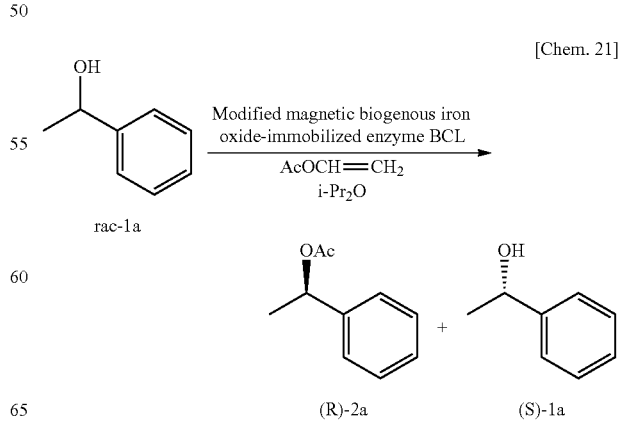

1-Phenylethanol 1a (122 μL, 1.00 mmol), the chemically modified magnetic ceramic material-immobilized enzyme BCL (12.1 mg) obtained in Example 20, Molecular sieve 3A (3 particles), and dry diisopropyl ether (5 mL) were placed in a test tube and stirred at 30° C. for 30 minutes. Then vinyl acetate (185 μL, 2.00 mmol) was added thereto to initiate a reaction. After stirring at 30° C. for 2.5 hours, the reaction solution was filtered through Celite, and the solvent was distilled off, thereby obtaining a crude reaction product. Then, the ester and the alcohol were isolated by silica gel column chromatography (hexane/diethyl ether (50:1) to (10:1)). Their optical purities were determined by gas chromatography using a chiral column. The spectrum data is shown below.

(S)-1a:

Isolated yield 48%; Optical purity 89% ee $[\alpha]^{32}_D = -32.6$ (c 0.73, $CHCl_3$)

$^1$H NMR ($CDCl_3$, 300 MHz) 1.51 (d, J=6.3 Hz, 3H), 1.77 (d, J=3.0 Hz, 1H), 4.87-4.95 (m, 1H), 7.28-7.41 (m, 5H)

GC: CP-cyclodextrin-β-2,3,6-M-19, Inj. 250° C., Col. 95° C., Det. 220° C., (R)-1a 30.0 min., (S)-1a 32.6 min.

(R)-2a:

Isolated yield 40%; Optical purity >99% ee $[\alpha]^{33}_D = +125$ (c 0.73, $CHCl_3$)

$^1$H NMR ($CDCl_3$, 300 MHz) 1.54 (d, J=6.8 Hz, 3H), 2.07 (s, 3H), 5.88 (q, J=6.8 Hz, 1H), 7.27-7.36 (m, 5H)

GC: CP-cyclodextrin-β-2,3,6-M-19, Inj. 250° C., Col. 95° C., Det. 220° C., (S)-2a 24.6 min., (R)-2a 27.5 min.

Kinetic Optical Resolution of Chiral Alcohol Using the Chemically Modified Magnetic Ceramic Material-Immobilized Enzyme (2)

[Chem. 22]

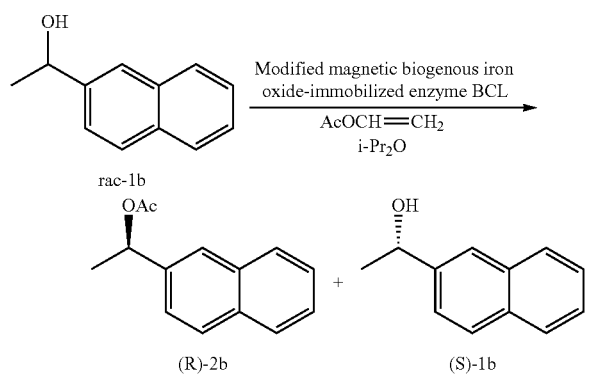

1-(2-Naphthyl)ethanol 1b (172 mg, 1.00 mmol), the chemically modified magnetic ceramic material-immobilized enzyme BCL (12.1 mg) obtained in Example 20, dry diisopropyl ether (5 mL), and Molecular sieve 3A (3 particles) were placed in a test tube and stirred at 30° C. for 30 minutes. Then, vinyl acetate (185 μL, 2.00 mmol) was added thereto to initiate a reaction. After stirring at 30° C. for 6 hours, the reaction solution was filtered through Celite and the solvent was distilled off, thereby obtaining a crude reaction product. Then, the ester and the alcohol were isolated by silica gel column chromatography (hexane/ethyl acetate (50:1) to (10:1)). Their optical purities were determined by HPLC using a chiral column. The spectrum data is shown below.

(S)-1b:

Isolated yield 44%; Optical purity >99% ee $[\alpha]^{29}_D = -47.8$ (c 1.00, $CHCl_3$)

$^1$H NMR ($CDCl_3$, 500 MHz) 1.59 (d, J=6.0 Hz, 3H), 1.88 (s, 1H), 5.08 (q, J=6.0 Hz, 1H), 7.45-7.53 (m, 3H), 7.82-7.85 (m, 4H)

HPLC: Chiralcel OJ-H, hexane/i-PrOH (9:1), Flow rate 0.5 mL/min., Detected wavelength 254 nm, (S)-1b 30.2 min., (R)-1b 39.8 min.

(R)-2b:

Isolated yield 40%; Optical purity 99% ee $[\alpha]^{30}_D = +128$ (c 1.00, $CHCl_3$)

$^1$H NMR ($CDCl_3$, 500 MHz) 1.63 (d, J=8.3 Hz, 3H), 2.10 (s, 3H), 6.05 (q, J=8.3 Hz, 1H), 7.48-7.49 (m, 3H), 7.81-7.85 (m, 4H)

HPLC: Chiralcel OJ-H, hexane/i-PrOH (9:1), Flow rate 0.5 mL/min., Detected wavelength 254 nm, (R)-2b 25.1 min., (S)-2b 28.9 min.

Kinetic Optical Resolution of Chiral Alcohol Using the Chemically Modified Magnetic Ceramic Material-Immobilized Enzyme (3)

[Chem. 23]

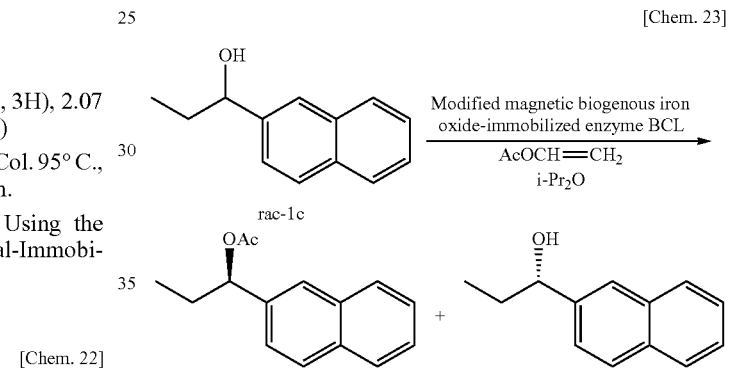

1-(2-Naphthyl)propanol 1c (186 mg, 1.00 mmol), the chemically modified magnetic ceramic material-immobilized enzyme BCL (12.1 mg) obtained in Example 20, dry diisopropyl ether (5 mL), and Molecular sieve 3A (3 particles) were placed in a test tube and stirred at 30° C. for 30 minutes. Then, vinyl acetate (185 μL, 2.00 mmol) was added thereto to initiate a reaction. After stirring at 30° C. for 24 hours, the reaction solution was filtered through Celite and the solvent was distilled off, thereby obtaining a crude reaction product. Then, the ester and the alcohol were isolated by silica gel column chromatography (hexane/ethyl acetate (50:1) to (10:1)). Their optical purities were determined by HPLC using a chiral column. The spectrum data is shown below.

(S)-1c:

Isolated yield 53%; Optical purity 51% ee $[\alpha]^{31}_D = -23.5$ (c 1.04, $CHCl_3$)

$^1$H NMR ($CDCl_3$, 500 MHz) 0.95 (t, J=7.0 Hz, 3H), 1.83-1.95 (m, 3H), 4.78 (t, J=5.3 Hz, 1H), 7.45-7.49 (m, 3H), 7.79-7.85 (m, 4H)

HPLC: Chiralcel OJ-H, hexane/i-PrOH (9:1), Flow rate 0.5 mL/min., Detected wavelength 254 nm, (S)-1c 24.4 min., (R)-1c 33.5 min.

(R)-2c:

Isolated yield 28%; Optical purity 97% ee $[\alpha]^{30}_D = +96.8$ (c 1.03, $CHCl_3$)

$^1$H NMR (CDCl$_3$, 500 MHz) 0.91 (t, J=7.5 Hz, 3H), 1.91-2.03 (m, 2H), 2.10 (s, 3H), 5.83 (t, J=7.0 Hz, 1H), 7.45-7.48 (m, 3H), 7.78-7.84 (m, 4H)

HPLC: Chiralcel OJ-H, hexane/i-PrOH (9:1), Flow rate 0.5 mL/min., Detected wavelength 254 nm, (R)-2c 18.7 min., (S)-2c 25.7 min.

Kinetic Optical Resolution of Chiral Alcohol Using the Chemically Modified Magnetic Ceramic Material-Immobilized Enzyme (4)

[Chem. 24]

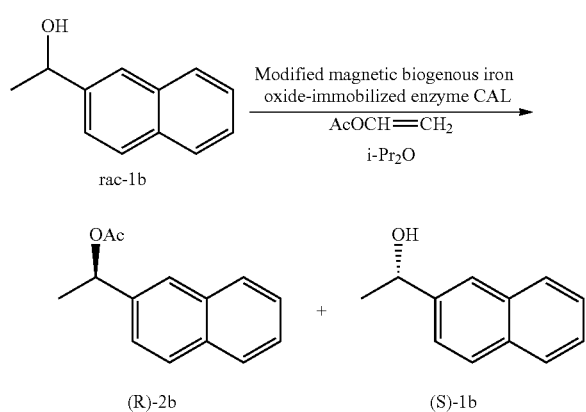

rac-1b (R)-2b          (S)-1b 1-(2-Naphthyl)ethanol 1b (172 mg, 1.00 mmol), the chemically modified magnetic ceramic material-immobilized enzyme CAL (4.4 mg) obtained in Example 21, dry diisopropyl ether (5 mL), and Molecular sieve 3A (3 particles) were placed in a test tube and stirred at 30° C. for 30 minutes. Then, vinyl acetate (185 µL, 2.00 mmol) was added thereto to initiate a reaction. After stirring at 30° C. for 4.5 hours, the reaction solution was filtered through Celite, and the solvent was distilled off, thereby obtaining a crude reaction product. Then, the ester and the alcohol were isolated by silica gel column chromatography (hexane/ethyl acetate (10:1)). Their optical purities were determined by HPLC using a chiral column. The spectrum data is shown below.

(S)-1b:

Isolated yield 56%; Optical purity 66% ee $[\alpha]^{25}{}_D$=−36.6 (c 1.04, CHCl$_3$)

$^1$H NMR (CDCl$_3$, 500 MHz) 1.59 (d, J=6.0 Hz, 3H), 1.88 (s, 1H), 5.08 (q, J=6.0 Hz, 1H), 7.45-7.53 (m, 3H), 7.82-7.85 (m, 4H)

HPLC: Chiralcel. OJ-H, hexane/i-PrOH (9:1), Flow rate 0.5 mL/min., Detected wavelength 254 nm, (S)-1b 30.2 min., (R)-1b 39.8 min.

(R)-2b:

Isolated yield 33%; Optical purity 95% ee $[\alpha]^{25}{}_D$=+118 (c 1.03, CHCl$_3$)

$^1$H NMR (CDCl$_3$, 500 MHz) 1.63 (d, J=8.3 Hz, 3H), 2.10 (s, 3H), 6.05 (q, J=8.3 Hz, 1H), 7.48-7.49 (m, 3H), 7.81-7.85 (m, 4H)

HPLC: Chiralcel OJ-H, hexane/i-PrOH (9:1), Flow rate 0.5 mL/min., Detected wavelength 254 nm, (R)-2b 25.1 min., (S)-2b 28.9 min.

Kinetic Resolution of Chiral Alcohol Using the Chemically Modified Magnetic Ceramic Material-Immobilized Enzyme (5)

[Chem. 25]

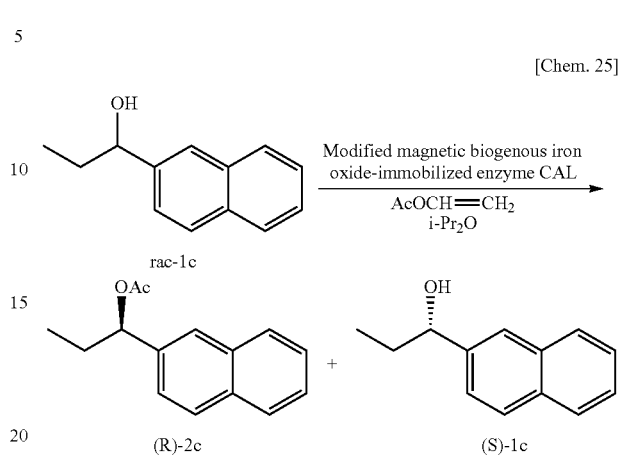

rac-1c (R)-2c          (S)-1c 1-(2-Naphthyl)propanol 1c (186 mg, 1.00 mmol), the chemically modified magnetic ceramic material-immobilized enzyme CAL (4.4 mg) obtained in Example 21, dry diisopropyl ether (5 mL), and molecular sieve 3A (3 particles) were placed in a test tube and stirred at 30° C. for 30 minutes. Then, vinyl acetate (185 µL, 2.00 mmol) was added thereto to initiate a reaction. After stirring at 30° C. for 72 hours, the reaction solution was filtered through Celite, and the solvent was distilled off, thereby obtaining a crude reaction product. Then, the ester and the alcohol were isolated by silica gel column chromatography (hexane/ethyl acetate (10:1)). Their optical purities were determined by HPLC using a chiral column. The spectrum data is shown below.

(S)-1c:

Isolated yield 60%; Optical purity 52% ee $[\alpha]^{28}{}_D$=−17.6 (c 1.03, CHCl$_3$)

$^1$H NMR (CDCl$_3$, 500 MHz) 0.95 (t, J=7.0 Hz, 3H), 1.83-1.95 (m, 3H), 4.78 (t, J=5.3 Hz, 1H), 7.45-7.49 (m, 3H), 7.79-7.85 (m, 4H)

HPLC: Chiralcel OJ-H, hexane/i-PrOH (9:1), Flow rate 0.5 mL/min., Detected wavelength 254 nm, (S)-1c 24.4 min., (R)-1c 33.5 min.

(R)-2c:

Isolated yield 31%; Optical purity 96% ee $[\alpha]^{24}{}_D$=+98.8 (c 1.06, CHCl$_3$)

$^1$H NMR (CDCl$_3$, 500 MHz) 0.91 (t, J=7.5 Hz, 3H), 1.91-2.03 (m, 2H), 2.10 (s, 3H), 5.83 (t, J=7.0 Hz, 1H), 7.45-7.48 (m, 3H), 7.78-7.84 (m, 4H)

HPLC: Chiralcel OJ-H, hexane/i-PrOH (9:1), Flow rate 0.5 mL/min., Detected wavelength 254 nm, (R)-2c 18.7 min., (S)-2c 25.7 min.

Example 22

Chemical Modification of Magnetic Ceramic Material (Fe$_3$O$_4$) Using 3-methacryloxypropyltrimethoxysilane In accordance with the above-described general procedure, the magnetic ceramic material (Fe$_3$O$_4$) was chemically modified using 3-methacryloxypropyltrimethoxysilane, as shown in the following formula.

[Chem. 26]

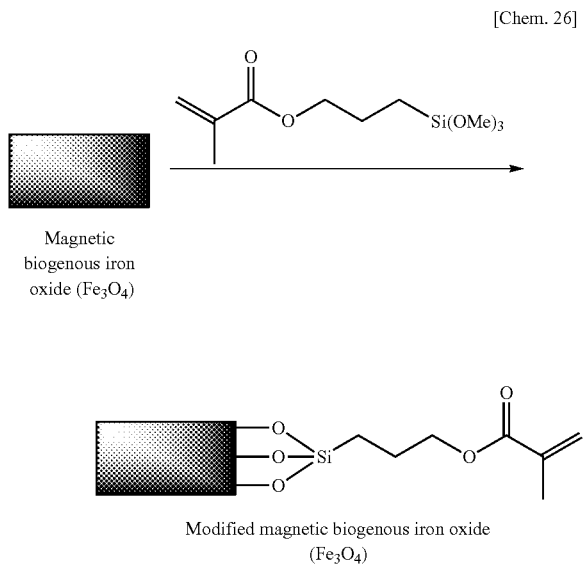

Elemental analysis of the obtained chemically modified magnetic ceramic material ($Fe_3O_4$) resulted in C: 1.10% and N: 0.00%. The organic group loading calculated from this carbon content was 1.6% (w/w) (0.10 mmol/g).

Example 23

Immobilization of *Burkholderia cepacia*-Derived Lipase (BCL) on the Modified Magnetic Ceramic Material ($Fe_3O_4$)

*Burkholderia cepacia* lipase (BCL) (Wako Pure Chemical Ind. Ltd., Lipase PS IM Amano, Immobilized on Diatomaceous Earth, 6.25 g), a phosphate buffer (10 mM, pH 7.0, 25 mL), and a stirring bar were placed in a pear-shaped flask and stirred at room temperature for 3 hours. The mixture was subjected to suction filtration using a Büchner funnel, thereby obtaining an aqueous enzyme solution. The aqueous enzyme solution was placed in a dialysis membrane (molecular weight cut-off 10,000) and dialyzed against a phosphate buffer (10 mM, pH 7.0, 500 mL, twice for 30 minutes, twice for 1 hour, and once for 12 hours). The dialyzed aqueous enzyme solution (21.5 mL) and the modified magnetic ceramic material ($Fe_3O_4$) (obtained in Example 22) (102 mg), which had been preliminarily treated with 3-methacryloxypropyltrimethoxysilane, were placed in a pear-shaped flask and subjected to shaking (125 rpm) at 27° C. for 24 hours. The resulting product was transferred to a centrifuge tube, and the precipitate obtained by centrifugation (10,000 rpm, 10 minutes) was vacuum-dried, thereby obtaining 110 mg of chemically modified magnetic ceramic material-immobilized enzyme BCL.

The protein content in the supernatant collected after the centrifugation and in the aqueous enzyme solution used for immobilization was quantified by the Bradford method, and the lipase loading was calculated. The amount of the enzyme carried in the powder (102 mg) was 3.3 mg (3.3% (w/w)).

Kinetic Optical Resolution of Chiral Alcohol Using the Chemically Modified Magnetic Ceramic Material-Immobilized Enzyme (1)

[Chem. 27]

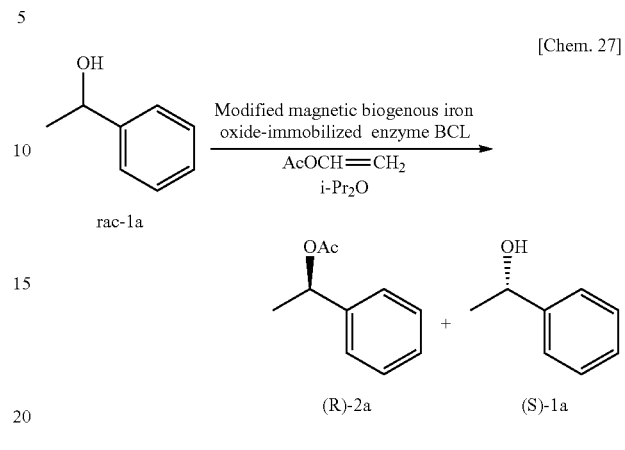

1-Phenylethanol 1a (122 μL, 1.00 mmol), the chemically modified magnetic ceramic material-immobilized enzyme BCL (13.9 mg) obtained in Example 23, Molecular sieve 3A (3 particles), and dry diisopropyl ether (5 mL) were placed in a test tube and stirred at 30° C. for 30 minutes. Then, vinyl acetate (185 μL, 2.00 mmol) was added thereto to initiate a reaction. After stirring at 30° C. for 2 hours, the reaction solution was filtered through Celite, and the solvent was distilled off, thereby obtaining a crude reaction product. Then, the ester and the alcohol were isolated by silica gel column chromatography (hexane/diethyl ether (10:1)). Their optical purities were determined by gas chromatography using a chiral column.

The spectrum data is shown below.

(S)-1a:
Isolated yield 60%; Optical purity 64% ee
$[\alpha]^{30}_D = -38.0$ (c 1.03, $CHCl_3$)
$^1$H NMR ($CDCl_3$, 300 MHz) 1.51 (d, J=6.3 Hz, 3H), 1.77 (d, J=3.0 Hz, 1H), 4.87-4.95 (m, 1H), 7.28-7.41 (m, 5H)
GC: CP-cyclodextrin-β-2,3,6-M-19, Inj. 250° C., Col. 95° C., Det. 220° C., (R)-1a 30.0 min., (S)-1a 32.6 min.

(R)-2a:
Isolated yield 35%; Optical purity >99% ee
$[\alpha]^{31}_D = +109$ (c 1.02, $CHCl_3$)
$^1$H NMR ($CDCl_3$, 300 MHz) 1.54 (d, J=6.8 Hz, 3H), 2.07 (s, 3H), 5.88 (q, J=6.8 Hz, 1H), 7.27-7.36 (m, 5H)
GC: CP-cyclodextrin-β-2,3,6-M-19, Inj. 250° C., Col. 95° C., Det. 220° C., (S)-2a 24.6 min., (R)-2a 27.5 min.

Comparison of Performance

As shown in the table below, organic-inorganic composite materials were compared for their performance as an enzyme immobilization carrier. The organic-inorganic composite materials that were compared were obtained by chemical modification of the *Leptothrix ochracea*-derived ceramic material obtained in the isolation and purification (1), the magnetic ceramic material (γ-$Fe_2O_3$) obtained in Example 18, or maghemite (Toda Kogyo Corp.), using 3-methacryloxypropyltrimethoxysilane. (These are referred to as BIOX-M (equivalent to the product obtained in Example 2), m-BIOX-M (equivalent to the product obtained in Example 19), and γ-$Fe_2O_3$-M, respectively.) Secondary alcohols 1a to 1c were reacted under the same conditions. The TOF values represent an enzyme catalyst turnover frequency per unit time. BIOX-M shows the most excellent catalyst activity as a carrier. Compared with the case where BIOX-M was used as a carrier, the use of m-BIOX-M as a carrier is slightly insufficient in terms of the catalyst activity, but is excellent in exhibiting magnetism. Although both are magnetic iron oxides, the use of m-BIOX-M as a carrier showed much higher catalyst activity, compared with the case where a synthetic iron oxide ($\gamma$-Fe$_2$O$_3$-M) was used as a carrier. The comparisons above suggest that ceramic materials available in nature are more appropriate as an immobilization carrier than artificially synthesized iron oxides.

TABLE 5

Kinetic optical resolution[a] of secondary alcohols with the use of the modified ceramic material (BIOX-M), modified magnetic ceramic material (m-BIOX-M), or modified synthesized maghemite ($\gamma$-Fe$_2$O$_3$-M) supported immobilized lipase (BCL)

| Entry | Carrier | 1 | Time/h | c[b] | % Yield[c] (% ee) | | E value[d] | TTN[e] | TOF[f] |
|---|---|---|---|---|---|---|---|---|---|
| | | | | | (R)-2 | (S)-1 | | | |
| 1 | BIOX-M | 1a | 1 | 46 | 23 (98) | 31 (83) | 259 | 33,000 | 33,000 |
| 2 | BIOX-M | 1b | 1 | 41 | 40 (>99) | 56 (69) | >413 | 29,000 | 29,000 |
| 3 | BIOX-M | 1c | 12 | 44 | 40 (97) | 59 (77) | 154 | 32,000 | 2,600 |
| 4 | m-BIOX-M | 1a | 2.5 | 47 | 40 (>99) | 48 (89) | >600 | 34,000 | 13,000 |
| 5 | m-BIOX-M | 1b | 6 | 50 | 40 (99) | 44 (>99) | >1057 | 36,000 | 6,000 |
| 6 | m-BIOX-M | 1c | 24 | 34 | 28 (97) | 53 (51) | 109 | 24,000 | 1,000 |
| 7 | $\gamma$-Fe$_2$O$_3$-M | 1a | 6 | 31 | 31 (>99) | 69 (45) | >310 | 22,000 | 3,700 |
| 8 | $\gamma$-Fe$_2$O$_3$-M | 1b | 12 | 26 | 24 (>99) | 62 (34) | >277 | 19,000 | 1,600 |
| 9 | $\gamma$-Fe$_2$O$_3$-M | 1c | 72 | 22 | 15 (69) | 75 (19) | 7 | 16,000 | 200 |

[a]Reaction condition: immobilized lipase (enzyme weight: maintained at 0.46 mg), 1 (1.00 mmol), vinyl acetate (2.00 mmol), molecular sieve 3A (3 particles), dry diisopropyl ether (5 mL), 30° C.
[b]Conversion rate: calculated from c = ee(1)/(ee(1) + ee(2))
[c]Isolated yield
[d]E value is calculated from E = ln[1 − c(1 + ee(2))]/ln[1 − c(1 − ee(2))]
[e]Enzyme catalyst turnover frequency
[f]Enzyme catalyst turnover frequency per unit time

The invention claimed is:

1. An organic-inorganic composite material obtained by chemically modifying a microorganism derived ceramic material comprising a Fe atom and a Si atom with an organic group, wherein the chemical modification with the organic group is performed by reacting the microorganism derived ceramic material with a silane coupling agent,
   wherein the organic group contains at least one functional group selected from the group consisting of a carboxyl group, a carboxylic acid ester group, an amide group, an imido group, a cyano group, an isocyano group, an aldehyde group, a ketone group, an imino group, an amino group, an azido group, a nitro group, a hydroxy group, an ether group, an epoxy group, an isocyanato group, an isothiocyanato group, an alkyl group, an aryl group, an alkenyl group, an alkynyl group, a thiol group, a sulfide group, a sulfonic acid group, a sulfonic acid ester group, a sulfoxide group, a heterocyclic ring, a halogen atom, a silicon atom, a titanium atom, an aluminum atom and a phosphorus atom,
   wherein the microorganism is a bacterium that belongs to the genus *Leptothrix*, *Gallionella*, *Sphaerotilus*, *Clonothrix*, *Toxothrix*, *Sideromonas*, *Siderocapsa*, or *Siderococcus*, and
   wherein silane coupling agent loading on the microorganism-derived ceramic material is at least 6.2% (w/w) calculated from the carbon content.

2. The organic-inorganic composite material according to claim 1, wherein the element ratio of iron, silicon, and phosphorus is 66-87:2-27:1-32 by atomic %.

3. The organic-inorganic composite material according to claim 1, wherein the microorganism derived ceramic material is a material to which magnetism has been imparted.

4. A catalytic-organic inorganic composite material comprising the organic inorganic composite material of claim 1 or 3 and a catalyst immobilized thereon.

5. The catalytic-organic inorganic composite material according to claim 4, wherein the catalyst is at least one member selected from the group consisting of an enzyme, an organic catalyst, and a metal complex catalyst.

6. An organic-inorganic composite material comprising the organic inorganic composite material of claim 1 or 3 and a dye immobilized thereon.

7. An immobilized catalyst comprising the catalytic-organic-inorganic composite material of claim 4 as an active ingredient.

8. The organic-inorganic composite material according to claim 1, wherein the microorganism is *Leptothrix cholodnii* OUMS1 (NITE BP 860).

9. The organic-inorganic composite material according to claim 1, wherein the organic group functions as a catalyst.

10. An immobilized catalyst comprising the organic-inorganic composite material of claim 9 as an active ingredient.

11. The organic-inorganic composite material according to claim 1, wherein the composite material is capable of 4.6% (w/w) lipase loading.

12. A process for producing an organic-inorganic composite material, comprising reacting a microorganism derived ceramic material comprising a Fe atom and a Si atom with at least one member selected from the group consisting of:
   a silane coupling agent represented by formula (1):

wherein:
   Y represents $R^4R^5N$—, $R^7R^8N$—$R^6$—$NR^4$—, or $R^{11}R^{10}N$—$R^9$—$R^7N$—$R^6$—$NR^4$—,
   a phenyl group, a 3,4 epoxycyclohexyl group, a halogen atom, a mercapto group, an isocyanate group, an optionally substituted glycidyl group, a glycidoxy group, an optionally substituted vinyl group, a methacryloxy group, an acryloxy group, a ureido group, an optionally substituted methacryl group, an optionally substituted epoxy group, an optionally substituted phosphonium halide group, an optionally substituted ammonium halide group, or an optionally substituted acryl group, or Y and $R^1$ ($Y$—$R^1$) conjointly represent a vinyl group;

$R^4$, $R^5$, $R^7$, $R^8$, $R^{10}$ and $R^{11}$ independently represent a hydrogen atom or a $C_{1-6}$ alkyl group;

$R^6$ and $R^9$ independently represent a $C_{2-6}$ alkylene group;

$R^1$ is a single bond, an alkylene group, or a phenylene group, or $R^1$ and Y (Y $R^1$) conjointly represent a vinyl group;

each $R^2$ independently represents an alkyl group or a phenyl group;

each $R^3$ independently represents a hydroxy group or an alkoxy group; and n is an integer of 0 to 2; and a silane coupling agent represented by formula (2):

$$R^{12}{}_3Si-NH_mR^{13}{}_{2-m} \quad (2)$$

wherein each $R^{12}$ independently represents an alkyl group, each $R^{13}$ independently represents an alkyl group or an alkylsilane group, and m is an integer or 0 to 2, wherein the microorganism is a bacterium that belongs to the genus *Leptothrix, Gallionella, Sphaerotilus, Clonothrix, Toxothrix, Sideromonas, Siderocapsa*, or *Siderococcus*, and wherein silane coupling agent loading on the microorganism-derived ceramic material is at least 6.2% (w/w) calculated from the carbon content.

13. The process for producing the organic-inorganic composite material of claim 12, wherein the composite material is capable of 4.6% (w/w) lipase loading.

14. The process for producing the organic-inorganic composite material of claim 12, further comprising chemically modifying the organic group of the chemically modified organic-inorganic composite material, wherein the further chemical modification is an amidation reaction by condensation of a carboxylic acid and an amine; an esterification reaction by condensation of a carboxylic acid and an alcohol; a nucleophilic addition reaction of an amine or an alcohol to epoxide; a nucleophilic substitution reaction of an amine, an alcohol or a thiol to an organic halogen compound; a Michael addition reaction of an amine or thiol to an $\alpha,\beta$-unsaturated carbonyl group; an imine formation reaction by dehydration condensation of an amino group and an aldehyde group; a carbon-carbon bonding formation reaction using an organometallic reagent; or a metal complex catalyst carbon-carbon bonding formation reaction.

15. A process for producing a catalytic-organic inorganic composite material, comprising immobilizing a catalyst on the organic group contained in the organic-inorganic composite material obtained by the process of claim 12.

16. The process for producing the organic-inorganic composite material of claim 12, further comprising binding a dye to the organic group contained in the chemically modified organic inorganic-composite material.

* * * * *

SEQUENCE LISTING

```
<160> NUMBER OF SEQ ID NOS: 9

<210> SEQ ID NO 1
<211> LENGTH: 1418
<212> TYPE: DNA
<213> ORGANISM: Leptothrix cholodnii

<400> SEQUENCE: 1
catgccttac acatgcaagt cgaacggtag aggagcaatc ctcgagagtg gcgaacgggt      60
gagtaatgta tcggaacgtg cccagtagtg ggggatagcc cggcgaaagc cggattaata     120
ccgcatgaga cctgagggtg aaagcggggg actcgcaagg gcctcgcgct actggagcgg     180
ccgatatcag attaggtagt tggtggggta aaagcctacc aagcctgcga tctgtagctg     240
gtctgagagg acgaccagcc acactgggac tgagacacgg cccagactcc tacgggaggc     300
agcagtgggg aattttggac aatgggcgaa agcctgatcc agccatgccg cgtgcgggaa     360
gaaggccttc gggttgtaaa ccgcttttgt cagggaagaa atcctttgag ttaataacctc    420 ggagggatga cggtacctga agaataagca ccggctaact acgtgccagc agccgcggta     480
atacgtaggg tgcaagcgtt aatcggaatt actgggcgta aagcgtgcgc aggcggttgt     540
gtaagacaga tgtgaaatcc ccgggctcaa cctgggaact gcatttgtga ctgcacagct     600
agagtacggt agagggggat ggaattccgc gtgtagcagt gaaatgcgta gatatgcgga     660
ggaacaccga tggcgaaggc aatcccctgg acctgtactg acgctcatgc acgaaagcgt     720
ggggagcaaa caggattaga taccctggta gtccacgccc taaacgatgt caactggttg     780
ttgggagggt ttcttctcag taacgaagct aacgcgtgaa gttgaccgcc tggggagtac     840
ggccgcaagg ttgaaactca aaggaattga cggggacccg cacaagcggt ggatgatgtg     900
gtttaattcg atgcaacgcg aaaaccttac cctacccttg acatgtcaag aatcttgcag     960
```

| | |
|---|---|
| agatgtggga gtgctcgaaa gagaacttga acacaggtgc tgcatggccg tcgtcagctc | 1020 |
| gtgtcgtgag atgttgggtt aagtcccgca acgagcgcaa cccttgtcat tagttgctac | 1080 |
| gaaagggcac tctaatgaga ctgccggtga caaaccggag gaaggtgggg atgacgtcag | 1140 |
| gtcctcatgg cccttatggg tagggctaca cacgtcatac aatggccggt acagagggca | 1200 |
| gccaacccgc gaggggagc caatcccaga aaaccggtcg tagtccggat cgcagtctgc | 1260 |
| aactcgactg cgtgaagtcg gaatcgctag taatcgcgga tcagcttgcc gcggtgaata | 1320 |
| cgttcccggg tcttgtacac accgcccgtc acaccatggg agcgggttct gccagaagta | 1380 |
| gttagcctaa ccgcaaggag ggcgattacc acggcagg | 1418 |

```
<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
```

| | |
|---|---|
| agagtttgat cmtggctcag | 20 |

```
<210> SEQ ID NO 3
<211> LENGTH: 19
<212> TYPE: DNA
<213> ORGANISM: Artificial Sequence
<220> FEATURE:
<223> OTHER INFORMATION: primer

<400> SEQUENCE: 3
```

| | |
|---|---|
| ggytaccttg ttacgactt | 19 |

```
<210> SEQ ID NO 4
<211> LENGTH: 10
<212> TYPE: DNA
<213> ORGANISM: Artificial Sequence
<220> FEATURE:
<223> OTHER INFORMATION: primer

<400> SEQUENCE: 4
```

| | |
|---|---|
| ggtgcgggaa | 10 |

```
<210> SEQ ID NO 5
<211> LENGTH: 10
<212> TYPE: DNA
<213> ORGANISM: Artificial Sequence
<220> FEATURE:
<223> OTHER INFORMATION: primer

<400> SEQUENCE: 5
```

| | |
|---|---|
| gtttcgctcc | 10 |

```
<210> SEQ ID NO 6
<211> LENGTH: 10
<212> TYPE: DNA
<213> ORGANISM: Artificial Sequence
<220> FEATURE:
<223> OTHER INFORMATION: primer

<400> SEQUENCE: 6
```

| | |
|---|---|
| gtagacccgt | 10 |

```
<210> SEQ ID NO 7
<211> LENGTH: 10
```

```
<212> TYPE: DNA
<213> ORGANISM: Artificial Sequence
<220> FEATURE:
<223> OTHER INFORMATION: primer

<400> SEQUENCE: 7
aagagcccgt                                                             10

<210> SEQ ID NO 8
<211> LENGTH: 10
<212> TYPE: DNA
<213> ORGANISM: Artificial Sequence
<220> FEATURE:
<223> OTHER INFORMATION: primer

<400> SEQUENCE: 8
aacgcgcaac                                                             10

<210> SEQ ID NO 9
<211> LENGTH: 10
<212> TYPE: DNA
<213> ORGANISM: Artificial Sequence
<220> FEATURE:
<223> OTHER INFORMATION: primer

<400> SEQUENCE: 9
cccgtcagca                                                             10
```